(12) United States Patent
Dutta

(10) Patent No.: US 9,034,877 B2
(45) Date of Patent: May 19, 2015

(54) BIFUNCTIONAL/POLYFUNCTIONAL DOPAMINE D2/D3 AGONIST AS NEUROPROTECTIVE AGENTS FOR TREATMENT OF NEURODEGENERATIVE DISEASES

(75) Inventor: Aloke K. Dutta, Troy, MI (US)

(73) Assignee: Wayne State University, Detroit, MI (US)

( * ) Notice: Subject to any disclaimer, the term of this patent is extended or adjusted under 35 U.S.C. 154(b) by 35 days.

(21) Appl. No.: 13/264,505

(22) PCT Filed: Apr. 21, 2010

(86) PCT No.: PCT/US2010/031900
§ 371 (c)(1),
(2), (4) Date: Oct. 14, 2011

(87) PCT Pub. No.: WO2010/123995
PCT Pub. Date: Oct. 28, 2010

(65) Prior Publication Data
US 2012/0108815 A1  May 3, 2012

Related U.S. Application Data

(60) Provisional application No. 61/171,267, filed on Apr. 21, 2009.

(51) Int. Cl.
| | | |
|---|---|---|
| C07D 215/26 | (2006.01) |
| C07D 215/20 | (2006.01) |
| C07D 215/22 | (2006.01) |
| C07D 215/227 | (2006.01) |
| C07D 215/233 | (2006.01) |
| C07D 417/12 | (2006.01) |
| A61K 31/50 | (2006.01) |
| C07D 209/08 | (2006.01) |
| C07D 215/38 | (2006.01) |
| C07D 215/46 | (2006.01) |
| C07D 215/54 | (2006.01) |
| C07D 231/56 | (2006.01) |
| C07D 277/82 | (2006.01) |
| C07D 307/85 | (2006.01) |
| C07D 333/70 | (2006.01) |

(52) U.S. Cl.
CPC .............. *A61K 31/50* (2013.01); *C07D 209/08* (2013.01); *C07D 215/26* (2013.01); *C07D 215/38* (2013.01); *C07D 215/46* (2013.01); *C07D 215/54* (2013.01); *C07D 231/56* (2013.01); *C07D 277/82* (2013.01); *C07D 307/85* (2013.01); *C07D 333/70* (2013.01); *C07D 417/12* (2013.01)

(58) Field of Classification Search
None
See application file for complete search history.

(56) References Cited

U.S. PATENT DOCUMENTS

2006/0020132 A1   1/2006   Dutta

OTHER PUBLICATIONS

Burger's Medicinal Chemistry, edited by Manfred E. Wolff, 5th Ed. Part 1, pp. 975-977 (1995).*
Banker et al. "Modern Pharmaceutics", 3rd Ed. p. 596 (1996).*
Biswas et al. J.Med.Chem. 51,pp. 3005-3019 (2008).*
Ghosh et al. J.Med.Chem. 53, pp. 2114-2125 (Feb. 10, 2010).*
International Search Report dated Jun. 24, 2010 from corresponding PCT/US2010/031900, filed Apr. 21, 2010, 2 pgs.

* cited by examiner

*Primary Examiner* — Emily Bernhardt
(74) *Attorney, Agent, or Firm* — Brooks Kushman P.C.

(57) ABSTRACT

A precursor for the deposition of a thin film by atomic layer deposition is provided. The compound has the formula $M_xL_y$ where M is a metal and L is an amidrazone-derived ligand or an amidate-derived ligand. A process of forming a thin film using the precursors is also provided.

11 Claims, 26 Drawing Sheets

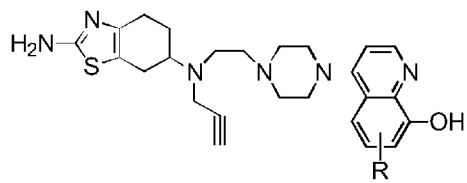
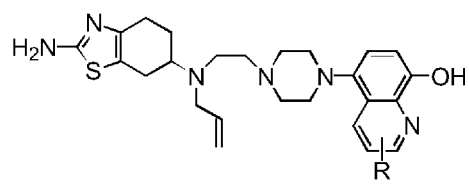
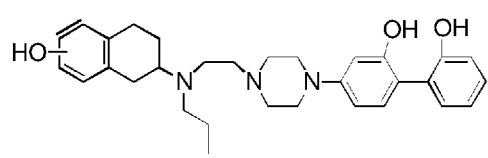
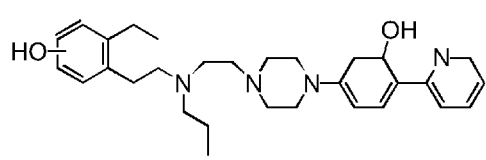
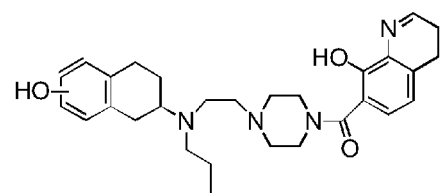
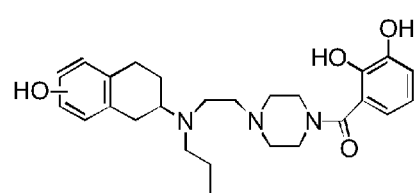
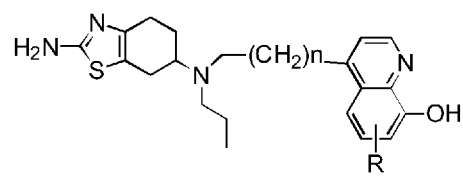
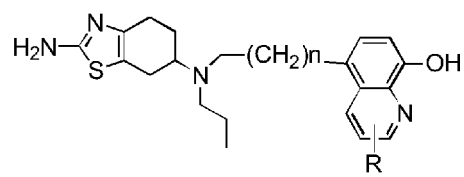
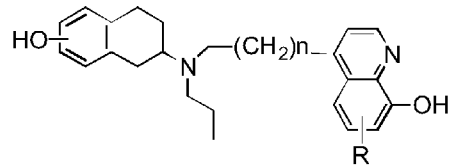
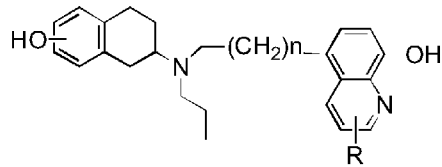
*Fig. 1B* a. n-Propylamine, NaCNBH$_3$, CH$_3$COOH, dichloroethane, RT, overnight; b. (+)-chlocyphos, EtOH; c. (-)-chlocyphos, EtOH; d. chloroacetyl chloride, TEA, dichloromethane, 0 °C, 30 min; e. (Boc)$_2$O, CH$_2$Cl$_2$, 0 °C, 2 h; f. K$_2$CO$_3$, CH$_3$CN, 80 °C, 2 h; g. TFA/DCM (1/1), RT, overnight; h. LiAlH$_4$, THF, reflux, 2 h; i. BBr$_3$, -40 °C, CH$_2$Cl$_2$, overnight Scheme-2 a. HCl (32% water), HCHO (37% in water), 0 °C, RT, 8 h; b. N-substitued piperazine (9a or 9b), (Me$_2$CH)$_2$-NEt, CHCl$_3$, RT, 1 day.

Scheme-3 a. Trimethylorthoformate, reflux, 1 h; b. o-anisidine, DMF (cat. amt), relux, 2 h; c. Diphenyl ether, 300 °C, 15 min; d. POCl$_3$, reflux, 2h.

Table 1.

| Compound | Ki, (nM), D2L [³H]Spiperone | Ki, (nM), D3 [³H]Spiperone | D2L/D3 |
| --- | --- | --- | --- |
| 7-OH-DPAT | 202 ± 34 | 2.35 ± 0.29 | 86.0 |
| (-)-5-OH-DPAT | 58.8 ± 11.0 | 1.36 ± 0.28 | 43.2 |
| 1a[a] | 26.0 ± 7.5 | 0.825 ± 0.136 | 31.5 |
| 1b | 3.74 ± 0.70 | 0.186 ± 0.030 | 19.7 |
| 12a | 86.0 ± 4.1 | 5.57 ± 1.15 | 15.4 |
| (+)19b | 20.7 ± 1.5 | 7.73 ± 0.64 | 2.67 |
| (-)19b | 3.75 ± 0.63 | 1.28 ± 0.08 | 2.92 |
| 19a | 15.9 ± 2.1 | 0.818 ± 0.165 | 19.6 |
| 19b | 13.8 ± 0.6 | 1.35 ± 0.22 | 10.2 |
| (+)19a | 4.55 ± 0.59 | 1.27 ± 0.15 | 3.58 |
| 12b | 41.4 ± 7.1 | 3.71 ± 0.48 | 11.2 |

*Fig. 7A*

Table 2.

| Compound | CHO-D2 | | CHO-D3 | | D2/D3 |
|---|---|---|---|---|---|
| | $EC_{50}$ (nM)[a] [$^{35}$S]GTPγS | %$E_{max}$ | $EC_{50}$ (nM)[a] [$^{35}$S]GTPγS | %$E_{max}$ | |
| Dopamine | 209 ± 29 | 100 | 4.76 ± 0.87 | 100 | 43.9 |
| Ropinirole | 304 ± 11 | 73.9 ± 0.9 | 10.3 ± 1.5 | 66.6 ± 8.1 | 29.5 |
| (−)19b | 4.51 ± 0.93 | 106 ± 4 | 1.58 ± 0.31 | 92.6 ± 3.6 | 2.85 |
| (+)19a | 1.69 ± 0.16 | 55.3 ± 4.8 | 0.74 ± 0.15 | 99.8 ± 1.4 | 2.26 | a. EC50 is the concentration producing half-maximal stimulation; for each compound, maximal stimulation (Emax) is expressed as percent of the Emax observed with 1 mM (D2) or 100 uM (D3) of the full agonist DA (%Emax). Results are the means +/- SEM for 3-6 experiments each performed in triplicate.

*Fig. 8*

Scheme 5

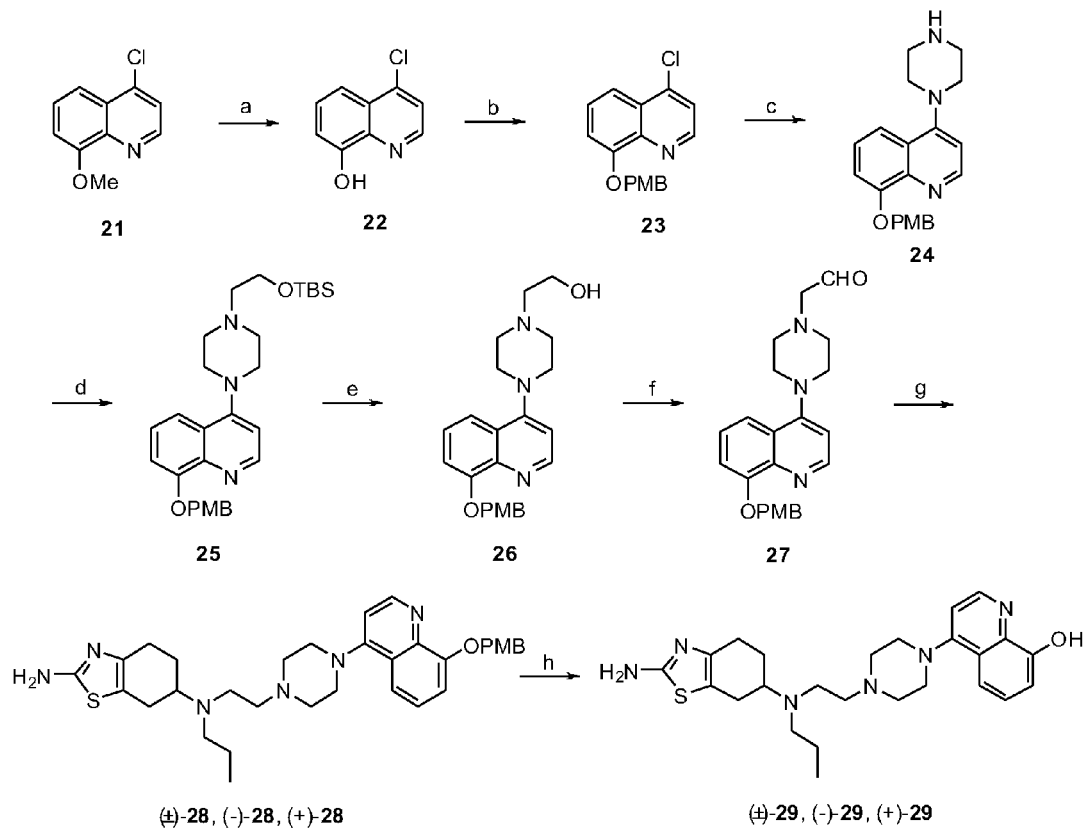

(a) 48% Aq. HBr, reflux, 26 h; (b) *p*-methoxybenzyl chloride, K₂CO₃, *n*-Bu₄NI, DMF, 80 °C, 10 h; (c) piperazine, isopropanol, 100 °C, 46 h; (d) (2-bromo-ethyl)-*tert*-butyldimethylsilane, K₂CO₃, acetonitrile, reflux, 14 h; (e) *n*-Bu₄NF, THF, rt, 1.5 h; (f) oxalyl chloride, DMSO, TEA, CH₂Cl₂, -78 °C, 2 h; (g) (±)-pramipexole or (-)-pramipexole or (+)-pramipexole, NaBH(OAc)₃, CH₂Cl₂, rt, 48 h; (h) TFA, DCM, rt, 3.5 h.

*Fig. 15*

Table 3.

| Compound | Ki, (nM), D2L [³H]Spiperone | Ki, (nM), D3 [³H]Spiperone |
|---|---|---|
| (-)-29 (D-390) | 27.1 (7) ± 5.0 | 4.98 (5) ± 0.78 |
| (±)-29 (D-385) | 45.0 (5) ± 8.1 | 4.03 (4) ± 0.83 |

*Fig. 16*

Scheme 8

Reaction conditions: (a) 2-bromoethanol, K₂CO₃, CH₃CN; (b) Swern oxidation; (c) Na(OAc)₃BH, acetic acid, dichloroethane; (d) aq HBr (48%), reflux, 3h; (e) EDCl, HOBt, Et₃N

Scheme 9

Reaction conditions: (a) triisopropylsilyl chloride, NaH, THF; (b) 5, PdCl$_2$[P(o-tol)$_3$]$_2$, NaOtBu, xylenes, reflux, overnight; (c) 1M Bu$_4$NF, THF, rt, 4h (d) TFA, CH$_2$Cl$_2$ (e) 3a, K$_2$CO$_3$, CH$_3$CN, reflux (f) i: BH$_3$, THF ii: HBr, reflux Table 4.

| Compound | $K_i$, (nM), $D_{2L}$ [$^3$H]Spiperone | $K_i$, (nM), $D_3$ [$^3$H]Spiperone | $D_{2L}/D_3$ |
|---|---|---|---|
| (±)-7-OH-DPAT | 311 ± 47 | 6.19 ± 1.4 | 50.2 |
| (−)-5-OH-DPAT | 58.8 (5) ± 11.0 | 1.36 (4) ± 0.28 | 43 |
| D-237[a] | 26.0 ± 7.5 | 0.825 ± 0.136 | 31.5 |
| D-264[b] | 264 ± 40 | 0.92 ± 0.23 | 253 |
| D-315 | 40.6 ± 3.6 | 1.77 ± 0.42 | 22.9 |
| 40c (D-282) | 116 ± 12 | 3.72 ± 1.12 | 31.2 |
| 40d (D-283) | 100 ± 1 | 4.82 ± 1.10 | 20.7 |
| 40b (D-284) | 144 ± 5 | 3.87 ± 0.65 | 37.2 |
| 40a (D-285) | 65.9 ± 9 | 1.67 ± 0.26 | 39.5 |
| 52 (D-286) | 30.0 ± 4.9 | 2.00 ± 0.48 | 15.0 |
| (−)-45 (D-313) | 157 ± 35 | 2.27 ± 0.52 | 69.2 |
| 40e (D-328) | 51.2 (± 7.0) | 0.550 (4) ± 0.084 | 93.1 |
| (−)-40e (D-366) | 47.5 (5) ± 6.2 | 0.570 ± 0.094 | 83 |
| (+)-40e (D-365) | 113 (6) ± 21 | 3.73 (4) ± 0.56 | 30.2 |
| 40f (D-329) | 58.9 ± 7.9 | 3.62 (5) ± 0.79 | 16.3 |
| 40g (D-334) | 28.0 ± 2.4 | 2.83 (5) ± 0.59 | 9.89 |
| 40h (D-333) | 132 ± 8 | 5.23 (5) ± 1.13 | 25.2 |
| 40i (D-332) | 76.9 ± 9.2 | 1.69 (4) ± 0.41 | 45.5 |
| 40j (D-331) | 158 ± 22 | 5.18 (5) ± 0.75 | 30.5 |

*Fig. 21*

Table 5.

|  | CHO-D2 | | AtT-D3 | | |
| --- | --- | --- | --- | --- | --- |
| Compound | EC50 (nM) [35S]GTPγS | %Emax | EC50 (nM) [35S]GTPγS | %Emax | D2/D3 |
| dopamine | 209 (4) ± 29 | 100 (definition) | 8.53 ± 0.62 | 100 (definition) | 24.5 |
| D-264[b] | 19.9 ± 0.9 | 119 ± 6 | 0.085 ± 0.016 | 102 ± 19 | 248 |
| (-)-D-237[a] | 2.22 ± 0.27 | 63.4 ± 3.5 | 0.121 ± 0.002 | 78.5 ± 9.5 | 18.3 |
| (-)-45 (D-313) | 10.4 (4) ± 1.6 | 77.8 ± 0.9 | 0.14 ± 0.03 | 92.2 ± 5.8 | 74.3 |
| (-)-5-OH-DPAT | 41.2 ± 6.0 | 80.0 ± 4.4 | 1.23 ± 0.53 | 91.2 ± 1.0 | 33.5 |

*Fig. 22*

Scheme 10

Reagents: (i) bis-(2-Chloro-ethyl)-amine; (ii) CH₃COOH, Br₂; (iii) (Boc)₂O, Et₃N; (iv) 2-Methoxy boronic acid, Pd[P(Ph)₃]; (v) TFA; (vi) (2-Bromo ethoxy)-tert-butyl-dimethyl-silane, K₂CO₃; (vii) Bu₄NF; (viii) (COCl)₂, DMSO, Et₃N; (ix) Pramipexole, NaBH(OAc)₃; (x) BBr₃.

BIFUNCTIONAL/POLYFUNCTIONAL DOPAMINE D2/D3 AGONIST AS NEUROPROTECTIVE AGENTS FOR TREATMENT OF NEURODEGENERATIVE DISEASES

CROSS-REFERENCE TO RELATED APPLICATION

This application is the U.S. national phase of PCT Appln. No. PCT/US2010/031900 filed Apr. 21, 2010 which claims the benefit of U.S. provisional application Ser. No. 61/171,267 filed Apr. 21, 2009, the disclosures of which are incorporated in their entirety by reference herein.

STATEMENT REGARDING FEDERALLY SPONSORED RESEARCH OR DEVELOPMENT

The invention was made with Government support under Contract No. 5R01NS047198 awarded by NIH/NINDS. The Government has certain rights to the invention.

TECHNICAL FIELD

The present invention relates to compounds for treating neurodegenerative diseases.

BACKGROUND OF THE INVENTION

Parkinson's disease (PD) is a progressive disorder of the central nervous system that mainly affects motor and other functions. The cardinal clinical features of Parkinson's disease (PD) include resting tremor, rigidity, difficulty in initiating movement and postural instability. These symptoms develop as a result of slow degeneration of dopamine neuron in the substantia niagra resulting in production of less and less dopamine. The loss of dopaminergic neurons in the pars compacta region of the substantia nigra and the inhibition of nigrostriatal dopaminergic pathway results in development of dysfunction of movements. Even though the pathogenesis of PD is poorly understood, studies of the genetic mutations, neuropathology and other factors of PD have provided much insight into the pathophysiology of PD and the progression of this disease. Both oxidative stress and mitochondrial dysfunction have been strongly implicated in cell death. The presence of Lewy bodies (LBs) in the surviving neurons of the substantia nigra is the neuropathological hallmark of PD. The physical characteristics of LBs are round, eosinophilic, intracytoplasmic proteinaceous inclusions and they are found to contain principally polymeric α-synuclein proteins.

Evidence from various studies have consistently implicated iron in the pathophysiology of PD. Iron being the most abundant metal in the human body is particularly found in higher level in the brain and liver. The role of iron in the pathogenesis of PD has been strengthened by several observations. Higher levels of iron are generally found in the brains of PD patients compared to normal brains. Additionally, iron accumulation observed is higher in the substantia nigra region of people afflicted with PD. It is well known that free iron plays a role in generating of oxidative stress leading to dopamine cell death. The generation of hydroxyl radical from free iron occurs by the Fenton reaction (Equation 1). It has also been shown that the presence of iron can initiate aggregation of alpha-synuclein in LBs, implicated in dopamine cell death. The aggregation of alpha-synuclein possibly takes place via conversion of this molecule into β-pleated sheets. Recent studies have shown that overexpression of α-synuclein can form toxic aggregates in the presence of iron. This is believed to contribute to the formation of LBs via production of oxidative stress. Iron released from neuromelanin has also been reported to cause mitochondrial dysfunction and to reduce proteasomal function. All these evidences have further been corroborated by the fact that iron chelators are neuroprotective. Thus, a crucial role of iron in PD pathogenesis has been emphasized because of its capacity to enhance the production of oxygen radicals and accelerate neuronal degeneration. Oxidative stress can facilitate mutant protein aggregation, mimicking proteasomal malfunction. Thus, iron chelators can possibly sequester free iron and thereby prevent its ability to induce oxidative stress as a consequence of reactive hydroxyl radical generation $$H_2O_2 + Fe^{2+} \rightarrow OH^- + OH\cdot + Fe^{3+} \qquad \text{(Equation 1)}$$

Recently, bifunctional iron chelators were developed where an iron binding 8-hydroxy quinoline moiety was attached to N-propargyl amine and to the piperazine moiety to provide neuroprotective property via reduction of oxidative stress. Two such compounds, 5-((4-(2-hydroxyethyl)piperazin-1-yl)methyl)quinolin-8-ol (VK 28) and 5-((prop-2-ynylamino)methyl)quinolin-8-ol (M30), were shown to be antioxidant and neuroprotective in animal experiments.

Accordingly, there is a need for dopamine improved D2/D3 agonist molecules, and in particular, for improved D2/D3 agonist molecules with a capacity to bind to iron.

SUMMARY OF THE INVENTION

In at least one embodiment, the present invention solves one or more problems of the prior art by providing a compound having formula I for treating a neurodegenerative disease:

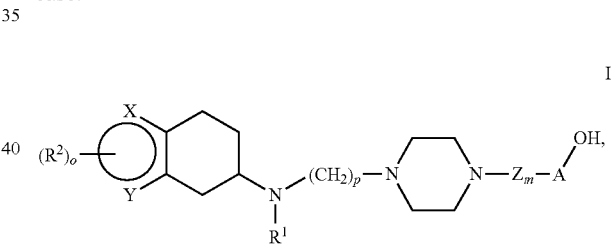

R¹ is an organo group;

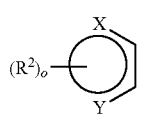

is an aromatic and optionally heterocyclic ring system containing 5 or 6 ring atoms and up to three heteroatoms individually selected from the group consisting of N, O, S, and Se;

R² are organyl groups;
o is 0, 1, 2, 3, or 4;
A is an aryl-containing group;
p is an integer from 1 to 6; and
$Z_m$ is absent or a divalent linking moiety; and
m is an integer representing the number of time Z is repeated.

In another embodiment of the present invention, a compound having formula VIIIa or VIIIb for treating a neurodegenerative disease is provided:

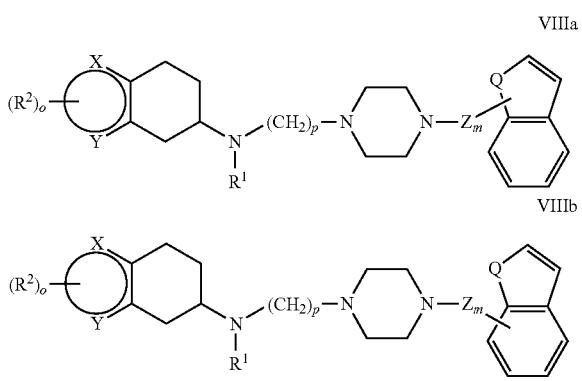

wherein $R^1$, $R^2$, o, p, Z, m, and

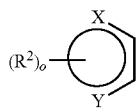

are the same as set forth above. Q is N—H, O, S, or N—R where R is hydrogen, alkyl, or aryl.

BRIEF DESCRIPTION OF THE DRAWINGS

Exemplary embodiments of the present invention will become more fully understood from the detailed description and the accompanying drawings, wherein:

FIGS. 1A, 1B, and 1C provide specific compounds of an embodiment of the present invention. In these figures R is H, alkyl, or aryl;

FIG. 7A provides Table 1 which set forth inhibition constants for competing for [3H]spiperone binding to cloned D2L and D3 receptors expressed in HEK cells. Results are means+SEM for 3-7 experiments each performed in triplicate;

FIG. 8 provides Table 2 which sets forth data related to stimulation of [$^{35}$S]GTPγS binding to hD2 and hD3 receptors expressed in CHO cells. $EC_{50}$ values (nM) are means±SEM for 3-6 experiments each performed in triplicate;

FIG. 15 provides part of a synthetic scheme for preparing compounds of an embodiment of the present invention;

FIG. 16 provides Table 3 which sets forth inhibition constants for competing for [3H]spiperone binding to cloned D2L and D3 receptors expressed in HEK cells.

FIG. 21 provides Table 4 which sets forth the affinity for cloned D2L and D3 receptors expressed in HEK cells measured by inhibition of [$^3$H]spiperone binding. Results are means±SEM for three to six experiments each performed in triplicate;

FIG. 22 provides Table 5 which shows data related to stimulation of [35S]GTPγS binding to the cloned hD2 receptor expressed in CHO cells and cloned hD3 receptor expressed in AtT-20 cells. EC50 is the concentration producing half-maximal stimulation; for each compound, maximal stimulation (Emax) is expressed as percent of the Emax observed with 1 mM (D2) or 100 μM (D3) of the full agonist DA (% Emax). Results are means±SEM for 3-4 experiments each performed in triplicate.

DETAILED DESCRIPTION OF THE INVENTION

Figure 1A:
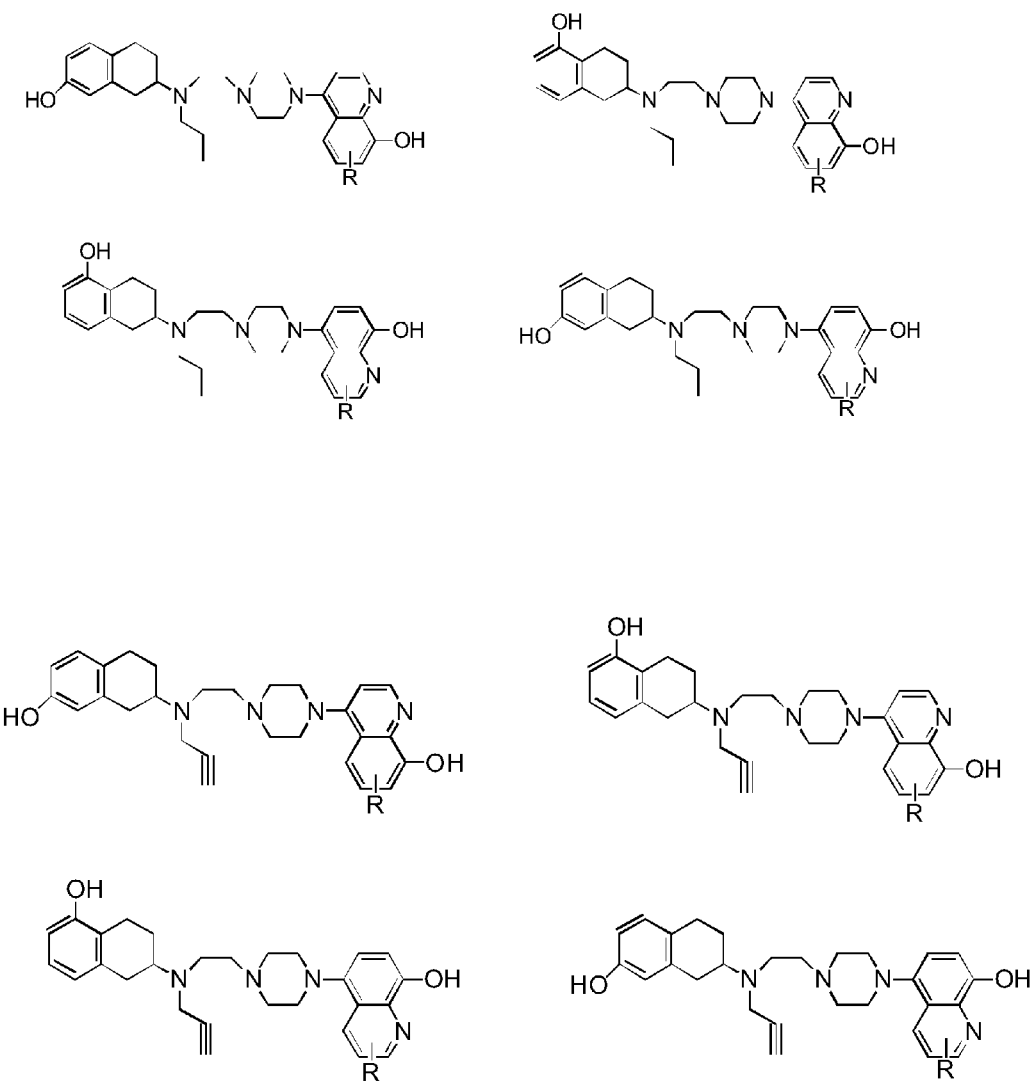

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention. Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

In at least one embodiment, the present invention provides a compound having formula I for treating a neurodegenerative and other related CNS diseases:

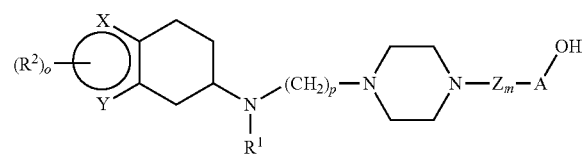

I $R^1$ is an organo group, preferably selected from among $C_{1-8}$ alkyl, $C_{2-8}$ alkenyl, $C_{2-8}$ alkynyl, $C_{4-8}$ cycloalkyl, $C_{4-8}$ cycloalkenyl, $C_{6-10}$ aryl, each of the foregoing alkyl, alkenyl, alkynyl, cycloalkyl, etc. groups optionally halo substituted, preferably fluoro and/or chloro substituted, or substituted by —CN, $C_{1-4}$ lower alkoxy, $C_{1-4}$ acyloxy, $C_{1-4}$ acyl, —C(O)—$R^4$, or —$R^5$—NH—$SO_2$—$NR^4{}_r$, where $R^4$ is H or organyl groups, preferably H, $C_{1-8}$ alkyl, $C_{1-8}$ alkenyl, $C_{4-8}$ cycloalkyl, $C_{4-8}$ cycloalkenyl, or $C_{6-10}$ aryl; and $R^5$ is $C_{1-8}$ alkylene and r is 2 or 3, with the proviso that when r is 3, the nitrogen of the $NR^4{}_r$ group will bear a positive formal charge; —$R^5$—NH—C(O)—$R^4$; —$R^5$—$NR^4{}_r$, —$R^5$—Ar where Ar is an aryl ring system, preferably a $C_{6-10}$ aryl ring system, optionally including one or more heteroatoms, preferably phenyl, thienyl, pyridyl, biphenyl, or naphthyl;

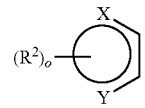

is an aromatic ring system. In a variation, it this moiety is an optionally heterocyclic ring system containing 5 or 6 ring atoms and up to three heteroatoms individually selected from the group consisting of N, O, S, and Se. This aromatic ring system is optionally substituted by o $R^2$ groups, where o is 0, 1, 2, 3, or 4, the upper limit bounded by the number of available substituent sites. In a variation, X and Y may be N, NR, O, S, and Se where R is hydrogen, alkyl, or aryl.

$R^2$ are organyl groups. In a variation, $R^2$ are $C_{1-10}$ hydrocarbon groups optionally containing one or more O, N, S, or Se heteroatoms. In another variation, $R^2$ are selected from among $C_{1-8}$ alkyl, $C_{2-8}$ alkenyl, $C_{2-8}$ alkynyl, $C_{4-8}$ cycloalkyl, $C_{4-8}$ cycloalkenyl; $C_{6-10}$ aryl, —$NR^3{}_q$ where $R^3$ individually are H or organyl groups. For example, $R^3$ may be H, $C_{1-8}$ alkyl, $C_m$ alkenyl, $C_{4-8}$ cycloalkyl, $C_{4-8}$ cycloalkenyl, $C_{6-10}$ aryl and q is 2 or 3, with the proviso that when q is 3, the group bears a positive formal charge; —NH—C(O)—$R^3$, —NH—C(O)—$NR^4{}_2$, and related compounds wherein the hydrocarbon groups in each case may optionally be substituted with —CN, $C_{1-4}$ lower alkyl, $OR^3$, —OH, halo, particularly fluoro and/or chloro, —$CF_3$, and the like. Two $R^2$ may also together form an alicyclic or aromatic fused five or six membered ring, optionally containing heteroatoms O, N, S, or Se. $R^3$ may also be arylsulfonyl, preferably 4-chlorophenylsulfonyl, 3,4-dichlorophenylsulfonyl; 4-(trifluoromethyl)phenylsulfonyl; $X^4$—Ar—$SC_2$ where $X^4$ is an electron withdrawing or electron donating substituent and Ar is an aromatic or heteroaromatic moiety; or keto, preferably phenylketo, 4-(trifluoromethyl)phenylketo, or aceto;

A is an aryl group. In one variation, A contains one or more heteroatoms. In another variation, A may be directly bonded to a nitrogen atom of the piperazinyl group. In still another variation, A is an aryl group consisting of 1 to 4 rings, optionally fused, and optionally substituted by $C_{1-4}$ alkyl, $C_{2-4}$ alkenyl, $C_{5-7}$ cycloalkyl, $C_{5-7}$ cycloalkenyl, halo, preferably fluoro or chloro, $C_{1-4}$ aldehyde, —$NR^4{}_q$ and like groups where $R^4$ is H or organyl groups, preferably H, $C_{1-8}$ alkyl, $C_{2-8}$ alkenyl, $C_{4-8}$ cycloalkyl, $C_{4-8}$ cycloalkenyl, or $C_{6-10}$ aryl; and q is 2 or 3, with the proviso that when q is 3, the group bears a positive formal charge. It should be noted that unsaturated groups such as alkenyl and cycloalkenyl include multiply unsaturated groups such as alkadienyl and cycloalkadienyl. Alkyl and cycloalkyl groups herein also include aryl-substituted alkyl and cycloalkyl groups, while aryl groups also include alkyl and cycloalkyl-substituted aryl groups. In a variation, A is optionally substituted thienyl, pyridinyl, phenyl, biphenyl, or naphthyl, more preferably phenyl and biphenyl, quinolinyl, and isoquinolinyl. Preferred substituents include $C_{1-4}$ alkyl, —CN, halo, $C_{1-4}$ lower alkoxyl, and $NH_2SO_2R^3$, $CF_3$, arylsulfonyl, arylsulfonamide, etc., more preferably o-$OCH_3$, 2,3-dichloro, and p-$NHSO_2CH_3$;

p is an integer from 1 to 6; and $Z_m$ is absent or a divalent linking moiety in which Z is repeated m times. Examples of Z include —$CH_2$—, —CO— where m is an integer from 0 to 5. In another variation, m is an integer from 0 to 2.

In a variation of the present embodiment, a compound having formula II for treating neurodegenerative and other related CNS diseases is provided:

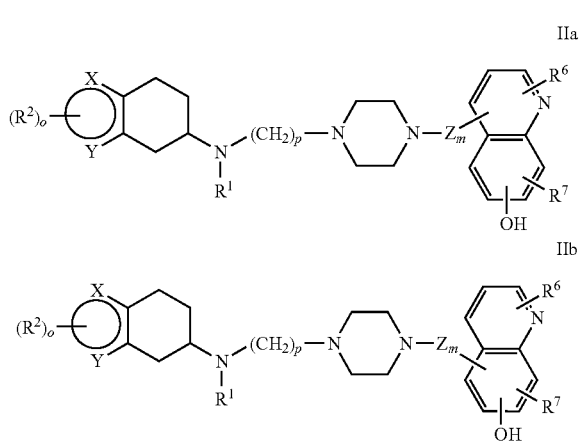

wherein $R^1$, $R^2$, o, p, Z, m, and

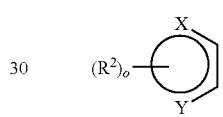

are as set forth above in connection with the description of Formula I. $R^6$ and $R^7$ are Cl, F, OH, H, $C_{1-8}$ alkyl, $C_{2-8}$ alkenyl, $C_{4-8}$ cycloalkyl, $C_{4-8}$ cycloalkenyl, $C_{6-10}$ aryl.

In still another variation of the present embodiment, a compound having formula IIIa or formula IIIb for treating neurodegenerative and related CNS diseases is provided:

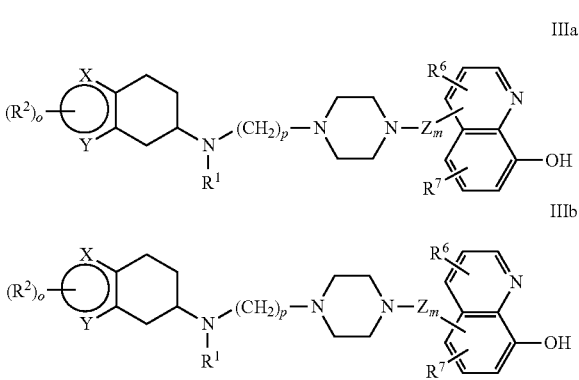

wherein $R^1$, $R^2$, o, p, Z, m, and are as set forth above in connection with the description of Formula I. $R^6$ and $R^7$ are Cl, F, OH, H, $C_{1-8}$ alkyl, $C_{2-8}$ alkenyl, $C_{4-8}$ cycloalkyl, $C_{4-8}$ cycloalkenyl, $C_{6-10}$ aryl.

In still another variation of the present embodiment, compounds having formulae IVa and IVb for treating a neurodegenerative disease is provided:

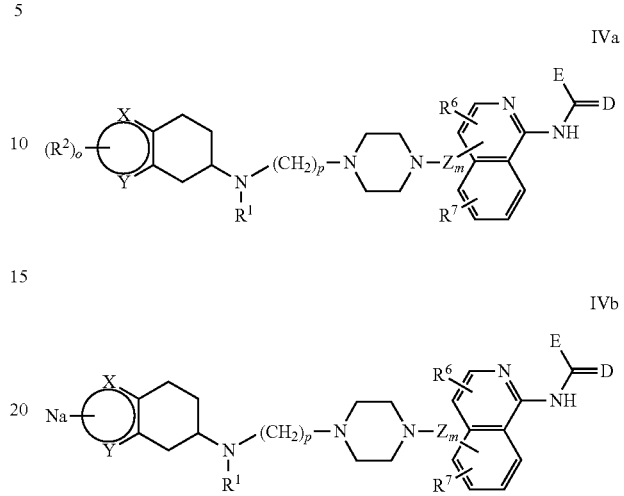

wherein $R^1$, $R^2$, o, p, Z, m, and are as set forth above in connection with the description of Formula I. $R^6$ and $R^7$ are Cl, F, H, $C_{1-8}$ alkyl, $C_{2-8}$ alkenyl, $C_{4-8}$ cycloalkyl, $C_{4-8}$ cycloalkenyl, $C_{6-10}$ aryl. D is S, O or —NR where R is H, alkyl, or aryl. E is SR, OR or —$NR_2$ where R is H, alkyl, or aryl.

In still another variation of the present embodiment, compounds having formulae Va and Vb for treating a neurodegenerative disease is provided:

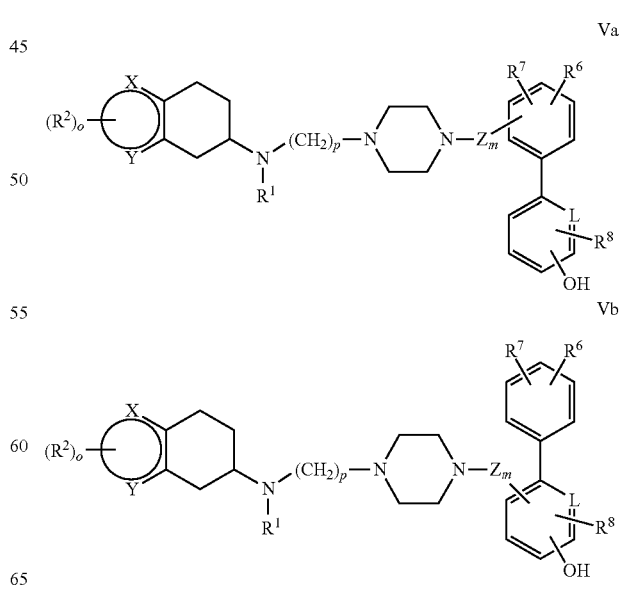

wherein $R^1$, $R^2$, o, p, Z, m, and

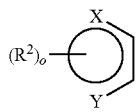

are as set forth above in connection with the description of Formula I. $R^6$, $R^7$, and $R^8$ are Cl, F, OH, H, $C_{1-8}$ alkyl, $C_{2-8}$ alkenyl, $C_{4-8}$ cycloalkyl, $C_{4-8}$ cycloalkenyl, $C_{6-10}$ aryl; L is N or CH.

In still another variation of the present invention, a compound having formulae VIa and VIb for treating a neurodegenerative disease is provided:

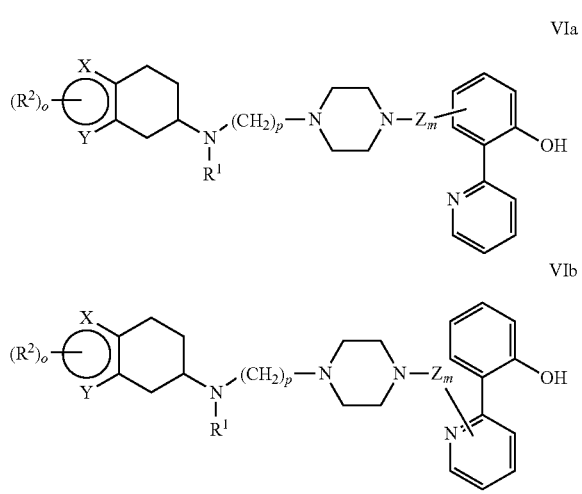

wherein $R^1$, $R^2$, o, p, Z, m, and

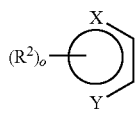

are as set forth above in connection with the description of Formula I. In a variation, the fused ring system at the right of Formulae VIa and VIb are substituted with $R^6$ and $R^7$ as set forth above where $R^6$ and $R^7$ are Cl, F, OH, H, $C_{1-8}$ alkyl, $C_{2-8}$ alkenyl, $C_{4-8}$ cycloalkyl, $C_{4-8}$ cycloalkenyl, $C_{6-10}$ aryl.

In still another variation of the present invention, a compound having formulae VII for treating a neurodegenerative disease is provided:

VII

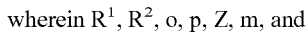

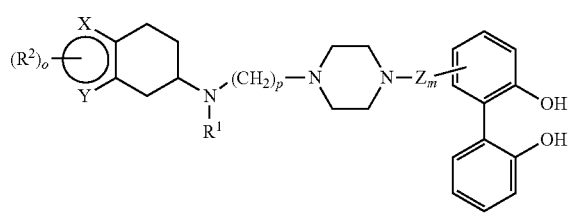

wherein $R^1$, $R^2$, o, p, Z, m, and

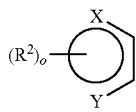

are as set forth above in connection with the description of Formula I. In a variation, the fused ring system at the right of Formula VII is substituted with $R^6$ and $R^7$ as set forth above where $R^6$ and $R^7$ are Cl, F, OH, H, $C_{1-8}$ alkyl, $C_{2-8}$ alkenyl, $C_{4-8}$ cycloalkyl, $C_{4-8}$ cycloalkenyl, $C_{6-10}$ aryl.

Figure 1C:
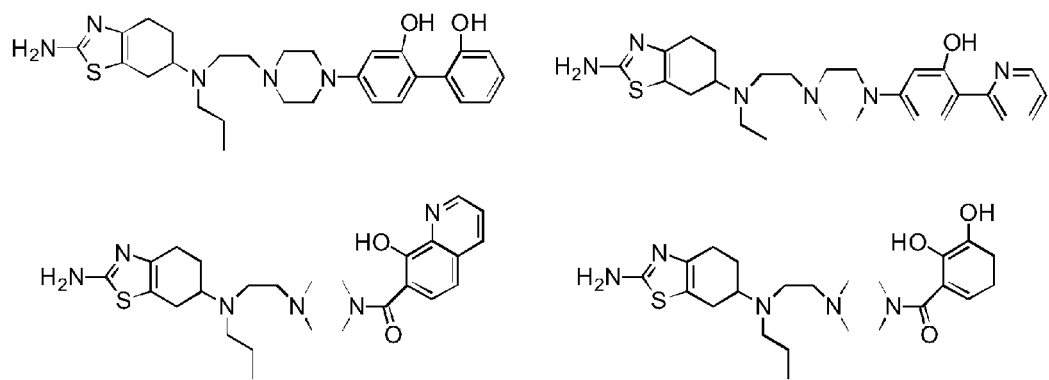

FIGS. 1A, 1B, and 1C provide specific compounds with structures encompassed by one or more of Formulae I to VII.

In another embodiment of the present invention, a compound having formulae VIIIa and VIIIb for treating a neurodegenerative disease is provided:

VIIIa

VIIIb

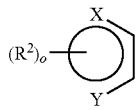

wherein $R^1$, $R^2$, o, p, Z, m, and are the same as set forth above in connection with the description of Formula I. Q is N—H, O, S or N—R where R is hydrogen, aryl or alkyl. In a variation, the fused ring system at the right of Formulae VIIIa and VIIIb are substituted with $R^6$ and $R^7$ as set forth above where $R^6$ and $R^7$ are Cl, F, OH, H, $C_{1-8}$ alkyl, $C_{2-8}$ alkenyl, $C_{4-8}$ cycloalkyl, $C_{4-8}$ cycloalkenyl, $C_{6-10}$ aryl.

Figure 2:
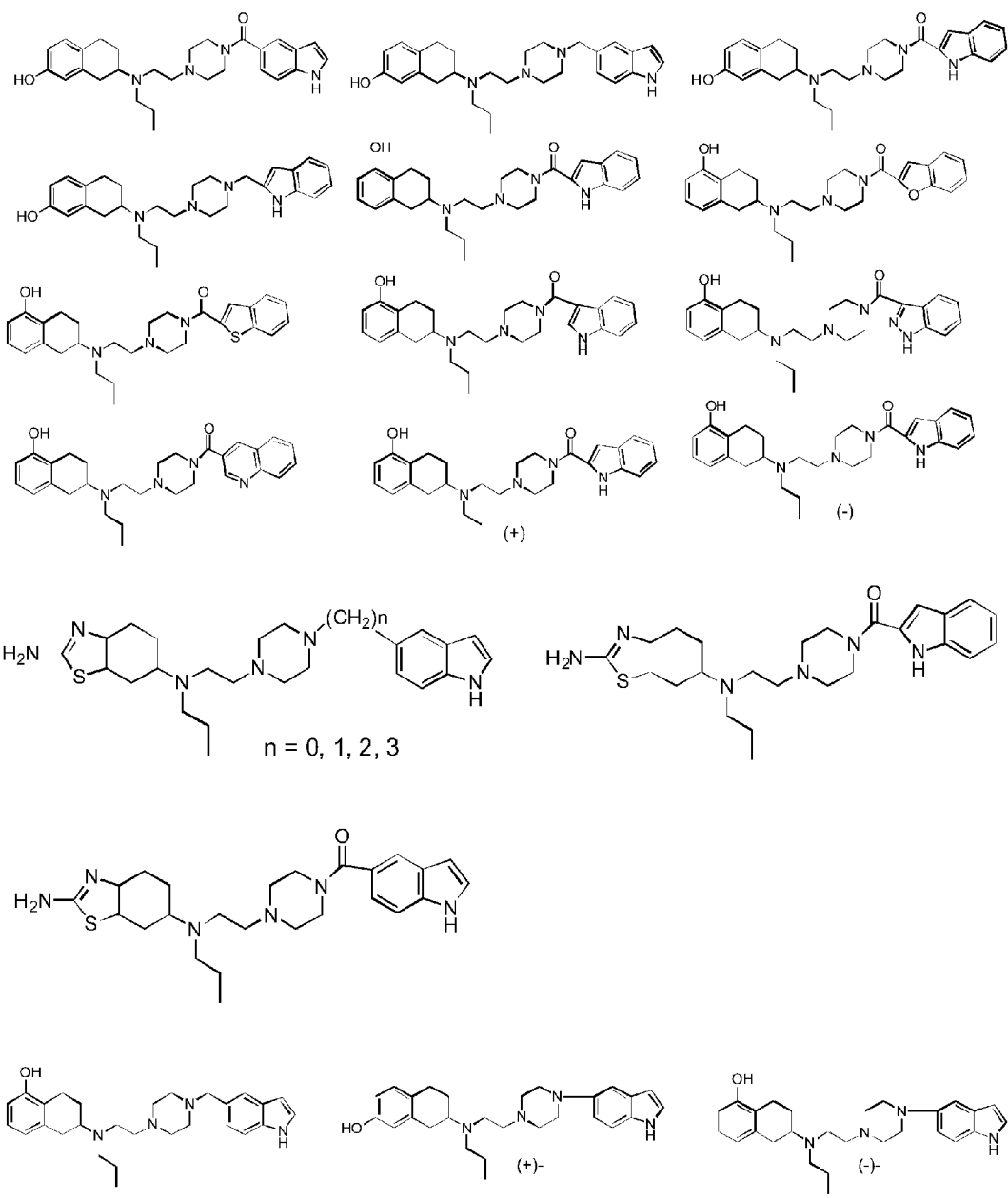
FIG. 2 provides specific compounds of another embodiment of the present invention.

FIG. 2 provides specific compounds with structures encompassed by one or more of Formulae VIIIa and VIIIb.

The compounds set forth herein may be used per se or as pharmaceutically acceptable derivatives. The latter term includes salts, esters, and other derivatives generally considered acceptable by pharmaceutical standards. Useful derivatives, for example, include salts of organic and inorganic acids such as sulfates, phosphates, hydrohalide salts, carboxylate salts, etc., as well as esters of carboxylic acid or hydroxyl substituents, ethers of hydroxyl substituents, amides of amino substituents, as well as carbamates, ureas, etc. Synthesis of these derivatives is conventional, and well known to those skilled in pharmaceutical chemistry. For example, compounds bearing hydroxyl groups may be converted to esters by customary techniques of organic chemistry, such as reaction with an acyl halide, carboxylic acid anhydride, or by esterification with an acid while removing byproduct water. In some cases, derivation may be desired to facilitate compounding of the pharmaceutical into an acceptable form such as tablets, powder, aqueous dispersion, capsule, etc., or may be useful in assisting bioavailability of the drug following administration, for example by rendering the compound more or less soluble. In many cases, such as, for example, esters, ureas, carbamates, ethers, etc., the derivative may act as "prodrug," which liberates the active form by biological transformation, i.e., by enzymatic hydrolysis of an ester functionality, as is well known to the pharmaceutical chemist.

One or more of the embodiments and variations set forth above provide a hybrid template having a metal binding 8-hydroxy quinoline moiety or other suitable moieties combined with a previously developed piperazine ring moiety. Although the operation of the present invention is not limited by any particular mode of operation, it is believed that the hybrid template is able to retain affinity for dopamine receptors while the hydroxy quinoline moiety, being located at a distal position with respect to the agonist binding moiety, will participate in binding to iron in the brain without having an impact on agonist activity. In this regard, extensive data is available on metal binding capacity of 8-hydroxy quinoline and its derivatives. In at least one variation, compounds having dopamine D2/D3 agonist activity along with a capacity to chelate with iron will not only alleviate motor dysfunction in PD but will also reduce oxidative stress leading to greater survival of dopamine neurons. Therefore, this approach might provide more desirable therapeutic agents which may slow or even halt the progression of dopamine cell death in PD along with restoration of motor dysfunction.

Typical dosages for mammalian species may vary from 0.001 mg/Kg of body weight to about 100 mg/Kg of body weight, preferably 0.01 mg/Kg to 5 mg/Kg. The actual amount will vary depending upon the particular CNS activity desired to be altered, and the desired degree of alteration. The upper limits may, as with virtually all drugs, be limited by toxicity of the drug or its metabolites, or by the presence of unwanted side effects. The drugs may be administered in any form, but preferably in the form of tablets or capsules with appropriate excipients. Dosages, forms of administration, etc., can be readily determined by those skilled in the art.

Guidelines to the effective dosages in mammalian species are provided by the many known drugs commercially available which bind to CNS monoamine receptor sites, and by comparing the binding affinities of these pharmaceuticals with the target compounds of the subject invention by in vivo and in vitro studies. In addition to the utility of the subject invention compounds in treatment of diseases such as Parkinson's disease, schizophrenia, treatment for addiction such as cocaine addiction, and the like, the subject invention compounds are also useful, particularly in their radio labeled form, for clinical studies directed to distribution of monoamine receptor sites in the brain and the effect which compounds such as cocaine have on these sites.

EXPERIMENTAL

1. Compounds Having Formulae I to VII

Figure 3A:
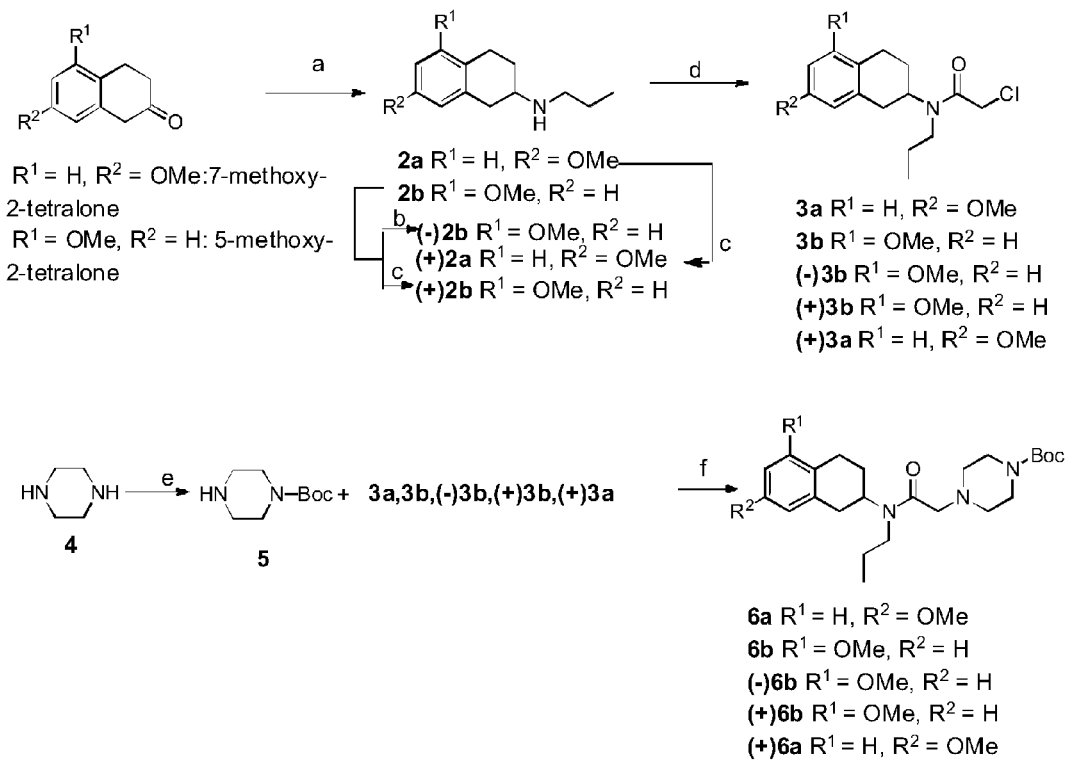
FIGS. 3A and 3B provide part of a synthetic scheme for preparing compounds of an embodiment of the present invention.
Figure 3B:
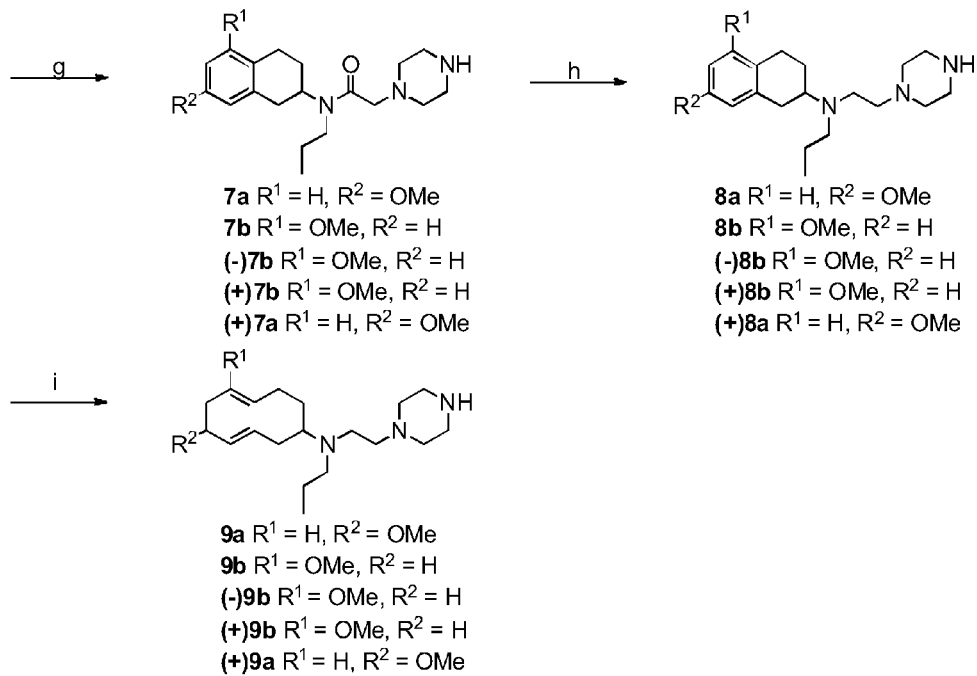

Scheme 1 (FIGS. 3A and 3B) outlines the syntheses of 9a, 9b and their enantiomers. The starting materials for these compounds were appropriately substituted 7- and 5-methoxy-2-tetralones. These were condensed with propyl amine under standard reductive amination condition to give secondary amines 2a-b. Enantiomerically pure amines were made by using a synthetic chiral resolving agent as described previously by us. N-alkylation of amines using chloroacetyl chloride in presence of triethyl amine produced intermediate α-chloro amides 3a, 3b and their enantiomers. N-acylation with mono Boc-protected piperazine gave amides, which were then reduced by lithium aluminum hydride followed by deprotection with trifluoroacetic acid yielded 8. Demethylation in the presence of boron tribromide afforded phenols 9a, 9b and their enantiomers.

Scheme 2 (FIG. 4) depicts the synthesis of two final compounds 12a and 12b. Here the starting material is 8-hydroxyquinoline which was converted into 5-methylenechloride derivative 11 by treating it with formaldehyde and hydrogen chloride gas. N-alkylation of 11 with two different piperazine fragments 9a and 9b provided two final compounds 12a and 12b which were then purified by recrystallization of their hydrochloride salts from ethanol.

Figure 5:
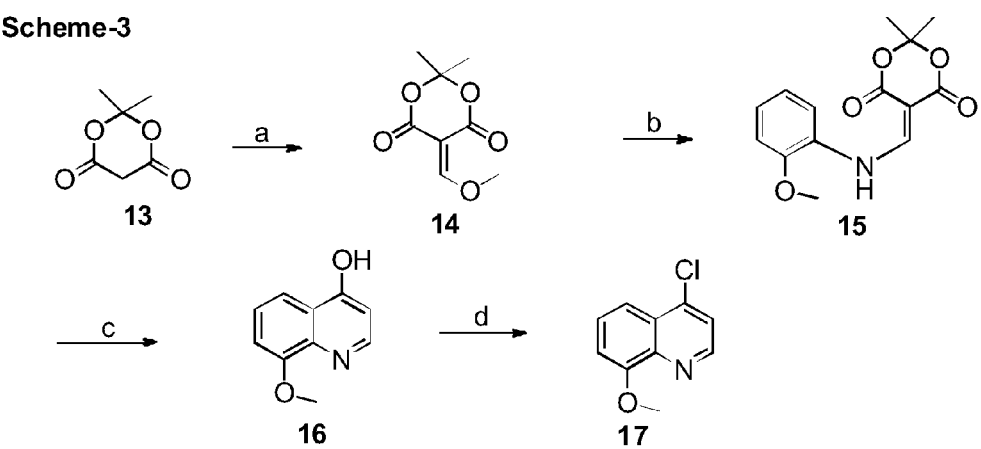
FIG. 5 provides part of a synthetic scheme for preparing compounds of an embodiment of the present invention.

Scheme 3 (FIG. 5) describes the syntheses of chloride derivative of quinoline component 17. Most of the current methods for synthesis of quinoline rings are variations of the Skraup method in which an aniline derivative is heated with glycerol and an acid catalyst to form a stable intermediate that undergoes cyclization after a high-temperature Friedel-Crafts acylation. We used a modified method that uses methoxymethylene Meldrum's acid. This has the advantage of giving the same products in two steps rather than four steps. The first step in this sequence is the condensation of O-anisidine with Meldrum's acid and trimethyl-orthoformate. The Meldrum's acid was refluxed in trimethyl-ortho-formate to form methoxymethylene Meldrum's acid 14 in situ. Addition of anisidine into the reaction mixture initiated addition-elimination reaction with the methoxy-methylene moiety to afford an ene-amine intermediate 15 for cyclization. Addition of an equal volume of DMF to the reaction with increase of reaction temperature overcame sluggishness of the reaction to facilitate the formation of 15. The ene-amine intermediate was then refluxed at 300° C. in phenyl ether as solvent for 15 min. The cyclized product was isolated by cooling and subsequent precipitation by mixing with hexane followed by filtration, washing with additional hexane, and drying. This compound (16) was then purified by column chromatography. The 4-hydroxy-8-methoxy quinoline (16) was dissolved in phosphorus oxychloride and heated to reflux for 2 h to give the desired 4-chloroquinoline derivative.

Scheme 4 (FIG. 6) describes the syntheses of final compounds 19a, 19b and their enantiomers. Intermediate 9a, 9b and their enantiomers were condensed with quinoline component (17) under refluxing condition in 2-propanol in presence of diisopropylethylamine as base gave 18 which were then demethylated under refluxing condition with 48% aqueous HBr. The final compounds 19a, 19b and their enantiomers were purified by recrystalization of their HCl salt from ethanol.

The compounds of Formulae I to VII are multifunctional ligands that simultaneously target dopamine D2/D3 receptors as agonist while binding iron to reduce oxidative stress, an hydroxy quinoline moiety was introduced in our hybrid template for D2/D3 receptors.

Figure 4:
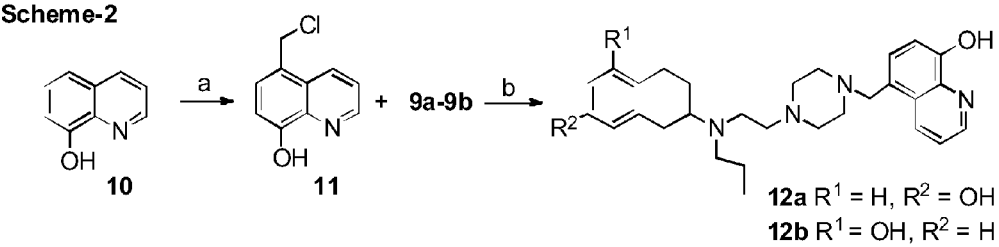
FIG. 4 provides part of a synthetic scheme for preparing compounds of an embodiment of the present invention.
Figure 7B:
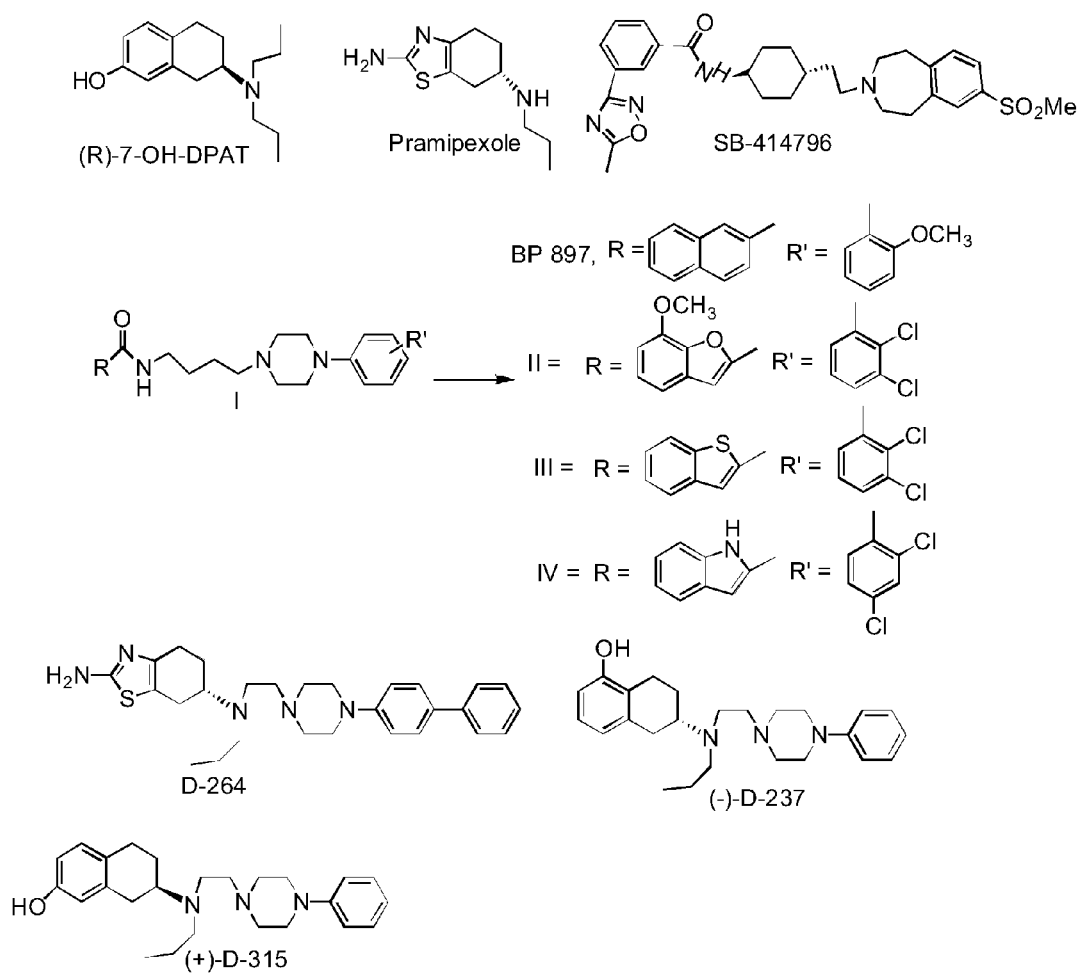
FIG. 7B provides structure of compounds for comparison purposes.

With reference to FIG. 4, compounds 12a and 12b were synthesized. In these two compounds, a 5-methylquinoline-8-ol moiety was attached to the piperazine ring. Both compounds exhibited low nanomolar potency for D3 receptor (5.57 and 3.71 nM for 12a and 12b, respectively, FIG. 7A (Table 1). FIG. 7B provides comparative compounds. Compound 12b was twice as potent at D2 receptors compared to 12a (41 vs. 86 nM for 12b and 12a, respectively). These results indicated that the 5-methylquinoline-8-ol moiety was well tolerated by D2/D3 receptors.

Figure 6:
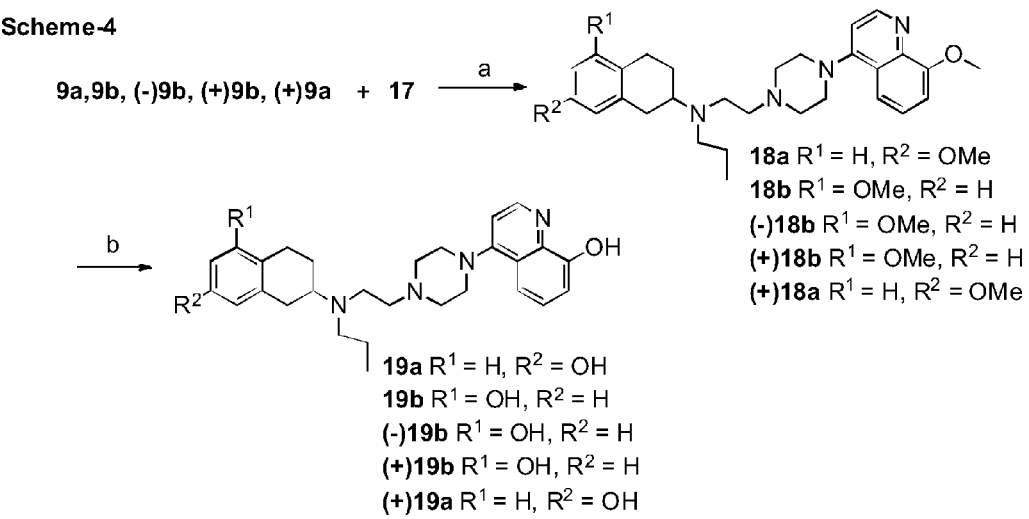
FIG. 6 provides part of a synthetic scheme for preparing compounds of an embodiment of the present invention.

With reference to FIG. 6, an 8-hydroxy quinoline moiety is directly attached to the piperazine ring. The two racemic compounds, 19a and 19b, designed based on 5-hydroxy and 7-hydroxy templates, exhibited high affinity for both D2 and D3 receptors (Ki; 15.9 and 0.81 nM for 19a and 13.8 and 1.35 nM for 19b, respectively). Both these compounds showed moderate preferential affinity at D3 receptor compared to the D2 receptor (D2/D3; 19.62 and 10.22 for 19a and 19b, respectively). These results indicated that introduction of the 8-hydroxy quinoline moiety retained high affinity activity at both D2 and D3 receptors. In our next effort to prepare enantiomerically pure compounds of racemic 19b, compounds (−)19b and (+)19b were synthesized. As expected from our previous data from 5-hydroxy series hybrid compounds, higher affinity at both D2 and D3 was observed in (−)-19b compared to (+)-19b (Ki; 3.75 and 1.28 nM for (−)19b and 20.7 and 7.73 nM for (+)19b, respectively). Based on our results from activity of enantiomers of 7-hydroxy series hybrid compounds, we selectively synthesized (+)-19a. This compound like its 5-hydroxy counterpart exhibited high affinity for D2 and D3 receptors (Ki; 4.55 and 1.27 nM, respectively, FIG. 7 (Table 1)).

Following binding analysis, selected compounds (−)19b and (+)19a were subjected to the [35S]GTPγS functional assay for D2 and D3 receptors and compared with the full agonists dopamine and ropinirole. The assays were carried out with the cloned human D2 and D3 receptors expressed in CHO cells. The results indicate that both compounds are quite active in stimulating both D2 and D3 receptors with similar potency: No appreciable selectivity was displayed by these compounds. Both showed full or near-complete agonism at D2 and D3 when compared against the reference substance dopamine, as did ropinirole (FIG. 8 (Table 2)). Thus, our binding and functional assay results indicated that introduction of an 8-hydroxy quinoline moiety retained not only high affinity for binding to D2/D3 receptors but also potent agonist activity at both receptors. Compound (−)-19b was selected for animal study as 5-hydroxy aminotetralin derived compound e.g. 1a, was previously shown to exhibit potent in vivo activity with long duration of action.

pH-Dependent Complexation Studies with Iron (III).

Figure 9:
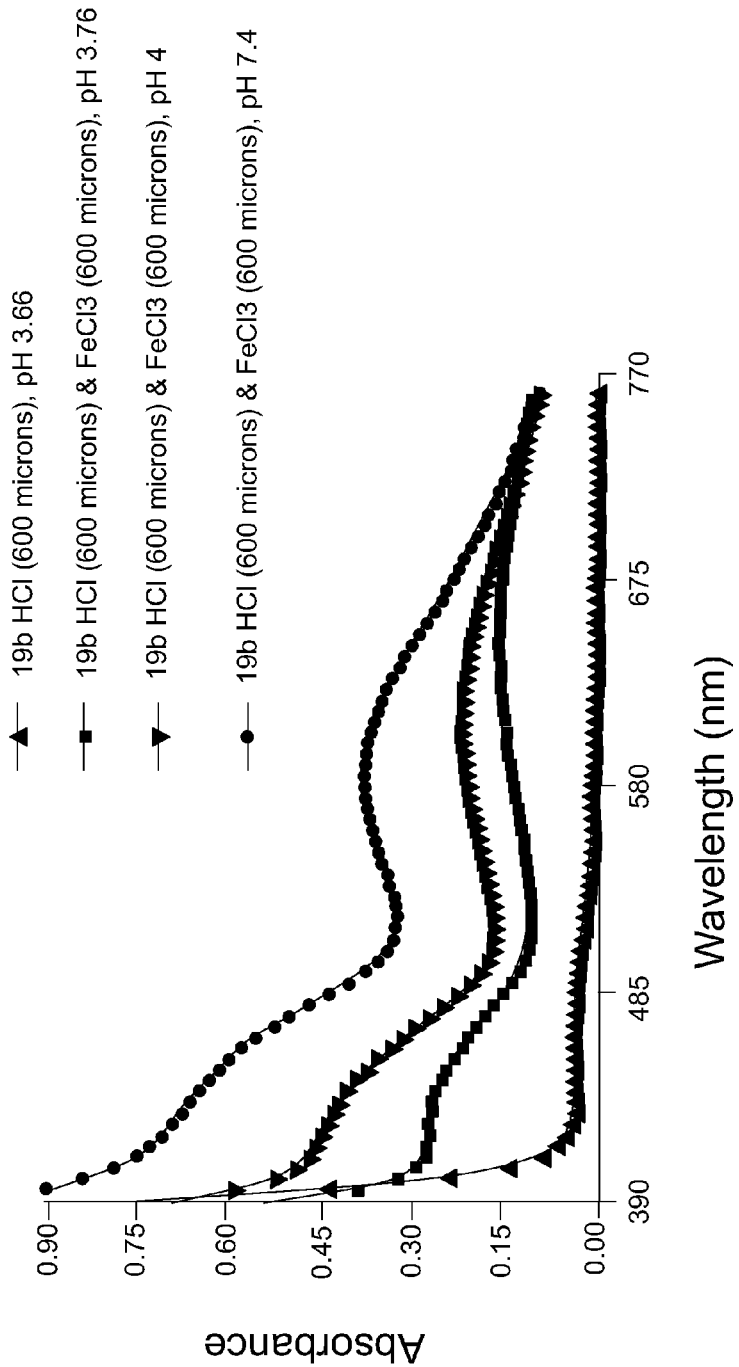
FIG. 9 provides UV-visible absorption spectra of complex formation between racemic 19b (0.6 mM) and $FeCl_3$ in water at various pH.

Equimolar amounts (600 μM) of 19b and FeCl$_3$ were mixed together and complex formation was followed by UV absorption scanned from 200-800 nm at different pHs. It is evident from the plot (FIG. 9) that 19b in presence of ferric chloride produced distinctly different UV absorption profiles compared to UV absorption of the compound 19b alone in the absence of iron chloride. This is indicative of a complex formation. In general a shift in λmax to the left takes place with increase of pH in the solution. Thus, at pH 3.76 the λmax was 647 nm (ε=567 M$^{-1}$ cm$^{-1}$) and at pH 7.4 λmax it was 580 nm (ε=1300 M$^{-1}$ cm$^{-1}$). This observation agrees with the reported data on complexation of 8-hydroxy related compound with iron. Also the absorption spectra of the solution at pH 7.4 exhibited higher intensity at 580 nm than the spectra at lower pHs. This pH-dependent Fe(III)-19b complexation study indicated the amount of complex formation was favored by neutral pH. Since brain maintains physiologically a neutral pH, compound 19b might be a potential candidate to chelate iron in the PD brain.

Evaluation of Fe (II) Chelating Potency of 19b in Ferrozine Assay

Figure 10:
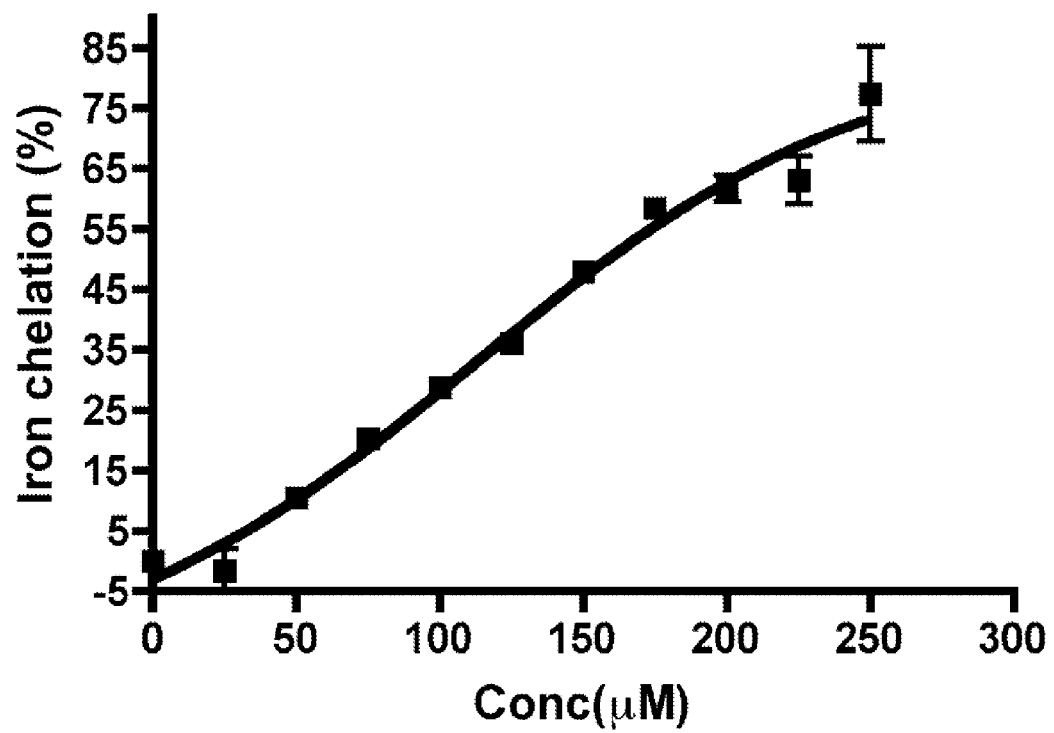
FIG. 10 provides chelating potency of 19b via displacement of ferrozine complexed to $FeSO_4$ and is expressed as percent of control. Each point represents value from experiment done in triplicate and is expressed as mean±SEM.

We performed an in vitro biochemical iron binding assay, known as the Ferrozine Assay, to determine the chelation potency of molecule 19b. We envisioned that potent iron binding compound will arrest iron in the PD brain from taking part in the Fenton reaction and thereby reduce the formation of hydroxyl radical and oxidative stress. Chelating potency of 19b was evaluated by Ferrozine assay method which is a colorimetric assay. Ferrozine is known to bind to iron (II) and forms a characteristics color upon complexation with Fe(II) which can be quantitated at 562 nm. In this assay displacement of ferrozine from its complexation to Fe (II) by 19b in a concentration dependent manner was measured by absorption at 562 nm. It is evident from FIG. 10 that at higher concentration of 19b complexation almost exclusively takes place with Fe (II). It has been shown in the past that ligands such as DFO complex to Fe (II) to undergo aerobic oxidation to Fe (III). Thus, this process of chelation potentially measures complexation to both Fe (II) and Fe(III). The chelating effect is expressed as a percent of control [80 μM ferrozine, 20 μM ferrous ammonium sulfate in pH 6.9 ammonium acetate buffer (5%)] by using the known equation (shown in the experimental section). Inhibition constant (IC$_{50}$) of this compound was calculated to be 155.56±0.73 μM (n=3).

Mass Spectroscopy Evidence of Complex Formation

Figure 11:
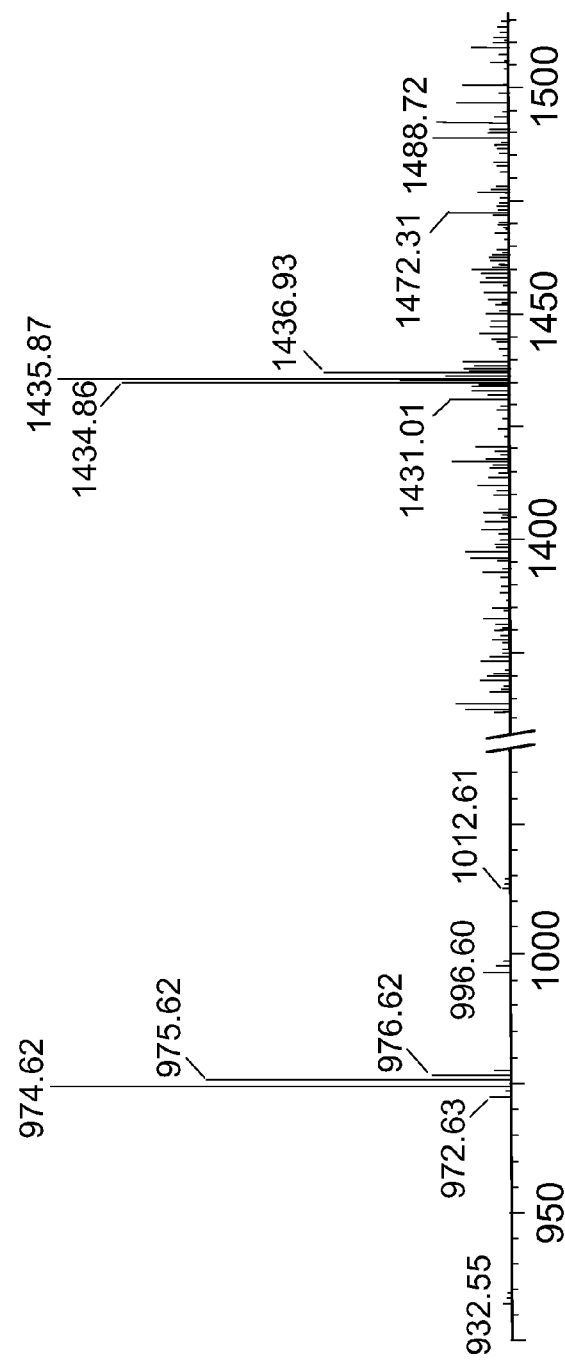
FIG. 11 provides molecular ion peaks of complexes formed from racemic 19b and $FeCl_3$ at pH 7.4. Peaks at m/z 975 and 1434 correspond to 19b-Fe complex stoichiometry 2:1 and 3:1.

In an effort to demonstrate further formation of iron complexes, we carried out mass spectral analysis of 19b and FeCl$_3$ solutions used in UV analysis above to detect any molecular ion peak corresponding to complex molecular ions. As shown in FIG. 11, we indeed observed molecular ion peaks corresponding to L$_2$-Fe$^{3+}$ (M/z: 975) and L$_3$-Fe$^{3+}$ (M/z: 1434, 1435) complexes formation (L=ligand molecule). Thus, these results give clear evidence of formation of iron complexes with compound 19b.

Deoxyribose Antioxidant Assay

Figure 12:
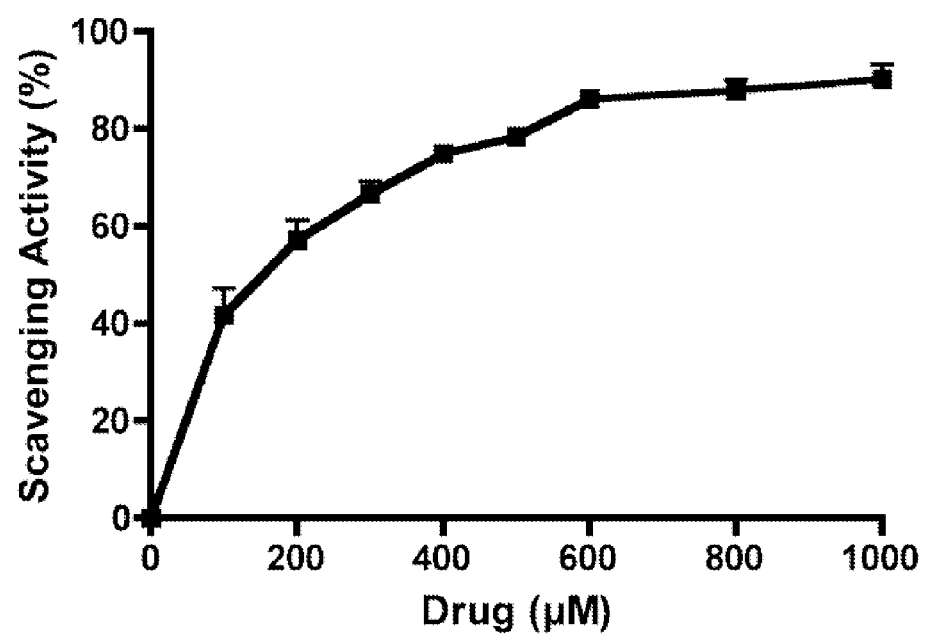
FIG. 12 provides hydroxyl radical scavenging capacity of 19b in deoxyribose-containing solution. Values are reported as percentage versus a blank ±SD.

Antioxidant activity of 19b was analyzed by this assay. This is a test tube assay which measures hydroxyl radical scavenging capacity of a test compound by competing with deoxyribose. In this assay, hydroxyl radical is generated by reaction of iron (Fe$^{3+}$)-EDTA complex with H$_2$O$_2$ (by Fenton reaction) in presence of ascorbic acid which then react with deoxyribose to form smaller molecular fragment which upon heating with 2-thiobarbituric acid under acid conditions yields a pink color dye. Test compound (s) with potential radical scavenging capacity will compete with deoxyribose for hydroxyl radical generated by Fenton reaction. Thus, formation of fragment from deoxyribose and the pink color formation will be dictated by the capacity of a test compound to quench hydroxyl radical. This is a colorimetric assay and the absorbance is measured at 532 nm. Hydroxyl radical formation by Fenton reaction in the substantia nigral (SN) region of the PD brain might take place as H$_2$O$_2$ is generated in SN by dopamine metabolism and SN area is rich in iron in case of PD. It is apparent from FIG. 12 that compound 19b dose dependently inhibited decomposition of deoxyribose by OH$^-$ with the highest dose exhibiting 80% scavenging activity with respect to control containing deoxyribose alone.

Reversal of Reserpine-Induced Hypolocomotion in Rats by (−)19b and Ropinirole

Figure 13:
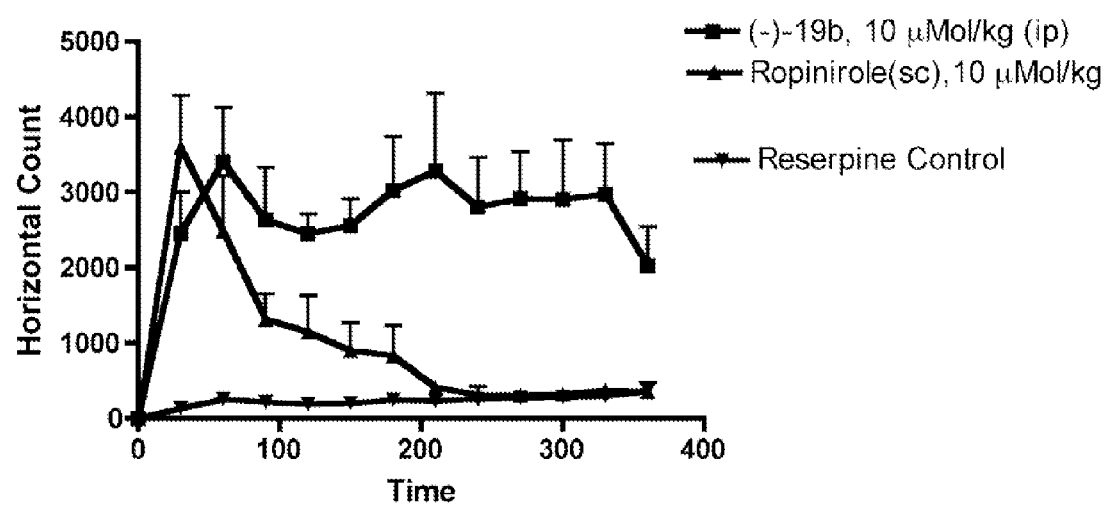
FIG. 13 provides plots showing the effect of different drugs upon reserpine (5.0 mg/Kg, s.c.)-induced hypolocomotion in rats. Data are means±S.E.M, n=4 per value. Horizontal activity was measured as described under materials and methods. Panel A is the representation of horizontal locomotor activity at discrete 30-min intervals after the administration of (−)19b (i.p.) and ropinirole (s.c.) at the dose of 10 μMol/kg compared to control rats in 18 h post reserpine treatment. One way ANOVA analysis demonstrates significant effect among treatments: F (3,95)=31.36 (P<0.0001). Dunnett's analysis following ANOVA showed that the effects of (−)19b (P<0.01) and ropinirole (P<0.05) were significantly different compared to reserpine control.

Reserpine induces depletion of catecholamines in nerve terminals resulting in a cataleptic condition in rats, which is a well established animal model for PD. Significant reduction of locomotion of the rats was observed 18 h after the administration of reserpine (5 mg/kg, s.c.) which indicated the development of akinesia in rats. Compound (−)19b was highly efficacious in reversing the locomotor activity of reserpinized rats (FIG. 13). The locomotor activity of (−)19b at the end of 6 h remained very high. The reference drug ropinirole on the other hand exhibited much shorter duration of action compared to (−)19b. Compound (−) 19b at a dose of 10 μmol/kg i.p. not only reversed reserpine induced hypokinesia to the normal level of locomotion found in control animals (vehicle treated reserpinized rats), but also demonstrated significant enhancement of locomotion for the entire duration of study. The mechanism of the locomotor stimulation in the reserpine model is likely to be mediated by postsynaptic D2/D3 receptor activation by (−)19b. Thus, the results suggest that the compound is a potent agonist, which crosses the blood brain barrier effectively and possesses excellent in vivo stability.

Figure 14:
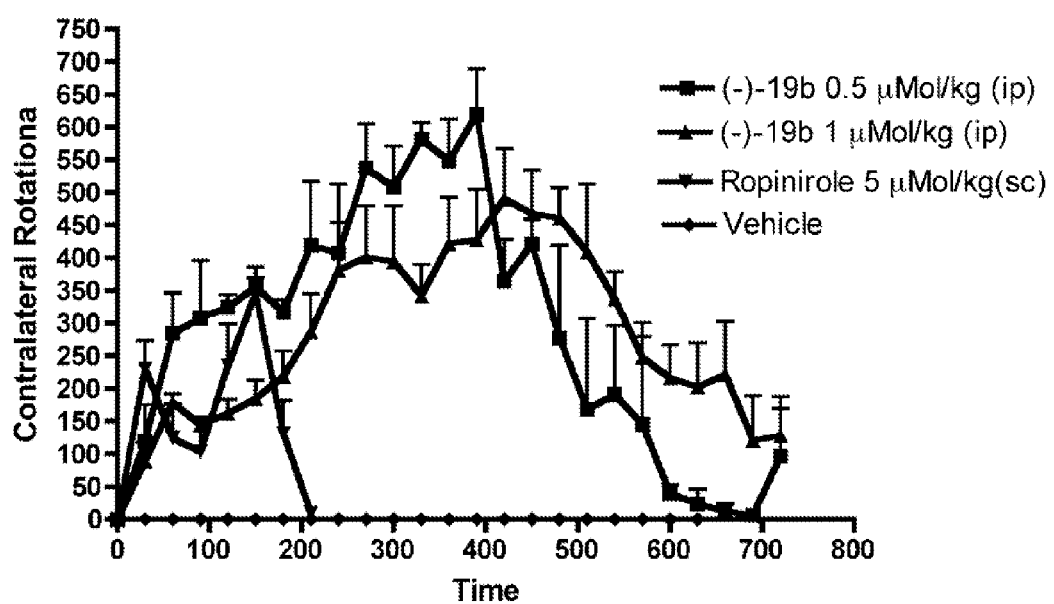
FIG. 14 provides plots showing the effect on turning behavior of two different doses of (−)19b (i.p.) and vehicle in lesioned rats studied for maximum 12 h. Each point is the mean±SEM of 3-4 rats. The drugs were administered i.p. One way ANOVA analysis demonstrates significant effect among treatments: F (4,95)=21.12 (P<0.0001). Dunnett's analysis showed that the effect of (−)19b on rotations at two doses was significantly different compared to vehicle (P<0.01) and the effect of ropinirole was significant compared to vehicle (p<0.05)

In Vivo Effect of (−)-19b in 6-OHDA Lesioned Rats:

Compound (−)19b was tested in vivo in rats carrying an unilateral lesion in the medial forebrain bundle induced by application of the neurotoxin 6-hydroxydopamine (6-OHDA). Development of supersensitivity of dopamine receptors takes place resulting from destruction of dopamine neurons in these surgically modified rats. When these rats are challenged with direct acting dopamine agonists, they produced contralateral rotations away from the lesioned side. This rat model is considered to be one of the standard models for preclinical screening of drugs for possible antiparkinsonian property. Compound (−)19b was highly efficacious in producing large number of rotations at a smaller dose of 0.5 µMol/kg (0.3 mg/kg) and the activity lasted more than 11 h (Number of rotation=7081). At a higher dose of 1 µMol/kg (0.61 mg/kg), the rotational activity produced by (−)-19b was initially less compared to the lowest dose (0.5 µMol/kg) but the activities increased gradually and remained high at the termination of the experiments after 11 h (FIG. 14). On the other hand, the reference ropinirole at 5 µMol/kg produced much less rotations with shorter duration of action. The efficacy of this compound in producing rotations indicated its excellent brain penetration under i.p. administration condition.

In this initial report, we describe the development of unique multifunctional dopamine D2/D3 agonist compounds with a capacity to chelate with iron ($Fe^{2+}/Fe^{3+}$). Our design of the preliminary compounds originated from observations collected in our earlier SAR studies, which demonstrated existence of a flexible binding pocket for substitutions on the piperazine ring located in a distal position with respect to the aminotetralin moiety. Thereby, a known iron chelating moiety 8-hydroxy quinoline was introduced in the hybrid structure, which resulted in the development of first-generation multifunctional molecules. Such molecules are not only expected to relieve motor dysfunction in PD but also will have potential to reduce oxidative stress in the PD brain by chelating with iron. Two lead molecules (−)19b and (+)19a identified from the binding study were subjected to the GTPgS functional assay which demonstrated their potent agonist property. Complexation studies with 19b demonstrated chelation with iron efficiently. Furthermore, the deoxyribose assay with 19b demonstrated potent antioxidant activity in these compounds. One of the lead molecules was then tested in PD animal models. Compound (−)19b not only reversed the reserpine-induced hypolocomotion in rats but also maintained a significant level of higher activity throughout the study session. In this regard efficacy of (−)19b at an equivalent dose was far greater than the standard reference ropinirole, which exhibited a shorter duration of action. In rotational experiments with 6-OH-DOPA-lesioned rats, two doses of (−)19b were efficacious in producing extensive rotational activity. Compound (−)19b will be subjected to neuroprotection study to evaluate its potential in protecting against cell death in near future.

Analytical silica gel-coated TLC plates (Silica Gel 60 $F_{254}$) were purchased from EM Science and were visualized with UV light or by treatment with phosphomolybdic acid (PMA). Flash chromatography was carried out on Baker Silica Gel 40 mM. 1H NMR spectra were routinely obtained on GE-300 MHz and Varian 400 MHz FT NMR. The NMR solvent used was either $CDCl_3$ or $CD_3OD$ or $DMSO-d_6$ as indicated. TMS was used as an internal standard. Elemental analyses were performed by Atlantic Microlab, Inc and were within ±0.4% of the theoretical value.

Procedure A. Preparation of 7-Methoxy-1,2,3,4-tetrahydro-naphthalen-2-yl)-propyl-amine (2a)

7-Methoxy-2-tetralone (10 g, 56.75 mmol) and acetic acid (13.5 ml, 226.9 mmol) were dissolved in dichloroethane (150 ml) and cooled to 0° C. n-propyl amine (11.7 ml, 141.87 mmol) was added and the mixture stirred under a $N_2$ atmosphere for 30 min. $NaCNBH_3$ (8.915 g, 141.87 mmol) in anhydrous MeOH (15 ml) was then added to the mixture and allowed to stir overnight at ambient temperature. The volatiles were then evaporated and saturated $NaHCO_3$ solution was added. It was then extracted with dichloromethane, dried over $Na_2SO_4$, filtered, and concentrated. The crude residue was then taken up in EtOAc, at which time ethereal HCl was added, and the crude salt was filtered and dried over vacuum oven. The crude salt was then recrystalized in ethanol to yield 9.5 g (65%) white solid and used in the subsequent transformations. $^1H$ NMR (free base) (400 MHz, $CDCl_3$) δ ppm 0.91-0.95 (t, 3H, J=7.6 Hz), 1.38 (bs, 1H), 1.48-1.60 (m, 3H), 2.04-2.09 (m, 1H), 2.67-2.71 (t, 3H, J=7.6 Hz), 2.88-2.92 (m, 2H), 2.97-3.04 (m, 1H), 3.81 (s, 3H), 6.60-6.62 (dd, 1H, J1=1.6 Hz, J2=4.2 Hz), 6.65-6.78 (m, 1H), 6.95-6.98 (d, 1H, J=8.8 Hz).

(5-Methoxy-1,2,3,4-tetrahydro-naphthalen-2-yl)-propyl-amine (2b)

Compound 2b was prepared following procedure A using 5-methoxy 2-tetralone and purified by recrystalization of its hydrochloride salt from ethanol to get white salt of 2b (yield is 64%). $^1H$ NMR (free base) (400 MHz, $CDCl_3$) δ ppm 0.92-0.964 (t, 3H, J=7.6 Hz), 1.39 (bs, 1H), 1.49-1.61 (m, 3H), 2.05-2.10 (m, 1H), 2.66-2.70 (t, 3H, J=7.6 Hz), 2.87-2.94 (m, 2H), 2.98-3.03 (m, 1H), 3.81 (s, 3H), 6.65-6.67 (d, 1H, J=8 Hz), 6.96-6.71 (d, 1H, J=8 Hz), 7.07-7.11 (t, 1H, J=8 Hz).

Procedure B. Resolution of 5-Methoxy-N-propyl-1,2,3,4-tetrahydronaphthalen-2-amine Racemic (±)-2b was resolved into its (+) and (−) isomers by using the both (−) and the (+) isomers of the synthetic resolving agent 4-(2-chlorophenyl)-5,5-dimethyl-2-hydroxy-1,3,2-dioxaphosphorinane 2-oxide. This optically active resolving agents were prepared according to the published procedure. 2b (free base 14.77 g, 67.36 mmol) and (+)-4-(2-chlorophenyl)-5,5-dimethyl-2-hydroxy-1,3,2-dioxaphosphorinane 2-oxide (20.5 g, 74.1 mmol) were dissolved by warming in 100 ml of ethanol. The solution was cooled to room temperature and then at 0° C. The precipitated crystals were filtered off, washed with cold ether to yield 17.4 g of the salt ($[α]_D$= (−)1.2°, c=1 in methanol). Further recrystallization two times from hot ethanol yielded the salt (12.9 g, $[α]_D$=(−) 14.1°, c=1 in methanol). Further crystallization of the salt from hot ethanol did not change the optical rotation to a significant extent. The salt was then neutralized in presence of 20% NaOH solution in water under stirred condition for 2 h at room temperature. The aqueous layer was extracted with dichloromethane (3×100 ml), dried over $Na_2SO_4$ and evaporated to dryness to yield thick transparent liquid (−)2b (5.8 g, [α]$_D$ of the HCl salt=(−)71.5°, (c=1 in methanol) Yield. 78.5%.

(±)-2b (18.5 g, 84.35 mmol) was similarly treated using (−)-4-(2-chlorophenyl)-5,5-dimethyl-2-hydroxy-1,3,2-dioxaphosphorinane 2-oxide (24.5 g, 88.57 mmol). Recrystallization from hot ethanol yielded the salt (16.2 g, [α]$_D$=(+)-13.0, c=1 in methanol). Yield is 78%. Further crystallization of the salt from hot ethanol did not change the optical rotation to a significant extent. Hydrolysis of the chlocyphos salt following above mentioned procedure yielded thick transparent liquid (+)2b. ([α]$_D$ of the HCl salt is (+)-69.8°, c=1 in methanol).

Resolution of (R)-7-methoxy-N-propyl-1,2,3,4-tetrahydronaphthalen-2-amine

This resolution was done according to procedure B, in which (±)-2a (5.99 g, 27.31 mmol) was similarly treated using (−)-4-(2-chlorophenyl)-5,5-dimethyl-2-hydroxy-1,3,2-dioxaphosphorinane 2-oxide (7.93 g, 28.68 mmol). Recrystallization from hot ethanol yielded the salt (5.4 g, [α]$_D$=(+)-12.9°, c=1 in methanol). Yield is 80%. Further crystallization of the salt from hot ethanol did not change the optical rotation to a significant extent. Hydrolysis of the chlocyphos salt following above mentioned procedure yielded R(+)2a, [α]$_D$ of the HCl salt is (+)-68.6° (c=1 in methanol).

Procedure C. Preparation of 2-Chloro-N-(7-methoxy-1,2,3,4-tetrahydro-naphthalen-2-yl)-N-propyl-acetamide (3a)

Compound 2a (HCl salt, 3.117 g, 12.18 mmol) and Et$_3$N (8.4 ml, 60.9 mmol) was stirred at 0° C. in CH$_2$Cl$_2$ (75 ml) for 15 min. Chloroacetylchloride (1.94 ml, 24.37 mmol) was added dropwise and the resulting solution was stirred at room temperature for 30 min, at which time the reaction mixture was poured into a 1M solution of NaOH (50 ml) and the product was extracted with dichloromethane, dried (Na$_2$SO$_4$), filtered, and concentrated. The crude material was purified by column chromatography (Hex:EtOAc, 3:1) to give 3.42 g (95%) of 3a as transparent liquid. $^1$H NMR (400 MHz, CDCl$_3$) δ ppm 0.90-0.98 (m, 3H), 1.64-1.72 (m, 2H), 1.83-2.12 (m, 2H), 2.58-2.70 (m, 1H), 2.84-2.89 (dd, 1H, J$_1$=4.8 Hz, J$_2$=16 Hz), 3.00-3.10 (m, 2H), 3.15-3.26 (m, 2H), 3.82 (s, 3H), 3.95-4.03 (m, 1H), 4.08-4.12 (m, 2H), 6.61-6.62 (dd, 1H, J$_1$=1.6 Hz, J$_2$=4.8 Hz), 6.64-6.77 (m, 1H), 6.96-6.99 (d, 1H, J=12 Hz).

2-Chloro-N-(5-methoxy-1,2,3,4-tetrahydro-naphthalen-2-yl)-N-propyl-acetamide (3b)

This compound was prepared from 2b following the procedure C (yield is 93%). $^1$H NMR (400 MHz, CDCl$_3$) δ ppm 0.92-0.96 (t, 3H, J=8 Hz), 1.64-1.72 (m, 2H), 1.83-2.12 (m, 2H), 2.58-2.70 (m, 1H), 2.84-2.89 (m 1H), 3.00-3.10 (m, 2H), 3.19-3.27 (m, 2H), 3.86 (s, 3H), 3.95-4.03 (m, 1H), 4.08-4.12 (m, 2H), 6.61-6.68 (m, 2H), 7.07-7.11 (t, 3H, J=8 Hz).

(−)-2-chloro-N-(5-methoxy-1,2,3,4-tetrahydronaphthalen-2-yl)-N-propylacetamide, (−)3b Compound (−)2b (HCl salt, 6.0 g, 23.46 mmol) was reacted under similar conditions as reported in procedure C to afford the optically pure (−)3b as transparent liquid (6.52 g, 94%): $^1$H NMR (400 MHz, CDCl$_3$) δ ppm 0.92-0.96 (t, 3H, J=8 Hz), 1.64-1.72 (m, 2H), 1.83-2.12 (m, 2H), 2.58-2.70 (m, 1H), 2.84-2.89 (m, 1H), 3.00-3.10 (m, 2H), 3.19-3.27 (m, 2H), 3.86 (s, 3H), 3.95-4.03 (m, 1H), 4.08-4.12 (m, 2H), 6.61-6.68 (m, 2H), 7.07-7.11 (t, 1H, J=8 Hz).

(+)-2-chloro-N-(5-methoxy-1,2,3,4-tetrahydronaphthalen-2-yl)-N-propylacetamide, (+)-3b Compound (+)2b (HCl salt, 3.5 g, 13.68 mmol) was reacted under similar conditions as in procedure C to afford the optically pure (+)3b as transparent liquid (3.9 g, 90.7%): $^1$H NMR (400 MHz, CDCl$_3$) δ ppm 0.92-0.96 (t, 3H, J=8 Hz), 1.64-1.72 (m, 2H), 1.83-2.12 (m, 2H), 2.58-2.70 (m, 1H), 2.84-2.89 (m, 1H), 3.00-3.10 (m, 2H), 3.19-3.27 (m, 2H), 3.86 (s, 3H), 3.95-4.03 (m, 1H), 4.08-4.12 (m, 2H), 6.61-6.68 (m, 2H), 7.07-7.11 (t, 1H, J=8 Hz).

(+)-2-Chloro-N-(7-methoxy-1,2,3,4-tetrahydronaphthalen-2-yl)-N-propylacetamide, (+)-3a Compound (+)2a (1.12 g, 5.1 mmol) was prepared following procedure C to afford the optically pure (+)3a as transparent liquid (1.44 g, 95%): $^1$H NMR (400 MHz, CDCl$_3$) δ ppm 0.90-0.98 (m, 3H), 1.64-1.72 (m, 2H), 1.83-2.12 (m, 2H), 2.58-2.70 (m, 1H), 2.84-2.89 (m, 1H), 3.00-3.10 (m, 2H), 3.15-3.26 (m, 2H), 3.82 (s, 3H), 3.95-4.03 (m, 1H), 4.08-4.12 (m, 2H), 6.59-6.61 (dd, 1H, J$_1$=1.6 Hz, J$_2$=4.8 Hz), 6.64-6.77 (m, 1H), 6.96-6.99 (d, 1H, J=8.8 Hz).

Procedure D. Preparation of t-butyl 4-(2-((7-methoxy-1,2,3,4-tetrahydronaphthalen-2-yl)(propyl)amino)-2-oxoethyl)piperazine-1-carboxylate (6a)

Compound 3a (3.17 g, 10.72 mmol) and compound 5 (1.397 g, 7.5 mmol), anhydrous K$_2$OC$_3$ powder (7.4 g, 53.58 mmol) were refluxed in acetonitrile (100 ml) for 2 h. The solution was cooled, filtered, and concentrated. The crude material was then partitioned between EtOAc and H$_2$O, and the organic layer was separated, dried (Na$_2$SO$_4$), and concentrated. The crude mixture was purified by column chromatography (EtOAc:Hex; 1:1) to give 3.87 g (81%) of 6a as thick yellow liquid. $^1$H NMR (400 MHz, CDCl$_3$) δ ppm 0.86-0.90 (t, 3H, J=8 Hz), 1.45 (s, 9H), 1.59-1.82 (m, 2H), 1.87-1.94 (m, 1H), 1.95-1.97 (m, 3H), 2.420 (bs, 2H), 2.50-2.63 (m, 2H), 2.76-2.82 (m, 4H), 2.96-3.20 (m, 3H), 3.88-3.47 (m, 4H), 3.81 (s, 3H), 6.60-6.61 m, 1H), 6.65-6.78 (m, 1H), 6.95-6.98 (d, 1H, J=8.8 Hz).

t-butyl-4-(2-((5-methoxy-1,2,3,4-tetrahydronaphthalen-2-yl)(propyl)amino)-2-oxoethyl)piperazine-1-carboxylate (6b)

This compound was prepared from 3b according to the procedure D which yielded 6b as thick yellow liquid (77%). $^1$H NMR (400 MHz, CDCl$_3$) δ ppm 0.87-0.91 (t, 3H, J=8 Hz), 1.44 (s, 9H), 1.58-1.81 (m, 2H), 1.88-1.95 (m, 1H), 1.96-1.98 (m, 3H), 2.40 (bs, 2H), 2.51-2.63 (m, 2H), 2.78-2.83 (m, 4H), 2.95-3.29 (m, 3H), 3.38-3.47 (m, 4H), 3.81 (s, 3H), 6.63-6.70 (m, 2H), 7.10-7.14 (t, 1H, J=8 Hz).

(−)-t-butyl-4-(2-((5-methoxy-1,2,3,4-tetrahydronaphthalen-2-yl)(propyl)amino)-2-oxoethyl)piperazine-1-carboxylate, (−)-6b This compound was prepared from (−)3b (3.5 g, 11.83 mmol) following procedure D to get (−)6b as thick yellow liquid (4.6 g, 87.3%). $^1$H NMR (400 MHz, CDCl$_3$) δ ppm 0.88-0.92 (t, 3H, J=8 Hz), 1.45 (s, 9H), 1.59-1.82 (m, 2H), 1.88-1.95 (m, 1H), 1.96-1.98 (m, 3H), 2.40 (bs, 2H), 2.52-

2.64 (m, 2H), 2.81-2.84 (m, 4H), 2.95-3.29 (m, 3H), 3.39-3.48 (m, 4H), 3.82 (s, 3H), 6.64-6.71 (m, 2H), 7.11-7.14 (t, 1H, J=6 Hz).

(+)-t-butyl-4-(2-((5-methoxy-1,2,3,4-tetrahydronaphthalen-2-yl)(propyl)amino)-2-oxoethyl)piperazine-1-carboxylate, (+)-6b This compound was prepared from (+)3b (4.0 g, 13.52 mmol) according to the procedure D to afford (+)6b as thick yellow liquid (4.44 g, 73.69%). $^1$H NMR (400 MHz, CDCl$_3$) δ ppm 0.86-0.90 (t, 3H, J=8 Hz), 1.42 (s, 9H), 1.58-1.81 (m, 2H), 1.88-1.95 (m, 1H), 1.95-1.97 (m, 3H), 2.39 (bs, 2H), 2.51-2.63 (m, 2H), 2.78-2.83 (m, 4H), 2.94-3.28 (m, 3H), 3.88-3.47 (m, 4H), 3.80 (s, 3H), 6.63-6.70 (m, 2H), 7.09-7.13 (t, 1H, J=8.0 Hz).

(+)-tert-butyl-4-(2-((7-methoxy-1,2,3,4-tetrahydronaphthalen-2-yl)(propyl)amino)-2-oxoethyl)piperazine-1-carboxylate, (+)-6a This compound was prepared from (+)3a (2.32 g, 7.8 mmol) according to the procedure D to afford (+)6a as thick yellow liquid (2.76 g, 79%). $^1$H NMR (400 MHz, CDCl$_3$) δ ppm 0.86-0.90 (t, 3H, J=8 Hz), 1.45 (s, 9H), 1.59-1.82 (m, 2H), 1.87-1.94 (m, 1H), 1.95-1.97 (m, 3H), 2.420 (bs, 2H), 2.50-2.63 (m, 2H), 2.76-2.82 (m, 4H), 2.96-3.20 (m, 3H), 3.88-3.47 (m, 4H), 3.81 (s, 3H), 6.60-6.62 (dd, 1H, J$_1$=2.2 Hz, J$_2$=5.2 Hz), 6.65-6.78 (m, 1H), 6.95-6.97 (d, 1H, J=8 Hz).

Procedure E. Preparation of N-(7-methoxy-1,2,3,4-tetrahydronaphthalen-2-yl)-2-(piperazin-1-yl)-N-propylacetamide (7a)

Compound 6a (3.87 g, 8.68 mmol) was dissolved in 40 ml of dichloromethane and 40 ml of trifluoroacetic acid was added. The mixture was stirred for overnight, at which time the solution was concentrated to dryness, dissolved in saturated NaHCO$_3$ solution and extracted with EtOAc. The organic layer was dried over Na$_2$SO$_4$, filtered, and concentrated to yield 2.91 g (97%) of 7a as yellow wax, which was used in the next reaction. $^1$H NMR (400 MHz, CDCl$_3$) 0.93-0.96 (t, 3H, J=12 Hz), 1.62 (m, 3H), 1.85-1.97 (m, 3H), 2.56 (m, 1H), 2.81-2.88 (m, 5H), 2.98-3.34 (m, 9H), 3.81 (s, 3H), 6.60 (s, 1H), 6.65-6.68 (d, 1H, J=12 Hz), 6.96-6.98 (d, 1H, J=8 Hz).

N-(5-Methoxy-1,2,3,4-tetrahydro-naphthalen-2-yl)-2-piperazin-1-yl-N-propyl-acetamide (7b)

This compound was prepared from 6b as yellow wax (3.87 g, 8.6 mmol) following the procedure E and yield of this reaction is 2.76 g (92%). $^1$H NMR (400 MHz, CDCl$_3$) δ ppm 0.92-0.964 (t, 3H, J=7.6 Hz), 1.63 (m, 3H), 1.84-1.97 (m, 3H), 2.55 (m, 1H), 2.80-2.87 (m, 5H), 2.97-3.34 (m, 9H), 3.82 (s, 3H), 6.64-6.71 (m, 2H), 7.06-7.15 (m, 1H).

(−)-N-(5-methoxy-1,2,3,4-tetrahydronaphthalen-2-yl)-2-(piperazine-1-yl)-N-propylacetamide, (−)7b This compound was prepared from (−)6b (4.6 g, 10.32 mmol) following the procedure E to get (−)7b as yellow wax (3.2 g, 89.6%). $^1$H NMR (400 MHz, CDCl$_3$) δ ppm 0.90-0.93 (t, 3H, J=6.0 Hz), 1.61 (m, 3H), 1.84-1.97 (m, 3H), 2.54 (m, 1H), 2.79-2.86 (m, 5H), 2.97-3.34 (m, 9H), 3.81 (s, 3H), 6.65-6.72 (m, 2H), 7.09-7.16 (m, 1H).

(+)-N-(5-methoxy-1,2,3,4-tetrahydronaphthalen-2-yl)-2-(piperazin-1-yl)-N-propylacetamide, (+)7b Following the procedure E this compound was prepared from (+)6b (4.4 g, 9.87 mmol) to afford (+)7b as yellow wax (3.0 g, 88.23%). $^1$H NMR (400 MHz, CDCl$_3$) δ ppm 0.90-0.94 (t, 3H, J=8.0 Hz), 1.66 (m, 3H), 1.84-1.97 (m, 3H), 2.52 (m, 1H), 2.79-2.87 (m, 5H), 2.97-3.34 (m, 9H), 3.84 (s, 3H), 6.65-6.72 (m, 2H), 7.10-7.16 (m, 1H).

(+)-N-(7-methoxy-1,2,3,4-tetrahydronaphthalen-2-yl)-2-(piperazin-1-yl)-N-propylacetamide, (+)7a This compound was prepared from R(+)6a (3.17 g, 7.11 mmol) following the procedure E that gave quantitative yield R(+)7a as yellow wax (2.46 g). $^1$H NMR (400 MHz, CDCl$_3$) δ ppm 0.93-0.96 (t, 3H, J=6 Hz), 1.62 (m, 3H), 1.85-1.97 (m, 3H), 2.56 (m, 1H), 2.81-2.88 (m, 5H), 2.98-3.34 (m, 9H), 3.81 (s, 3H), 6.60 (s, 1H), 6.65-6.68 (d, 1H, J=12 Hz), 6.95-6.98 (d, 1H, J=12.0 Hz).

Procedure F. Preparation of 7-methoxy-N-(2-(piperazin-1-yl)ethyl)-N-propyl-1,2,3,4-tetrahydronaphthalen-2-amine (8a)

To a suspension of LiAlH$_4$ (1.735 g, 45.73 mmol) in THF (100 ml) at 0° C. was added 7a (3.16 g, 9.15 mmol) in a solution of THF (25 ml). After addition, the mixture was refluxed for 2 h and cooled to 0° C. 15% NaOH was added dropwise to quench the reaction and deactivate the LiAlH$_4$, and the mixture stirred for 20 min, and filtered, washed with ethyl acetate. The solution was dried over Na$_2$SO$_4$, filtered, and concentrated. This crude product was then purified through column chromatography using 20% MeOH in ethyl acetate to get 8a as transparent thick liquid (2.23 g, 74%). $^1$H NMR (400 MHz, CDCl$_3$) δ ppm 0.91-0.96 (t, 3H, J=10 Hz), 1.40-1.6 (m, 3H), 1.97-2.01 (m, 1H), 2.139 (bs, 1H) 2.41-3.11 (m, 18H), 3.82 (s, 3H), 6.61 (s, 1H), 6.66-6.79 (d, 1H, J=6 Hz), 6.95-6.98 (d, 1H, J=8.8 Hz).

5-Methoxy-N-(2-(piperazin-1-yl)ethyl)-N-propyl-1,2,3,4-tetrahydronaphthalen-2-amine (8b)

This compound was prepared from 7b following the procedure F to get 8b as transparent thick liquid (yield is 72.5%). $^1$H NMR (400 MHz, CDCl$_3$) δ ppm 0.92-0.96 (t, 3H, J=7.6 Hz), 1.41-1.59 (m, 3H), 1.98-2.22 (m, 1H), 2.41-3.1 (m, 19H), 3.81 (s, 3H), 5.2 (bs, 1H), 6.62-6.64 (d, 1H, J=8 Hz), 6.68-6.69 (d, 1H, J=4 Hz), 7.05-7.09 (t, 1H, J=8 Hz).

(−)-5-methoxy-N-(2-(piperazin-1-yl)ethyl)-N-propyl-1,2,3,4-tetrahydronaphthalen-2-amine, (−)8b This compound was prepared from (−)7b (3.8 g, 11 mmol) following the procedure F to get (−)8b as transparent thick liquid (yield is 3.26 g, 89%). $^1$H NMR (400 MHz, CDCl$_3$) δ ppm 0.87-0.91 (t, 3H, J=8.0 Hz), 1.16-1.19 (t, 3H, J=6 Hz), 1.98-2.1 (m, 1H), 2.46-3.01 (m, 19H), 3.81 (s, 3H), 5.93 (bs, 1H), 6.64-6.66 (d, 1H, J=8.0 Hz), 6.70-6.71 (d, 1H, J=4.0 Hz), 7.07-7.11 (t, 1H, J=8.0 Hz).

(+)-5-methoxy-N-(2-(piperazin-1-yl)ethyl)-N-propyl-1,2,3,4-tetrahydronaphthalen-2-amine, (+)8b This compound was prepared from (+)7b (3.5 g, 10.13 mmol) following the above procedure F that yielded 2.48 g (74%) of (+)8b as transparent thick liquid. $^1$H NMR (400

MHz, CDCl₃) δ ppm 0.88-0.91 (t, 3H, J=6.0 Hz), 1.17-1.20 (t, 3H, J=6 Hz), 1.97-2.00 (m, 1H), 2.46-3.01 (m, 19H), 3.81 (s, 3H), 5.71 (bs, 1H), 6.65-6.67 (d, 1H, J=8.0 Hz), 6.71-6.72 (d, 1H, J=4.0 Hz), 7.06-7.10 (t, 1H, J=8.0 Hz).

(+)-7-methoxy-N-(2-(piperazin-1-yl)ethyl)-N-propyl-1,2,3,4-tetrahydronaphthalen-2-amine, (+)8a This compound was prepared from (+)7a (2.46 g, 7.1 mmol) following procedure F for to make (+)8a as transparent thick liquid (yield is 2.15 g, 91%). ¹H NMR (400 MHz, CDCl₃) δ ppm 0.91-0.96 (t, 3H, J=10 Hz), 1.40-1.6 (m, 3H), 1.97-2.01 (m, 1H), 2.139 (bs, 1H) 2.41-3.11 (m, 18H), 3.82 (s, 3H), 6.61 (s, 1H), 6.66-6.79 (d, 1H, J=12 Hz), 6.96-6.98 (d, 1H, J=8 Hz).

Procedure G. Preparation of 7-[(2-Piperazin-1-yl-ethyl)-propyl-amino]-5,6,7,8-tetrahydro-naphthalen-2-ol (9a)

Compound 8a (2.23 g, 6.73 mmol) was dissolved in 80 ml of CH₂Cl₂ and cooled to −78° C. 1M boron tribromide solution in dichloromethane (20 ml) was added dropwise and the mixture was allowed to warm to ambient temperature and was stirred overnight. Sat. NaHCO₃ was added and the product extracted with dichloromethane, dried over Na₂SO₄, filtered, and concentrated to yield the crude product. Column chromatography (7:2:1; CH₂Cl₂:MeOH:Et₃N) afforded 1.62 g (76%) of 9a as brown wax. ¹H NMR (400 MHz, CDCl₃) δ ppm 0.84-0.87 (t, 3H, J=6 Hz), 1.27-1.31 (m, 2H), 1.70-1.82 (m, 3H), 2.25-2.28 (m, 1H), 2.58-2.06 (m, 1H), 2.73-2.78 (m, 4H), 2.97-3.09 (m, 5H), 3.16-3.20 (m, 7H), 6.45 (s, 1H), 6.53-6.55 (d, 1H, J=9.2 Hz), 6.84-6.86 (d, 1H, J=8 Hz).

6-[(2-Piperazin-1-yl-ethyl)-propyl-amino]-5,6,7,8-tetrahydro-naphthalen-1-ol (9b)

This compound was prepared from 8b following the procedure G (yield is 78%) as brown wax. ¹H NMR (400 MHz, CDCl₃) δ ppm 0.99-1.02 (t, 3H, 7.6 Hz), 1.28-1.30 (m, 2H), 1.71-1.83 (m, 3H), 2.26-2.29 (m, 1H), 2.57-2.60 (m, 1H), 2.72-2.77 (m, 4H), 2.97-3.07 (m, 5H), 3.16-3.21 (m, 7H), 6.5-6.52 (d, 1H, J=8 Hz), 6.55-6.57 (d, 1H, J=8 Hz), 6.9-6.95 (t, 1H, J=10 Hz).

(−)-6-((2-(piperazin-1-yl)ethyl)(propyl)amino)-5,6,7,8-tetrahydronaphthalen-1-ol, (−)9b This compound was prepared from (−)8b (3.26 g, 9.8 mmol) following the procedure G to make (−)9b as brown wax (yield is 2.23 g, 71.5%). ¹H NMR (400 MHz, CDCl₃) δ ppm 0.86-0.89 (t, 3H, 6.0 Hz), 1.08-1.11 (t, 2H, J=6 Hz), 1.40-1.51 (m, 3H), 1.98-2.01 (m, 1H), 2.46-2.54 (m, 9H), 2.62-2.67 (m, 4H), 2.87-2.96 (m, 4H), 6.47-6.49 (d, 1H, J=8 Hz), 6.54-6.56 (d, 1H, J=8 Hz), 6.91-6.95 (t, 1H, J=8 Hz).

(+)-6-((2-(piperazin-1-yl)ethyl)(propyl)amino)-5,6,7,8-tetrahydronaphthalen-1-ol, (+)9b This compound was prepared from (+)8b (2.48 g, 7.48 mmol) following the procedure G which afforded (+)9b as brown wax (yield 1.74 g, 73.2%). ¹H NMR (400 MHz, CDCl₃) δ ppm 0.88-0.91 (t, 3H, 6.0 Hz), 1.10-1.13 (t, 2H, J=6 Hz), 1.40-1.51 (m, 3H), 1.98-2.01 (m, 1H), 2.48-2.56 (m, 9H), 2.64-2.69 (m, 4H), 2.87-2.96 (m, 4H), 6.48-6.50 (d, 1H, J=8 Hz), 6.55-6.56 (d, 1H, J=4 Hz), 6.92-6.95 (t, 1H, J=6 Hz).

(+)-7-((2-(piperazin-1-yl)ethyl)(propyl)amino)-5,6,7,8-tetrahydronaphthalen-2-ol, (+)9a This compound was prepared from (+)8a (2.15 g, 6.5 mmol) following the procedure G to yield (+)9a as brown wax (0.39 g, 20%). ¹H NMR (400 MHz, CDCl₃) δ ppm 0.84-0.87 (t, 3H, J=6 Hz), 1.70-1.82 (m, 3H), 2.25-2.28 (m, 1H), 2.58-2.06 (m, 1H), 2.73-2.78 (m, 4H), 2.97-3.09 (m, 5H), 3.16-3.20 (m, 9H), 6.45 (s, 1H), 6.53-6.55 (d, 1H, J=8 Hz), 6.84-6.86 (d, 1H, J=8 Hz).

5-(chloromethyl)quinolin-8-ol (11)

A mixture of commercially available compound 10, 8-quinolinol (7.3 g, 50.29 mmol), 8 mL of 32% HCl in water, and 8 mL of 37% formaldehyde in water at 0° C. was treated with hydrogen chloride gas for 6 h. The solution was allowed to stand at room temperature for 2 h without stirring. The yellow solid obtained was collected on a filter, washed with 90% alcohol, and dried under vacuum to give 5-chloromethyl-8-quinolinol hydrochloride 11 as yellow solid (9.0 g, 77.78%). ¹H NMR of HCl salt (400 MHz, DMSO) δ ppm 5.30 (s, 2H), 7.49-7.51 (d, 1H, J=8 Hz), 7.83-7.85 (d, 1H, J=8 Hz), 8.08-8.12 (dd, 1H, J₁=5.6 Hz, J₂=8.8), 9.098-9.110 (d, 1H, J=4.8 Hz), 9.193-9.213 (d, 1H, J=8 Hz)

Procedure H. Preparation of 5-((4-(2-((7-hydroxy-1,2,3,4-tetrahydronaphthalen-2-yl)(propyl)amino)ethyl)piperazin-1-yl)methyl) quinolin-8-ol (12a)

To a mixture of 5-chloromethyl-8-quinolinol hydrochloride, 11 (0.20 g, 0.86 mmol) and diisopropylethylamine (0.3 mL, 1.73 mmol, 2.2 equiv) in 25 mL CHCl₃ at 0° C. was added 9a (0.25 g, 0.78 mmol). The mixture was stirred for 24 h at room temperature. CHCl₃ (100 mL) was added and the solution obtained was washed with 10% NaHCO₃, brine, and then dried over Na₂SO₄. The solution was filtered and evaporated to dryness. The residue was made hydrochloride salt and crystallized from ethanol to yield 12a as yellow solid (0.28 g, 57.3%). ¹H NMR of HCl salt (400 MHz, DMSO-d₆) δ ppm 0.88-0.99 (m, 3H), 1.79-1.81 (bs, 4H), 2.298 (bs, 1H), 2.476-2.48 (m, 2H), 2.74 (s, 2H), 2.96-3.02 (t, 1H, J=12 Hz), 3.122 (bs, 3H), 3.34-3.65 (m, 12H), 6.51-6.56 (m, 2H), 6.86-6.88 (d, 1H, J=8 Hz), 7.50-7.52 (d, 1H, J=8 Hz), 7.997-8.008 (m, 2H); 9.06-9.07 (d, 1H, J=4 Hz); 9.49-9.51 (d, 1H, J=8 Hz). The hydrochloride salt mp 242-242° C. Analysis calculated for (C₂₉H₄₀.₆N₄O₃.₃, 4HCl) C, H, N.

5-((4-(2-((5-hydroxy-1,2,3,4-tetrahydronaphthalen-2-yl)(propyl)amino)ethyl)piperazin-1-yl)methyl) quinolin-8-ol (12b)

This compound was prepared following the procedure H in which compound 11 (0.18 g, 0.8 mmol) and 9b (0.23 g, 0.72 mmol) were used to afford 12b as yellow solid (0.265 g, 59%). ¹H NMR of salt (400 MHz, DMSO-d₆) δ ppm 0.84-0.87 (t, 3H, J=6 Hz), 1.79-1.81 (bs, 4H), 2.298 (bs, 1H), 2.476-2.48 (m, 2H), 2.74 (s, 2H), 2.96-3.02 (t, 1H, J=12 Hz), 3.122 (bs, 3H), 3.34-3.65 (m, 12H), 6.50-6.52 (d, 1H, J=8 Hz), 6.55-6.57 (d, 1H, J=8 Hz), 6.93-6.96 (t, 1H, J=6 Hz), 7.06-7.08 (d, 1H, J=8 Hz), 7.32-7.34 (d, 1H, J=8 Hz), 7.44-7.46 (m, 1H), 8.66-8.68 (d, 1H, J=8 Hz), 8.77-8.78 (d, 1H, J=4 Hz). The hydrochloride salt mp 252-255° C. Analysis calculated for (C₂₉H₄₃N₄O₄.₅, 4HCl) C, H, N.

8-methoxyquinolin-4-ol (16)

Trimethyl orthoformate (190 mL, 1.7 mol) and isopropylidene malonate (Meldrum's acid, 5 gm, 34.7 mmol) were refluxed for 1 h, and then cooled slightly. O-anisidine (3.9 ml, 34.7 mmol) was added to the mixture along with 8 mL of dimethylformamide (DMF) and the resulting mixture was reheated to reflux for 2 h. The mixture was cooled to room temperature, poured into cold water (150 mL), upon which a crystalline solid formed and was filtered and allowed to dry in open air. It was then recrystalized from methanol to get pure white solid 15. The solid material was then poured into warm diphenyl ether (50 ml) and heated to 300° C. for 15 minutes under reflux condensor, then cooled down to room temperature. The cyclized product was isolated by cooling and subsequent precipitation by mixing with hexane followed by filtration, washing with additional hexane, and drying. It was the purified by column chromatograpy (EtOAc:MeOH; 95:5) to give 2.65 g (overall 44%) of 16 as off white solid. $^1$H NMR (400 MHz, CDCl$_3$) δ ppm 3.99 (s, 3H), 6.31-6.33 (d, 1H, J=8 Hz), 7.03-7.05 (d, 1H, J=8 Hz), 7.23-7.27 (t, 1H, J=8 Hz), 7.64-7.67 (t, 1H, J=6 Hz), 7.92-7.94 (d, 1H, 8 Hz).

4-Chloro-8-methoxyquinoline (17)

Compound 16 (2.65 g, 15.1 mmol) was dissolved in POCl$_3$ (4.2 ml, 45.3 mmol) under nitrogen atmosphere and refluxed for 2 h. It was then cooled and concentrated under vacuum. The solid concentrate was taken in a beaker with 200 ml water neutralized with NaHCO$_3$ powder and extracted with EtOAc. The solution was dried over Na$_2$SO$_4$, filtered, and concentrated. This crude product was then purified through column chromatography using ethyl acetate to get 17 as brown solid (2.113 g, 72%). $^1$H NMR (400 MHz, CDCl$_3$) δ ppm 4.079 (s, 3H), 7.08-7.1 (d, 1H, J=8 Hz), 7.49-7.56 (m, 2H), 7.76-7.78 (d, 1H, J=8 Hz), 8.76-8.77 (d, 1H, J=4 Hz).

Procedure I. Preparation of 7-((2-(4-(8-methoxyquinolin-4-yl)piperazin-1-yl)ethyl) (propyl)amino)-5,6,7,8-tetrahydronaphthalen-2-ol (18a)

To a mixture of 9a (0.6 g, 1.89 mmol) and diisopropylethylamine (0.4 mL, 2.08 mmol, 1.1 equiv) in 15 mL isopropanol was added 4-chloro-8-methoxyquinoline (17) (0.366 g, 1.89 mmol, 1 equiv). The mixture was refluxed with stirring for overnight. It was then evaporated and concentrate was dissolved in CH$_2$Cl$_2$ (50 mL) and the solution obtained was washed with 5% NaHCO$_3$ (3×50 mL), brine (2×50 mL), and then dried over Na$_2$SO$_4$. The solution was filtered and evaporated to dryness. The residue was purified through column chromatography using 20% methanol in ethyl acetate to give 18a as white wax (0.66 g, 73% yield). $^1$H NMR (400 MHz, CDCl$_3$) δ ppm 0.93-0.95 (t, 3H, 4 Hz), 1.75 (m, 3H), 2.11-2.21 (m, 2H), 2.69-3.07 (m, 13H), 3.23 (s, 4H), 3.47 (s, 1H), 4.02 (s, 3H), 6.60 (s, 1H), 6.66-6.68 (d, 1H, J=8 Hz), 6.82-6.84 (t, 2H, J=4 Hz), 6.98-7.00 (d, 1H, J=8 Hz), 7.36-7.42 (t, 1H, J=12 Hz), 7.50-7.52 (d, 1H, J=8 Hz), 8.67-8.68 (d, 1H, J=4 Hz).

Preparation of 6-((2-(4-(8-methoxyquinolin-4-yl)piperazin-1-yl)ethyl)(propyl)amino)-5,6,7,8-tetrahydronaphthalen-1-ol (18b)

This compound was prepared from 9b (0.668 g, 2.1 mmol) and 17 (0.4 g, 2.1 mmol) following the procedure I to get 18b as white wax (yield 0.76 g, 75%). $^1$H NMR (400 MHz, CDCl$_3$) δ ppm 0.92-0.95 (t, 3H, J=6 Hz), 1.58-1.65 (m, 3H), 2.04-2.14 (m, 2H), 2.73-2.96 (m, 13H), 3.25 (bs, 4H), 3.48 (s, 1H), 4.04 (s, 3H), 6.57-6.59 (d, 1H, J=8 Hz), 6.66-6.68 (d, 1H, J=8 Hz), 6.86-6.87 (d, 1H, J=4 Hz), 6.92-6.96 (t, 1H, J=8 Hz), 6.99-7.01 (d, 1H, J=8 Hz), 7.37-7.41 (t, 1H, J=8 Hz), 7.54-7.56 (d, 1H, J=8 Hz), 8.72-8.73 (d, 1H, J=4 Hz).

Preparation of (−)-6-((2-(4-(8-methoxyquinolin-4-yl)piperazin-1-yl)ethyl) (propyl)amino)-5,6,7,8-tetrahydronaphthalen-1-ol, (−)18b This compound was prepared from (−)9b (0.50 g, 1.6 mmol) and 17 (0.305 g, 1.6 mmol) following the procedure I to afford (−)18b as white wax (0.419 g, 56%). $^1$H NMR (400 MHz, CDCl$_3$) δ ppm 0.98-1.00 (t, 3H, J=4 Hz), 1.58-1.65 (m, 3H), 2.04-2.14 (m, 2H), 2.85-3.12 (m, 13H), 3.25 (bs, 4H), 3.48 (s, 1H), 4.06 (s, 3H), 6.57-6.59 (d, 1H, J=8 Hz), 6.87-6.88 (d, 1H, J=4 Hz), 6.92-6.97 (m, 2H), 7.01-7.03 (d, 1H, J=8 Hz), 7.39-7.43 (t, 1H, J=8 Hz), 7.54-7.57 (t, 1H, J=6 Hz), 8.73-8.74 (d, 1H, J=4 Hz).

(+)-6-((2-(4-(8-methoxyquinolin-4-yl)piperazin-1-yl)ethyl) (propyl)amino)-5,6,7,8-tetrahydronaphthalen-1-ol (+)18b This compound was prepared from (+)9b (0.62 g, 1.95 mmol) and 17 (0.378 g, 1.95 mmol) following the procedure I to make (+)18b as white wax (0.565 g, 61%). $^1$H NMR (400 MHz, CDCl$_3$) δ ppm 0.97-0.99 (t, 3H, J=4 Hz), 1.57-1.64 (m, 3H), 2.04-2.14 (m, 2H), 2.85-3.12 (m, 13H), 3.25 (bs, 4H), 3.48 (s, 1H), 4.06 (s, 3H), 6.57-6.59 (d, 1H, J=8 Hz), 6.87-6.88 (d, 1H, J=4 Hz), 6.93-6.97 (m, 2H), 7.01-7.03 (d, 1H, J=8 Hz), 7.38-7.42 (t, 1H, J=8 Hz), 7.53-7.56 (t, 1H, J=6 Hz), 8.72-8.73 (d, 1H, 4 Hz)

(+)-7-((2-(4-(8-methoxyquinolin-4-yl)piperazin-1-yl)ethyl) (propyl)amino)-5,6,7,8-tetrahydronaphthalen-2-ol, (+)18a This compound was prepared from (+)9a (0.39 g, 1.22 mmol) and 17 (0.214 g, 1.11 mmol) following the procedure I to get (+)18a as white wax (0.110 g, 19%). $^1$H NMR (400 MHz, CDCl$_3$) δ ppm 0.93-0.95 (t, 3H, 4 Hz), 1.75 (m, 3H), 2.11-2.21 (m, 2H), 2.69-3.07 (m, 13H), 3.23 (s, 4H), 3.47 (s, 1H), 4.02 (s, 3H), 6.60 (s, 1H), 6.66-6.68 (d, 1H, J=8 Hz), 6.82-6.84 (t, 2H, J=4 Hz), 6.98-7.00 (d, 1H, J=8 Hz), 7.36-7.42 (t, 1H, J=12 Hz), 7.50-7.52 (d, 1H, J=8 Hz), 8.67-8.68 (d, 1H, J=4 Hz).

Procedure J. Preparation of 4-(4-(2-(7-hydroxy-1,2,3,4-tetrahydronaphthalen-2-yl)(propyl)amino)ethyl) piperazine-1-yl)quinolin-8-ol (19a, hydrochloride salt)

Compound 18a (0.5 g, 1.05 mmol) and 48% aqueous HBr (10 ml) was refluxed for overnight. It was then cooled and concentrated under vacuum and 50 ml water was added to the crude residue and made freebase with NaHCO$_3$ powder which was then extracted with CH$_2$Cl$_2$, dried over Na$_2$SO$_4$, filtered and evaporated. The greenish solid crude product was dissolved in minimum amount of ethanol at which time ethereal HCl was added, and the crude salt was filtered and dried over vacuum oven. The crude salt was then purified by recrystallization in ethanol. The HCl salt was filtered and dried to yield 0.329 g (26%) of the final compound as off white solid. $^1$H NMR of HCl salt (400 MHz, DMSO-d$_6$) δ ppm 0.93-0.95 (t, 3H, J=4 Hz), 1.75 (m, 3H), 2.11-2.21 (m, 2H), 2.69-3.07 (m, 13H), 3.23 (s, 4H), 3.47 (s, 1H), 6.58 (s, 1H), 6.60-6.61 (d, 1H, J=4 Hz), 6.91-6.93 (d, 1H, J=8 Hz), 7.35-7.40 (m, 2H), 7.60-7.68 (m, 2H), 8.60-8.62 (d, 1H, J=8 Hz). The hydrochlo-

4-(4-(2-(5-hydroxy-1,2,3,4-tetrahydronaphthalen-2-yl)(propyl)amino)ethyl) piperazin-1-yl)quinolin-8-ol (19b, hydrochloride salt)

This compound was prepared from 18b following the procedure J that gave 19b off white solid (31%). $^1$H NMR of HCl salt (400 MHz, DMSO-$d_6$) δ ppm 0.92-0.95 (t, 3H, J=6 Hz), 1.58-1.65 (m, 3H), 2.04-2.14 (m, 2H), 2.73-2.96 (m, 13H), 3.25 (bs, 4H), 3.48 (s, 1H), 6.55-6.57 (d, 1H, J=8 Hz), 6.62-6.64 (d, 1H, J=8 Hz), 6.92-6.96 (t, 1H, J=8 Hz), 7.31-7.33 (d, 1H, J=8 Hz), 7.39-7.41 (d, 1H, J=8 Hz), 7.55-7.57 (m, 2H), 8.57-8.59 (d, 1H, J=8 Hz). The hydrochloride salt, mp 249-251° C. Analysis calculated for ($C_{28}H_{38.4}N_4O_{3.2}$, 4HCl) C, H, N.

(−)-4-(4-(2-((5-hydroxy-1,2,3,4-tetrahydronaphthalen-2-yl) (propyl)amino)ethyl)piperazin-1-yl)quinolin-8-ol ((−)19b, hydrochloride salt)

This compound was prepared from (−)18b (0.480 g, 1.01 mmol) following the procedure J to afford (−)19b off white solid (0.214.65 g, 35%). $^1$H NMR (free base, 400 MHz, $CDCl_3$) δ ppm 0.95-0.99 (t, 3H, J=8 Hz), 1.46-1.53 (m, 3H), 2.24-2.50 (m, 2H), 2.84-3.06 (m, 13H), 3.25 (bs, 4H), 3.49-3.67 (m, 1H), 6.52-6.54 (d, 1H, J=8 Hz), 6.60-6.62 (d, 1H, J=8 Hz), 6.85-6.86 (d, 1H, J=4 Hz), 6.95-6.99 (t, 1H, J=8 Hz), 7.10-7.12 (d, 1H, J=8 Hz), 7.35-7.39 (t, 1H, J=8 Hz), 7.44-7.46 (d, 1H, 8 Hz), 8.57-8.58 (d, 1H, J=4 Hz). $[\alpha]^{25}_D$=(−)36° (c=0.5, $CH_3OH$). The hydrochloride salt, mp 237-240° C. Analysis calculated for ($C_{28}H_{37}N_4O_{2.5}$, 4HCl) C, H, N.

(+)-4-(4-(2-((5-hydroxy-1,2,3,4-tetrahydronaphthalen-2-yl) (propyl)amino)ethyl)piperazin-1-yl)quinolin-8-ol ((+)19b, hydrochloride salt)

This compound was prepared from (+)18b (0.520 g, 1.10 mmol) following the procedure J to make (+)19b off white solid (0.259 g, 39%). $^1$H NMR (free base, 400 MHz, $CDCl_3$) $^1$H NMR (400 MHz, $CDCl_3$) δ ppm 0.96-0.99 (t, 3H, J=6 Hz), 1.47-1.52 (m, 3H), 2.24-2.50 (m, 2H), 2.85-3.05 (m, 13H), 3.25 (bs, 4H), 3.49-3.67 (m, 1H), 6.53-6.55 (d, 1H, J=8 Hz), 6.61-6.63 (d, 1H, J=8 Hz), 6.86-6.88 (d, 1H, J=8 Hz), 6.95-6.99 (t, 1H, J=8 Hz), 7.10-7.12 (d, 1H, J=8 Hz), 7.34-7.38 (t, 1H, J=8 Hz), 7.46-7.48 (d, 1H, 8 Hz), 8.56-8.57 (d, 1H, J=4 Hz). $[\alpha]^{25}_D$=(+)33.6° (c=0.5, $CH_3OH$). The hydrochloride salt, mp 230-232° C. Analysis calculated for ($C_{28}H_{41}N_4O_{4.5}$, 4HCl) C, H, N.

(+)-4-(4-(2-((7-hydroxy-1,2,3,4-tetrahydronaphthalen-2-yl) (propyl)amino)ethyl)piperazin-1-yl)quinolin-8-ol ((+)19a, hydrochloride salt)

This compound was prepared from (+)18a (0.110 g, 0.232 mmol) following the procedure J that yielded (+)19a off white solid (0.055 g, 43%). $^1$H NMR of HCl salt (400 MHz, DMSO-$d_6$) δ ppm δ ppm 0.89-0.91 (t, 3H, J=4 Hz), 1.71 (m, 3H), 2.09-2.19 (m, 2H), 2.67-3.06 (m, 13H), 3.20 (s, 4H), 3.47 (s, 1H), 6.56 (s, 1H), 6.59-6.60 (d, 1H, J=4 Hz), 6.91-6.92 (m, 1H, J=4 Hz), 7.32-7.36 (m, 2H), 7.64-7.68 (m, 2H), 8.59-8.61 (d, 1H, J=8 Hz). $[\alpha]^{25}_D$=(+)32.4° (c=0.5, $CH_3OH$). The hydrochloride salt, mp 239-241° C. Analysis calculated for ($C_{28}H_{37.4}N_4O_{2.7}$, 4HCl) C, H, N.

Complexation of 19b with Iron (III) Chloride:

Compound 19b (4HCl salt) was dissolved in water to make 600 μM solution and the pH of the solution was found to be 3.66. The UV scanned spectra of the solution was taken from 200 nm to 760 nm. $FeCl_3$, $6H_2O$ was next dissolved in water to make 600 colorless solution. The two solutions were mixed together in equal volume which gave green color solution at pH 3.76. The solution was subjected to UV scan as before. Then pH of the solution was next increased to 4.0 by adding base diisopropylethylamine (DIPEA) (diluted with $H_2O$) base which produced deep green color which was followed by UV spectra scan. The pH of the solution was next increased to 7.4 by adding additional amount of DIPEA which produced light brown color solution followed by scanning in UV spectra from 390 nm to 770 nm.

Iron-Chelating Capacity.

The iron-binding capacity of the test compound 19b (iron chelating compounds) was determined by assessing their ability to compete with ferrozine (3-[2-pyridyl]-5,6-diphenyl-1,2,4-triazine-4,4'-disulfonic acid) for ferrous ions which result is in reduced absorbance of the ferrozine-Fe(II) complex at 562 nm. Complexation reactions were carried out in 5% ammonium acetate buffer (pH 6.9). Various conc. of the test compound 19b (25-250 μM) were incubated with {[NH4]2[Fe][SO4]2.6H2O} (20 μM) for 30 min, followed by the addition of 80 μM ferrozine. After incubation at ambient temperature for 1 h, the UV absorbance of the resulting solutions at 562 nm was read. The limitation of this assay is that, chelating compound forms complex with iron at higher drug concentration which also gives absorbance reading at 562 nm. We subtracted the absorbance by a blank solution containing only drug and iron without ferrozine (corrected absorbance). The Fe (II)-chelating effect was calculated as follows:

Chelating effect (%)=[1−($Abs_{562nm}$ of sample)/($Abs_{562nm}$ of control)]×100

The chelating effect is expressed as percent of control [80 uM ferrozine, 20 uM Ferrous ammonium sulfate in pH 6.9 ammonium acetate buffer (5%)].

Deoxyribose Antioxidant Assay Procedure.

The assay was carried out by following the published procedure. Briefly, the reaction mixture contained in a final volume of 1.0 ml, which contained the following reagents: deoxyribose (2.8 mM), potassium phosphate buffer, pH 7.4 (100 mM), increasing concentration of test drug (0-1000 μM), ferric chloride (100 μM), ascorbic acid (100 μM), EDTA (100 μM) and $H_2O_2$ (1 mM). Fresh solution of deoxyribose, ferric chloride and $H_2O_2$ were made prior to use. All solutions were made in degassed water. $H_2O_2$ solution was added at the end to initiate the reaction to form hydroxyl radical. The reaction was continued for 30 minutes at 37° C. The extent of deoxyribose degradation was monitored by formation of malondialdehyde (a pink color chromogen) determined by the addition of 1 ml of 1% (w/v) 2-Thiobarbituric acid in 50 mM NaOH (TBA) and 1 ml of 2.8% (w/v) trichloroacetic acid (TCA). After addition of TBA and TCA, the solutions were heated at 85° C. for 20 minutes. Pink chromogen was formed. The solutions were cooled and the resultant absorbance was read at 532 nM against appropriate blanks. The intensity of pink color decreases in presence of increased concentration of hydroxyl radical scavenger.

Dopamine Receptor Affinity and Agonism

Binding potency was monitored by inhibition of [3H]spiperone (15.0 Ci/mmole, Perkin-Elmer) binding to dopamine rD2 and rD3 receptors expressed in HEK-293 cells, in a buffer containing 0.9% NaCl as described by us previously. Functional activity of test compounds in activating dopamine hD2 and hD3 receptors expressed in CHO cells was measured by stimulation of binding of [35S]GTPγS (1250 Ci/mmole, Perkin-Elmer) in comparison to stimulation by the full agonist dopamine as described by us previously.

Animal Experiment:

Drugs and Chemicals:

The following commercially available drugs were used in the experiment: reserpine hydrochloride (Alfa Aesar), Ropinirole (Sigma), The hydrochloride salts of compounds (−)-19b and ropinirole were dissolved in water for both locomotor and 6-OH-DA rotational experiments. Reserpine was dissolved in 10-25 µL of glacial acetic acid and further diluted with 5.5% glucose solution. All compounds for this study were administered in a volume of 0.1 to 0.2 mL for subcutaneous administration and 0.7 to 0.9 mL for intraperitoneal administration into each rat.

Animals:

In rodent studies, animals were male Sprague-Dawley rats from Harlan (Indianapolis, Ind.) weighing 220-225 g unless otherwise specified. The lesioned rats (290-320 g) were purchased from Taconic Biotechnology (Rensselaer, N.Y.) and their unilateral lesion was checked twice by apomorphine challenge following the surgery. Animals were maintained in sawdust-lined cages in a temperature and humidity controlled environment at 22±1° C. and 60±5% respectively, with a 12-h light/dark cycle, with lights on from 6:00 AM to 6:00 PM. They were group housed with unrestricted access to food and water. All experiment was performed during the light component. All animal use procedures were in compliance with the Wayne State University Animal Investigation Committee consistent with AALAC guidelines.

Reversal of Reserpine-Induced Hypolocomotion in Rats:

Administration of reserpine induces catalepsy in rodents primarily by blocking the vesicular monoamine trasporter (VMAT) which helps in the internalization of monoamines into vesicles, resulting in metabolism of unprotected monoamines in the cytosol that ultimately causes depletion of monoamines in the synapse of the peripheral sympathetic nerve terminals. The ability of the compound (−)-19b to reverse the reserpine induced hypolocomotion was investigated. Ropinirole was used as standard reference compound in this study. Reserpine (5.0 mg/kg, s.c.) or saline (s.c.) were administered 18 h before the injection of drug or vehicle (i.p.). The rats were placed individually in chambers for 1 h for acclimatization purpose before the administration of the test drug, standard drug or vehicle. Immediately after administration of drug or vehicle, animals were individually placed in versamax animal activity monitor chamber (45×30×20 cm) (AccuScan Instruments, Inc. Columbus, Ohio) to start measuring locomotor activity. Locomotion was monitored for 6 h. Consecutive interruption of two infrared beams situated 24 cm apart and 4 cm above the cage floor in the monitor chamber recorded movement. The data were presented as horizontal counts (HACTV). The effect of the individual doses of drugs on locomotor activity was compared with respect to saline treated controls (mean±S.E.M.). The data were analyzed by one way analysis of variance (ANOVA) followed by Dunnett's post-hoc test. The effect was considered significant if the difference from control group was observed at $p<0.05$.

In Vivo Rotational Experiment with 6-OH-DA Lesioned Rats

The first 14 days post-lesion challenge with apomorphine was done with lesioned animals to observe a complete rotation session post administration. In the second challenge with apomorphine (0.05 mg/kg) 21 days post lesion, contralateral rotations were recorded for 30 min; apomorphine produced rotations in all four rats (average rotation>250) indicating successful unilateral lesion. In these rats, lesion was performed on the left side of the medial forebrain bundle in the brain and the coordinates used from Bregma are: AP −4.3, ML +1.2, DV −8.3. The rotations produced upon agonist challenge occurring clockwise. In this study, apomorphine was also used as a reference compound. The test drugs including ropinirole were dissolved in saline and were administered SC. The rotations were measured over 7-10 hours. For control, vehicle was administered alone. Rotations were measured in the Rotomax Rotometry System (AccuScan Instruments, Inc. Columbus, Ohio) equipped with Rotomax Analyser, high resolution sensor and animal chambers with harnesses. Data were analyzed with Rotomax Window software program. Test drug (−)-19b (0.5 and 1 µMol/kg) and ropinirole (5 µMol/kg) dissolved in saline were administered sc. The rotations were measured in a rotational chamber immediately after administration of drugs. The data were collected at every 30 min. Data were analyzed by Graph Pad (Version 4, San Diego) program. All drugs produced contralateral rotations in all lesioned rats which lasted over 3-10 hours.

2. Compounds Having Formulae VI

FIG. 15 provides scheme 5 for preparing the compounds with formulae VIa and VIb. Table 3 (FIG. 16) provides inhibition constants for competing for [3H]spiperone binding to cloned D2L and D3 receptors expressed in HEK cells.

Analytical silica gel-coated TLC plates (silica gel 60 F254) were purchased from EM Science and were visualized with UV light or by treatment with either phosphomolybdic acid (PMA) or ninhydrin. Chromatography was carried out on Baker silica gel 40 mM. $^1$H NMR spectra were routinely obtained on Varian 400 MHz FT NMR spectrometer. The NMR solvent used was either $CDCl_3$ or $CD_3OD$ as indicated. TMS was used as an internal standard. Elemental analyses were performed by Atlantic Microlab, Inc. and were within 0.4% of the theoretical value. Optical rotations were recorded on a Perkin-Elmer 241 polarimeter.

4-Chloroquinolin-8-ol (22). A stirred solution of compound 21 (5.0 g, 25.82 mmol) and 48% aqueous HBr (25 mL) was refluxed for 26 hours. The HBr was evaporated in vacuo and the salt was recrystallized from ethanol. The salt was then neutralized in the presence of saturated $NaHCO_3$ and extracted with $CH_2Cl_2$ (3×100 mL), dried over $Na_2SO_4$, and evaporated to dryness to yield 3.25 g (70%) of 2 as white solid. $^1$H NMR (400 MHz, $CDCl_3$) δ ppm 7.15-7.36 (m, 1H), 7.42-7.62 (m, 2H), 7.63-7.78 (m, 1H), 8.54-8.76 (m, 1H).

4-Chloro-8-((4-methoxybenzyl)oxy)quinoline (23)

A mixture of compound 22 (3.20 g, 17.82 mmol), p-methoxybenzyl chloride (8.37 g, 53.45 mmol), $K_2OC_3$ (7.38 g, 53.45 mmol), and n-$Bu_4NI$ (1.65 g, 4.45 mmol) in anhydrous DMF (20 mL) was heated at 80° C. for 10 hours. The reaction mixture was extracted with ethyl acetate (3×100 mL), washed with water, dried over $Na_2SO_4$, filtered, and concentrated. The crude material was purified by silica gel column chromatography (Hexane/EtOAc, 3:2) to give 4.75 g (89%) of 23 as yellow solid. $^1$H NMR (400 MHz, $CDCl_3$) δ ppm 3.81 (s, 3H), 5.38 (s, 2H), 6.78-6.98 (m, 2H), 7.13 (d, 1H, J=7.6 Hz), 7.34-7.60 (m, 4H), 7.80 (d, 1H, J=8.8 Hz), 8.76-8.88 (m, 1H).

8-((4-Methoxybenzyl)oxy)-4-(piperazine-1-yl)quinoline (24)

A mixture of compound 23 (4.70 g, 15.68 mmol) and piperazine (13.63 g, 158.23 mmol) in isopropanol (30 mL)

was refluxed for 46 hours with stirring. Isopropanol was evaporated under vacuo and the reaction mixture was made alkaline using saturated NaHCO$_3$ solution. The aqueous layer was extracted with CH$_2$Cl$_2$ (3×100 mL), dried over Na$_2$SO$_4$, concentrated under vacuo to afford 5.32 g (97%) of compound 24, which was used for the next reaction without further purification. $^1$H NMR (400 MHz, CDCl$_3$) δ ppm 1.73 (bs, 1H), 2.80-3.44 (m, 8H), 3.80 (s, 3H), 5.36 (s, 2H), 6.82-6.94 (m, 2H), 6.99 (d, 1H, J=8 Hz), 7.23-7.35 (m, 1H), 7.44 (d, 2H, J=8.4 Hz), 7.58 (d, 1H, J=8 Hz), 8.76-8.82 (m, 1H).

4-(4-(2-((Cert-Butyldimethylsilyl)oxy)ethyl)piperazine-1-yl)8-((4-methoxybenzyl)oxy)quinoline (25)

A mixture of compound 24 (5.20 g, 14.88 mmol), (2-bromo-ethyl)-tert-butyldimethylsilane (4.27 g, 17.88 mmol), and K$_2$OC$_3$ (6.17 g, 44.70 mmol) in CH$_3$CN (30 mL) was refluxed for 14 hours. Acetonitrile was evaporated under vacuo and the crude material was purified by silica gel column chromatography (Hexane/EtOAc, 3:2) to give 5.20 g (69%) of 25 as white solid. $^1$H NMR (400 MHz, CDCl$_3$) δ ppm 0.01 (s, 6H), 0.83 (s, 9H), 2.59 (t, 2H, J=6 Hz), 2.65-2.84 (m, 4H), 3.05-3.28 (m, 4H), 3.70 (s, 3H), 3.75 (t, 2H, J=6.4 Hz), 5.27 (s, 2H), 6.74-6.85 (m, 3H), 6.90 (d, 1H, J=7.6 Hz), 7.16-7.26 (m, 1H), 7.35 (d, 2H, J=8.8 Hz), 7.47 (d, 1H, J=8.8 Hz); 8.69 (d, 1H, J=5.2 Hz).

2-(4-(8-((4-Methoxybenzyl)oxy)quinoline-4-yl)piperazine-1-yl)ethanol (26)

To a stirred solution of compound 25 (5.1 g, 10.04 mmol) in anhydrous THF (30 mL) was added n-tetrabutylammonium fluoride (2.63 g, 10.04 mmol, 1.0 M solution in THF) at 0° C. The reaction mixture was then stirred at room temperature for 1 hour. THF was evaporated in vacuo, the residue was diluted with CH$_2$Cl$_2$ (50 mL) and washed with water. The water layer was extracted with CH$_2$Cl$_2$ (3×75 mL). The combined organic layer was washed with brine, dried over Na$_2$SO$_4$, and evaporated in vacuo. The crude product was purified by silica gel column chromatography (EtOAc/MeOH, 9:1) to yield 3.60 g (91%) of compound 26 as white solid. $^1$H NMR (400 MHz, CDCl$_3$) δ ppm 2.60-2.75 (m, 2H), 2.76-2.98 (m, 4H), 3.08-3.42 (m, 4H), 3.52-3.75 (m, 2H), 3.80 (s, 3H), 5.36 (s, 2H), 6.76-6.96 (m, 3H), 6.97-7.08 (m, 1H), 7.18-7.37 (m, 1H), 7.38-7.50 (m, 2H), 7.51-7.64 (m, 1H), 8.74-8.86 (m, 1H).

2-(4-(8-((4-Methoxybenzyl)oxy)quinoline-4yl)piperazine-1yl)acetaldehyde (27)

To a stirred solution of oxalyl chloride (1.8 mL, 20.33 mmol) in CH$_2$Cl$_2$ (40 mL) at −78° C. was added DMSO (2.8 mL, 40.66 mmol). The reaction mixture was stirred for 10 minutes followed by addition of compound 26 (4.0 g, 10.16 mmol, solution in 10 mL of CH$_2$Cl$_2$). The reaction mixture was stirred at the same temperature for 12 minutes. Then Et$_3$N (8.4 mL, 60.98 mmol) was added and stirring was continued for another 1 hour and 20 minutes allowing the reaction mixture to come to room temperature. The reaction mixture was quenched by addition of water and extracted with CH$_2$Cl$_2$ (3×75 mL). The combined organic layer was washed with water and brine and finally purified by silica gel column chromatography (EtOAc/MeOH, 9.5:0.5) to yield 3.06 g (77%) of compound 27 as thick oil. $^1$H NMR (400 MHz, CDCl$_3$) δ ppm 2.45-2.90 (m, 4H), 3.02-3.40 (m, 4H), 3.34 (s, 2H), 3.69 (s, 3H), 5.25 (s, 2H), 6.64-7.04 (m, 4H), 7.16-7.56 (m, 4H), 8.60-8.76 (m, 1H), 9.68 (s, 1H).

Procedure A. (±)-N$^6$-(2-(4-(8-((4-Methoxybenzyl)oxy)quinoline-4-yl)piperazine-1-yl)ethyl)-N$^6$-propyl-4,5,6,7-tetrahydrobenzo[d]thiazole-2,6-diamine ((±)-28)

To a stirred solution of compound 27 (1.3 g, 3.32 mmol) in CH$_2$Cl$_2$ (10 mL), (±)-pramipexole (772 mg, 3.65 mmol) was added at room temperature. The reaction mixture was stirred for 1 hour and then NaBH(OAc)$_3$ (1.27 g, 5.98 mmol) was added to it. After stirring for 48 hours saturated solution of NaHCO$_3$ was added to the reaction mixture and it was extracted with CH$_2$Cl$_2$ (3×50 mL). The combined organic layer was washed with water and brine and finally purified by silica gel column chromatography (EtOAc/MeOH, 9:1) to yield 1.36 g (70%) of compound (±)-28 as yellow solid. $^1$H NMR (400 MHz, CDCl$_3$) δ ppm 0.93 (t, 3H, J=7.2 Hz), 1.34-1.92 (m, 3H), 1.96-2.24 (m, 1H), 2.30-3.05 (m, 14H), 3.06-3.50 (m, 5H), 3.79 (s, 3H), 5.00 (bs, 2H), 5.34 (s, 2H), 6.74-6.92 (m, 3H), 6.99 (d, 1H, J=7.6 Hz), 7.25-7.35 (m, 1H), 7.42 (d, 2H, J=8.4 Hz), 7.53 (d, 1H, J=8.4 Hz), 8.77 (d, 1H, J=4.8 Hz).

(−)-N$^6$-(2-(4-(8-((4-Methoxybenzyl)oxy)quinoline-4-yl)piperazine-1-yl)ethyl)-N$^6$-propyl-4,5,6,7-tetrahydrobenzo[d]thiazole-2,6-diamine ((−)-28)

Compound 27 (1.0 g, 2.55 mmol) was treated with (−)-pramipexole (599 mg, 2.81 mmol) and NaBH(OAc)$_3$ (973 mg, 4.59 mmol) by following procedure A. The reaction mixture was purified by silica gel column chromatography (EtOAc/MeOH, 9:1) to yield 1.12 g (75%) of compound (−)-28 as yellow solid. The $^1$H NMR of (−)-28 is similar to compound (±)-28.

(+)-N$^6$-(2-(4-(8-((4-Methoxybenzyl)oxy)quinoline-4-yl)piperazine-1-yl)ethyl)-N$^6$-propyl-4,5,6,7-tetrahydrobenzo[d]thiazole-2,6-diamine ((+)-28)

Compound 27 (700 mg, 1.79 mmol) was treated with (+)-pramipexole (416 mg, 1.97 mmol) and NaBH(OAc)$_3$ (682 mg, 3.22 mmol) by following procedure A. The reaction mixture was purified by silica gel column chromatography (EtOAc/MeOH, 9:1) to yield 713 mg (68%) of compound (+)-8 as yellow solid. The $^1$H NMR of (+)-8 is similar to compound (±)-28.

Procedure B. (±)-4-(4-(2-((2-Amino-4,5,6,7-tetrahydrobenzo[d]-thiazol-6yl)(propyl)amino)ethyl)piperazine-1-yl)quinoline-8-ol ((±)-29)

To a stirred solution of compound (±)-28 (1.20 g, 2.05 mmol) in CH$_2$Cl$_2$ (10 mL), TFA (10 mL) was added at 0° C. The reaction mixture was then stirred at room temperature for 3 hours. TFA was evaporated under vacuo and the salt was recrystallized from EtOH to afford 1.45 g (82%) TFA salt of (±)-29 as yellow solid. Mp: 112-115° C. Anal. Calcd for C$_{32}$H$_{37.5}$F$_{10.5}$N$_6$O$_8$S (3.5 CF$_3$COOH): C, 44.40; H, 4.37; N, 9.71. Found: C, 44.25; H, 4.80; N, 9.70. $^1$H NMR (400 MHz, CD$_3$OD) δ ppm 1.06 (t, 3H, J=7.2 Hz), 1.60-1.98 (m, 2H), 1.98-2.26 (m, 1H), 2.28-2.50 (m, 1H), 2.52-3.60 (m, 15H), 3.62-4.25 (m, 4H), 7.23 (d, 1H, J=6.8 Hz), 7.31 (d, 1H, J=7.6 Hz), 7.56 (t, 1H, J=8 Hz), 7.62 (d 1H, J=8.4 Hz), 8.45 (d, 1H, J=6 Hz). $^{13}$C NMR (100 MHz, CD$_3$OD) δ ppm 10.1, 18.6, 22.3, 22.7, 22.9, 51.3, 52.4, 52.9, 54.1, 59.7, 106.4, 115.2, 115.9, 121.1, 127.4, 130.8, 140.6, 148.5, 161.9.

The TFA salt of (±)-29 (1.20 g, 11.39 mmol) was dissolved in 10 mL of water, free base was made by using NaHCO$_3$ powder which was then extracted with CH$_2$Cl$_2$, dried over Na$_2$SO$_4$, filtered, and evaporated. The greenish solid product was dissolved in EtOH (2 mL) and ethereal HCl was added to it. The crude salt was then filtered, dried, and then purified by recrystallization in EtOH to afford 696 mg (75%) of the HCl salt of compound (±)-29 as yellow solid. Mp=240-245° C. $^1$H NMR (400 MHz, CD$_3$OD) δ ppm 1.08 (t, 3H, J=7.2 Hz), 1.68-2.10 (m, 2H), 2.11-2.38 (m, 1H), 2.40-2.64 (m, 1H), 2.70-2.94 (m, 2H), 2.94-3.48 (m, 4H), 3.48-4.60 (m, 13H), 7.25-7.48 (m, 2H), 7.56-7.79 (m, 2H), 8.60 (d, 1H, J=6.4 Hz). $^{13}$C NMR (100 MHz, CD$_3$OD) δ ppm 11.4, 19.9, 23.1, 23.5, 24.3, 50.1, 52.2, 53.2, 55.0, 61.1, 109.0, 113.2, 116.8, 123.1, 129.8, 134.4, 142.9, 150.2, 163.3.

(−)-4-(4-(2-((2-Amino-4,5,6,7-tetrahydrobenzo[d]-thiazol-6yl)(propyl)amino)ethyl)piperazine-1-yl)quinoline-8-ol ((−)-29)

Compound (−)-28 (1.10 g, 1.87 mmol) was treated with TFA (10 mL), the TFA salt formed was converted to HCl salt by following procedure B. The crude salt was purified by recrystallization in EtOH to afford 919 mg (73%) of the HCl salt of compound (−)-29 as yellow solid. $[α]_D$=−26.3 (c=0.5, CH$_3$OH). Both the $^1$H and $^{13}$C NMR data are similar to compound (±)-29. Anal. Calcd for C$_{26}$H$_{42}$Cl$_5$N$_6$O$_{1.5}$S (5 HCl, 0.5 C$_2$H$_5$OH): 0, 46.47; H, 6.30; N, 12.51. Found: 0, 46.50; H, 6.67; N, 12.21.

(+)-4-(4-(2-((2-Amino-4,5,6,7-Tetrahydrobenzo[α]-thiazol-6yl)(propyl)amino)ethyl)piperazine-1-yl)quinoline-8-ol ((+)-29)

Compound (+)-28 (650 mg, 1.11 mmol) was treated with TFA (8 mL), the TFA salt formed was converted to HCl salt by following procedure B. The crude salt was purified by recrystallization in EtOH to afford 499 mg (67%) of the HCl salt of compound (+)-29 as yellow solid. $[α]_D$=+27.9 (c=0.5, CH$_3$OH). Both the $^1$H and $^{13}$C NMR data are similar to compound (±)-29.

3. Compounds Having Formulae VIIIa and VIIIb

Figure 17:
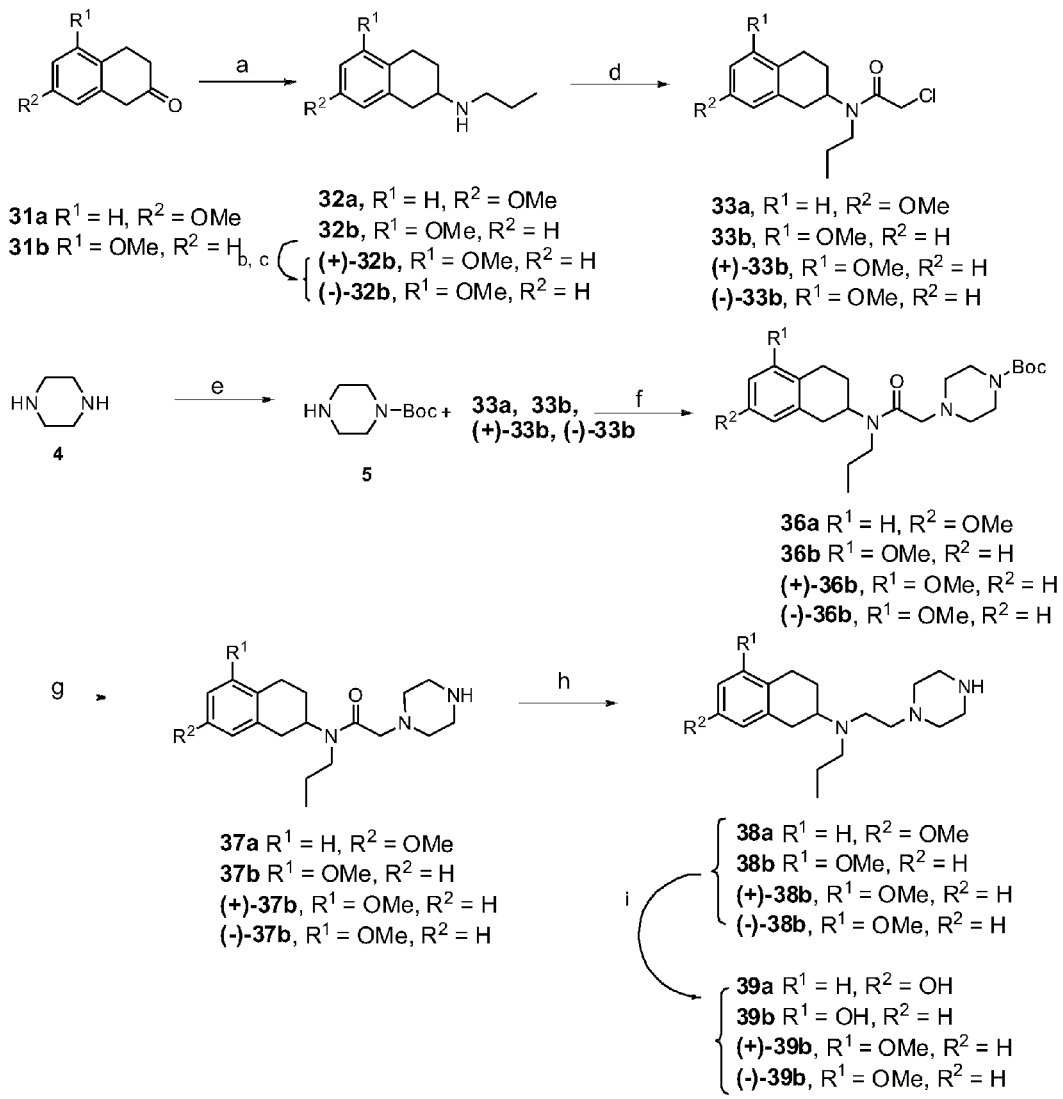
FIG. 17 provides part of a synthetic scheme for preparing compounds of an embodiment of the present invention.

With reference to FIG. 17, scheme 6 outlines the syntheses of compounds 39a, 39b and enantiomerically pure form of 39b, ((+)-39b and (−)-39b). The starting materials for these compounds were appropriately substituted 5- and 7-methoxy-2-tetralones 31a-b. These were condensed with propyl amine under reductive amination conditions to give secondary amines 32a-b, which were then reacted with chloroacetyl chloride to give α-chloro amides 33a-b. Enantiomeric synthesis of compound 39b was performed by converting the racemic amine 32b to its diastereomeric salt by using optically active synthetic resolving agent. The synthesis of this resolving agent (4-(2-chlorophenyl)-5,5-dimethyl-2-hydroxy 1,3,2-dioxaphosphorinane-2-oxide), commonly known as chlocyphos, and its resolution to derive two enantiomers was carried out by following a literature procedure and our earlier publication. Thus, compound 32b was resolved into the enantiomeric pure compound (+)-32b and (−)-32b using (+)- or (−)-chlocyphos by following the procedure reported by us earlier. N-alkylation of amines with mono Boc-protected piperazine gave amides 36a-b, (+)-36a and (−)-36b which were then reduced using lithium aluminum hydride. Demethylation in the presence of boron tribromide afforded phenol intermediates 39a-b, (+)-39b, (−)-39b.

Figure 18:
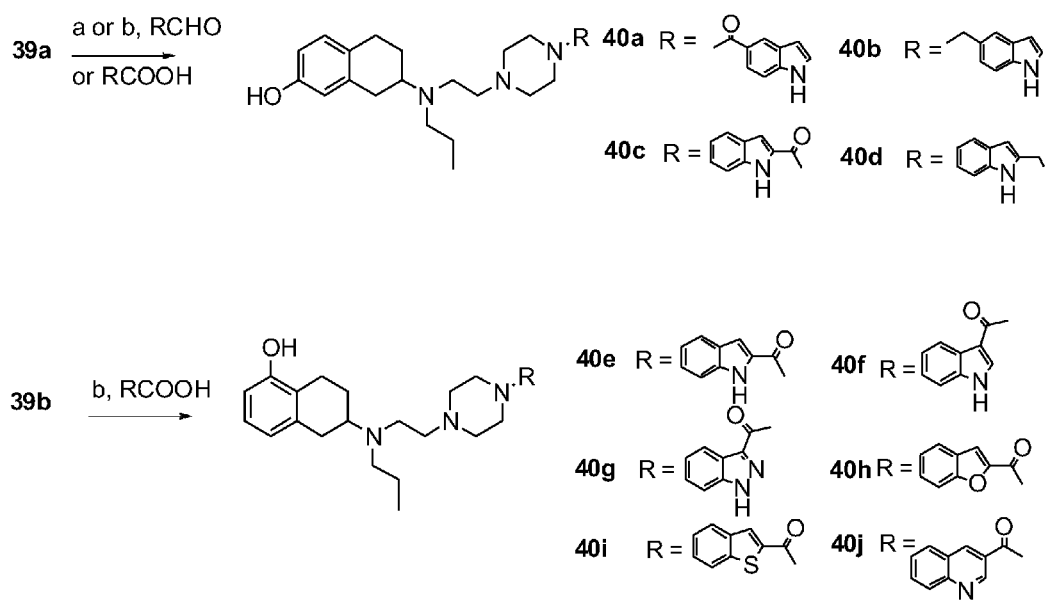
FIG. 18 provides part of a synthetic scheme for preparing compounds of an embodiment of the present invention.

With reference to FIG. 18, Scheme 7 describes the syntheses of indoles 40a-j as well as enantiomeric pure (+)-40e and (−)-40e. Secondary amines 39a-b, (+)-39b and (−)-39b were condensed with either aldehydes under reductive amination conditions or carboxylic acids under amide coupling reactions to yield the final compounds 40a-j, (+)-40e and (−)-40e.

Figure 19:
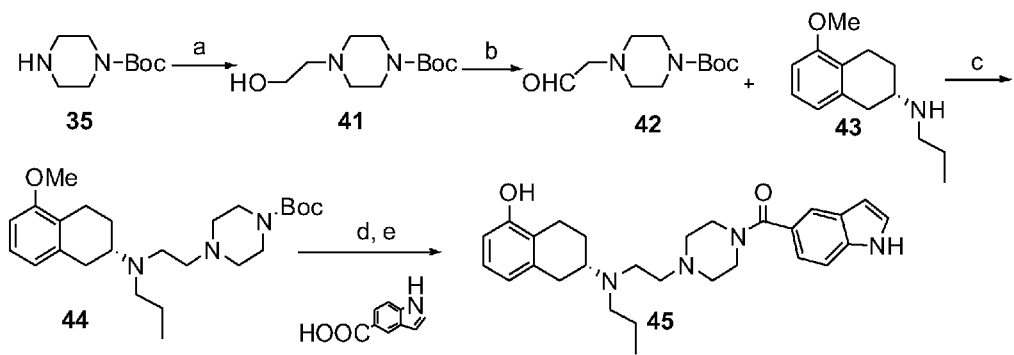
FIG. 19 provides part of a synthetic scheme for preparing compounds of an embodiment of the present invention.

With reference to FIG. 19, the synthesis of optically active indole (−)-45 begins with compound 35 as shown in Scheme 8. N-Alkylation with bromoethanol followed by Swern oxidation gave aldehyde 42. Condensation of 42 with optically active secondary amine 43 afforded 44. Deprotection followed by amide coupling with indole-5-carboxylic acid gave (−)-45.

Figure 20:
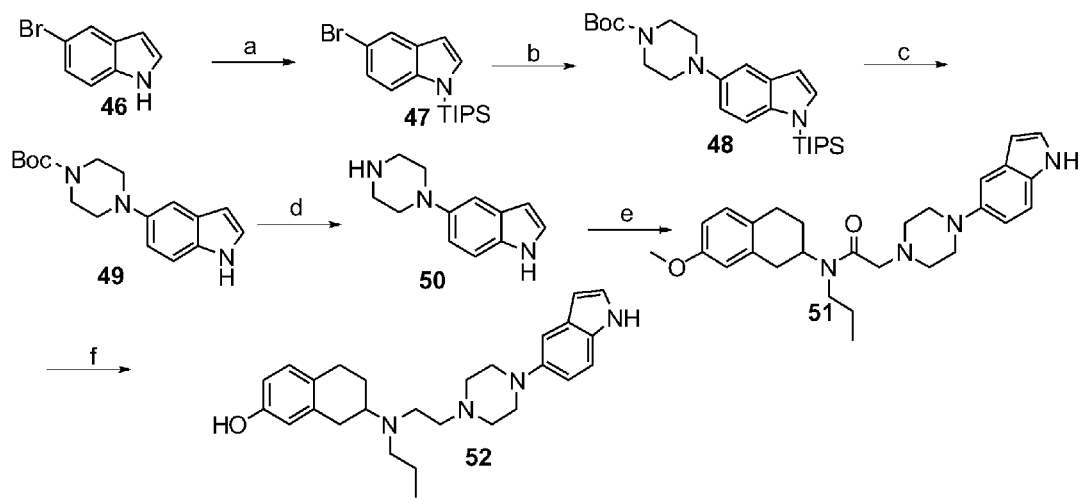
FIG. 20 provides part of a synthetic scheme for preparing compounds of an embodiment of the present invention.

With reference to FIG. 20, Scheme 9 outlines the synthesis of indole 52. 5-Bromoindole was protected using triisopropylsilyl chloride in the presence of NaH to provide 47. Coupling of this compound with 36 using PdCl$_2$[P(o-tol)$_3$]$_2$ and sodium t-butoxide in xylenes gave intermediate 48 in good yield. Next, cleavage of both amine protecting groups followed by condensation with a-chloro amide 33a gave 51. Amide reduction with borane and demethylation using HBr completed the synthesis of 52.

The compounds described by Formulae VIIIa and VIIIb provide a series of N-piperazine substituted novel hybrid derivatives. The majority of compounds designed represent various substituted indole derivatives with additional compounds falling in the category of bioisosteric analogues of indole.

With reference to FIG. 21, Table 4 summarizes the binding data for the indole analogs that were synthesized. Compound 40e, which is a 5-hydroxy aminotetralin compound with a 2-substituted indole amide, proved to be twice as potent in binding at D2 receptors and almost seven times more potent at D3 receptors (K$_i$ D2=51.2 nM, D3=0.550 nM) than its corresponding 7-OH counterpart 40c (K$_i$ D2=116 nM, D3=3.72 nM). The observed differences in D2 binding affinities between 40c and 40e correlate well with parent hybrid compounds D-315 and D-237 (see Table 4). However, the differences in D3 binding between 40c and 40e are more significant than between D-315 and D-237. Thus, the selectivity of 40e for D3 receptor is much higher than 40c (D2/D3; 93 Vs. 31 for 40e and 40c, respectively). On the other hand, the 5-hydroxy derived 3-substituted indole-acyl derivative 40f showed less affinity for D3 receptors compared to its 2-substituted indole 40e counterpart (Ki; 58.9 and 3.62 nM for D2 and D3 receptors, respectively for 40f). The other 5-substituted indole amide derivative 40a derived from the 7-hydroxy series, exhibited higher affinity than its 40c counterpart in the same series (see Table 4). Compounds 45 and 40a exhibited comparable affinity for the D3 receptor (Ki; 2.27 Vs. 1.67 nM, respectively).

Next a series of bioisosteric analogues of 5-hydroxy indole derivative was designed and synthesized. The benzo[b] thiophene derivative 40i showed high affinity for D2 and D3 receptors (K$_i$=76.9 and 1.69 nM for D2 and D3 receptors, respectively). On the other hand, the benzofuran derivative 40h was two- to three-fold less potent in binding compared to 40i (Ki=132 and 5.23 nM for D2 and D3 receptors). The quinoline derivative 40j exhibited similar binding potency as 40h and was the least potent at D2 receptors in this bioisosteric series, with a K$_i$ value of 158 nM. Interestingly, the indazole derivative 40g exhibited the highest affinity for D2 in this current series of molecules and was also among the D3 compounds with highest binding potency in this bioisosteric series of compounds ($K_i$=28 & 2.83 nM for D2 and D3, respectively).

5-Substituted indole derivative 40b, with a methylene unit between the heterocycle and the piperazine fragment, showed affinity for both D2 and D3 that was half as compared to its amide counterpart 40a (Ki; 144 and 3.87 nM for D2 and D3 receptors, respectively for 40b). However, such a change in binding affinity was not observed between the 2-substituted similar indole compounds 40c and 40d. The reason for this is not fully understood. Compound 52, in which the piperazine moiety is directly attached to the 5-position of indole, demonstrated high affinity for both D2 and D3 ($K_i$ D2=30 nM, D3=2 nM).

The above data demonstrates that the position of attachment to the indole moiety influences the binding affinity profiles for both D2 and D3 receptors. For example, changing the point of indole attachment from the 2 position (40e) to the 3 position (40f) results in a very minor shift in $K_i$ values for D2 receptor (51.2 nM for 40e vs 58.9 nM for 40f). However, the 2-substituted indole amide 40e was seven fold more potent than 40f for binding interaction with D3 receptors (Ki; 0.55 vs. 3.62 nM). It will be interesting to investigate in the future whether such changes in affinities can be accounted for by alteration of any electronic properties in the two substituted indoles or other factors. From a structural point of view, it seems that the role of the indole N-atom is less critical here, especially in 40e. Our data also show that the nature of the indole group substitution coupled with the position of the hydroxyl group substitution in the aromatic ring play important roles in determining the D2/D3 binding affinities of hybrid aminotetralin arylpiperazine molecules as well as their selectivity.

As mentioned above, compound 40e is the most potent and selective molecule in binding to D3 receptors in the current series of molecules. Synthesis of enantiomers of 40e was carried out followed by characterization of their binding to D2/D3 receptors. As expected, (−)-40e exhibited higher affinity and selectivity for D2/D3 receptors than its corresponding enantiomeric counterpart (+)-40e ($K_i$, 47.5 nM and 0.57 nM vs. 113 nM and 3.73 nM for D2 and D3 receptors, respectively). In this regard, (−)-40e exhibited higher affinity and selectivity for the D3 receptor compared to either (±)-7-OH-DPAT or (−)-5-OH-DPAT (Ki; 0.57 nM Vs 6.19 nM and 1.36 nM; D2/D3: 83 vs. 50 and 43). Compound (−)-45 (Ki; 157 nM and 2.27 nM for D2 and D3, respectively) was selectively synthesized as our current results and previous results consistently demonstrated that in the 5-hydroxy series of hybrid compound, it is the (−)-isomeric version which exhibits the highest affinity for the D3 receptor compared to the (+)-version. Another interesting aspect of the results from current SAR studies concerns the role of piperazine N-atoms in interacting with D2/D3 receptors. The piperazine N-atom connected to the aromatic moiety in compound D-264 and D-237 is expected to be less basic compared to the other piperazine N-atom. In the current indole amides and other heterocyclic amide derivatives this N-atom is expected to be even lesser basic in nature. However, this loss of basicity has not impacted their affinity for D2/D3 receptors, possibly indicating very little or no involvement of this N-atom in H-bonding and ionic interaction with the target receptors.

Next, we evaluated one of the optically active lead compounds (−)-45 and the reference (−)-5-OH-DPAT in the GTPγS functional assay for D2 and D3 receptors. The assay was carried out with cloned human D2 and D3 receptors expressed in CHO- and AtT-cells, respectively. The half maximal stimulation (EC50) exhibited by (−)-45 at D2 receptors was in the nanomolar range and at D3 receptors subnanomolar (EC50; 10.4 and 0.14 nM for D2 and D3 receptor, respectively) whereas the compound maximally stimulated the GTPγS signal comparable to the full agonist dopamine itself, indicating full agonist activity at both D2 and D3 receptor. The functional data shows that (−)-45 has a preferential intrinsic stimulatory effect at D3 receptors compared to D2 receptors (D2/D3 (EC50)=74) (FIG. 22, Table 5).

The compounds of Formulae VIIIa and VIIIb show that in order to maintain high affinity and selectivity for the D3 receptor, the heterocyclic ring does not need to be connected directly to the piperazine ring as the majority of compounds included here are linked either via an amide or a methylene linker. Thus, compound (−)-40e with an amide linker connected to the 2-position of the indole ring was among the compounds with high affinity and selectivity at the D3 receptor. Moreover, compound (−)-40e was more potent and selective for the D3 receptor compared to either 7-OH-DPAT or 5-OH-DPAT. As found from our previous studies on hybrid compounds, compounds belonging to 5-hydroxy series in general produced higher potency than those in the 7-hydroxy series. Among the bioisosteric derivatives, the indazole derivative 40g and benzo[b]thiazole 40i exhibited the highest affinity for D2 and D3 receptors. In the functional GTPγS studies, compound (−)-40e exhibited good selectivity at the D3 receptor, conforming to its binding data. Our current ongoing SAR studies will shed more light in regards to the interaction of hybrid molecules which will be used to develop a pharmacophore model for these compounds.

Analytical silica gel-coated TLC plates (Silica Gel 60 $F_{254}$) were purchased from EM Science and were visualized with UV light or by treatment with either phosphomolybdic acid (PMA) or ninhydrin. Flash chromatography was carried out on Baker Silica Gel 40 mM. 1H NMR spectra were routinely obtained on GE-300 MHz and Varian 400 MHz FT NMR. The NMR solvent used was either $CDCl_3$ or $CD_3OD$ as indicated. TMS was used as an internal standard. Elemental analyses were performed by Atlantic Microlab, Inc. and were within ±0.4% of the theoretical value. Optical rotations were recorded on a Perkin Elmer 241 polarimeter. [3H]spiperone (15.0 Ci/mmole) and [35S]GTPS (1250 Ci/mmole) were from Perkin Elmer (Boston, Mass.). 7-OHDPAT, and (+)-butaclamol were from Sigma-Aldrich (St. Louis, Mo.).

Procedure A. (7-Methoxy-1,2,3,4-tetrahydro-naphthalen-2-yl)-propyl-amine (32a)

7-Methoxy-2-tetralone (6.21 g, 35.2 mmol) and acetic acid (5.3 ml, 105.6 mmol) were dissolved in dichloroethane (100 ml) and cooled to 0° C. Propyl amine (5.7 ml, 70.4 mmol) was added and the mixture was stirred under a $N_2$ atmosphere for 30 min. $NaCNBH_3$ (5.5 g, 80.8 mmol) in anhydrous MeOH (15 ml) was then added to the mixture and allowed to stir overnight at ambient temperature. The volatiles were then evaporated and the mixture was partioned between ethyl acetate and 1 M NaOH. The organic layer was separated, dried ($Na_2SO_2$), filtered, and concentrated. The crude residue was then taken up in EtOAc, at which time ethereal HCl was added, and the material evaporated to dryness. The crude salt was dissolved in a minimum volume of MeOH, and precipitated by the gradual addition of diethyl ether. The salt was collected via filtration and dried to yield 5.09 g (64%, free base) and used in the subsequent transformations. $^1$H NMR (free base) (400 MHz, $CDCl_3$) 0.91-0.95 (t, 3H, J=7.6 Hz), 1.38 (bs, 1H), 1.48-1.60 (m, 3H), 2.04-2.09 (m, 1H), 2.54-2.62 (m, 2H), 2.67-2.71 (t, 3H, J=7.6 Hz), 2.88-2.92 (m, 2H), 2.97-3.04 (m, 1H), 3.81 (s, 3H), 6.60-6.61 (dd, 1H, J=1.6 Hz), 6.65-6.78 (m, 1H), 6.95-6.98 (d, 1H, J=8.8 Hz).

(5-Methoxy-1,2,3,4-tetrahydro-naphthalen-2-yl)-propyl-amine (32b)

This compound was prepared following Procedure A from 5-methoxy 2-tetralone (6.0 g, 34.0 mmol), acetic acid (5.1 ml, 102 mmol), propyl amine (5.5 ml, 68 mmol), and NaCNBH$_3$ (5.3 g, 85 mmol) to give 4.63 g of 32b (62%, free base). $^1$H NMR (free base) (400 MHz, CDCl$_3$) 0.92-0.964 (t, 3H, J=7.6 Hz), 1.39 (bs, 1H), 1.49-1.61 (m, 3H), 2.05-2.10 (m, 1H), 2.53-2.62 (m, 2H), 2.66-2.70 (t, 3H, J=7.6 Hz), 2.87-2.94 (m, 2H), 2.98-3.03 (m, 1H), 3.81 (s, 3H), 6.65-6.67 (d, 1H, J=8 Hz), 6.96-6.71 (d, 1H, J=8 Hz), 7.07-7.11 (t, 1H, J=7.2 Hz).

Compound 32b was resolved into its enantiomerically pure form (+)-32b and (−)-32b following the procedure reported by us earlier.

Procedure B: 2-Chloro-N-(7-methoxy-1,2,3,4-tetrahydro-naphthalen-2-yl)-N-propyl-acetamide (33a)

Compound 32a (HCl salt, 5.0 g, 19.5 mmol) and Et$_3$N (5.5 ml, 39.1 mmol) was stirred at 0° C. in CH$_2$Cl$_2$ (65 ml) for 15 min. Chloroacetyl chloride (1.9 ml, 23.5 mmol) was added dropwise and the resulting solution was stirred at room temperature for 20 min, at which time the reaction mixture was poured into a 1M solution of NaOH (50 ml) and the product was extracted with dichloromethane, dried (Na$_2$SO$_4$), filtered, and concentrated. The crude material was purified by column chromatography (Hex:EtOAc, 3:1) to give 5.5 g (95%) of 33a. $^1$H NMR (400 MHz, CDCl$_3$) 0.90-0.98 (m, 3H), 1.64-1.72 (m, 2H), 3.19-3.27 (m, 2H), 4.00 (s, 3H), 6.61-6.62 (dd, 1H, J=1.6 Hz), 6.64-6.77 (m, 1H), 6.96-6.99 (d, 1H, J=8.8 Hz).

2-Chloro-N-(5-methoxy-1,2,3,4-tetrahydro-naphthalen-2-yl)-N-propyl-acetamide (33b)

This compound was prepared from 32b (4.63 g, 21.1 mmol), triethyl amine (5.1 ml, 42.2 mmol), and chloroacetyl chloride (1.80 ml, 25.4 mmol) by following Procedure B to give 33b (5.8 g, 93%). $^1$H NMR (400 MHz, CDCl$_3$) 0.90-0.98 (m, 3H), 1.64-1.72 (m, 2H), 3.19-3.27 (m, 2H), 4.00 (s, 3H), 6.61-6.68 (m, 2H), 6.96-7.04 (m, 1H).

(+)-2-Chloro-N-(5-methoxy-1,2,3,4-tetrahydro-naphthalen-2-yl)-N-propyl-acetamide ((+)-33b)

This compound was prepared from (+)-32b (3.09 g, 14.07 mmol), triethyl amine (3.4 ml, 28.1 mmol), and chloroacetyl chloride (1.20 ml, 16.93 mmol) by following Procedure B to give (+)-33b (3.95 g, 95%). $^1$H NMR (400 MHz, CDCl$_3$) 0.90-0.97 (m, 3H), 1.65-1.72 (m, 2H), 3.18-3.27 (m, 2H), 4.00 (s, 3H), 6.607-6.68 (m, 2H), 6.97-7.03 (m, 1H).

(−)-2-Chloro-N-(5-methoxy-1,2,3,4-tetrahydro-naphthalen-2-yl)-N-propyl-acetamide ((−)-33b)

This compound was prepared from (−)-32b (1.98 g, 9.02 mmol), triethylamine (2.2 ml, 18 mmol), and chloroacetyl chloride (0.77 ml, 10.85 mmol) by following Procedure B to give (−)-33b (2.50 g, 96%). $^1$H NMR (400 MHz, CDCl$_3$) 0.87-0.95 (m, 3H), 1.63-1.78 (m, 2H), 3.1-20-3.30 (m, 2H), 3.89 (s, 3H), 6.61-6.68 (m, 2H), 6.97-7.02 (m, 1H).

Procedure C: 4-{[(7-Methoxy-1,2,3,4-tetrahydro-naphthalen-2-yl)-propyl-carbamoyl]-methyl}-piperazine-1-carboxylic acid tert-butyl ester (36a)

Compound 33a (4.22 g, 14.3 mmol), 35 (4.35 g, 17.2 mmol), K$_2$OC$_3$ (3.94 g, 28.5 mmol) were refluxed in CH$_3$CN (100 ml) for 1 hr. The solution was cooled, filtered, and concentrated. The crude material was then partitioned between EtOAc and H$_2$O, and the organic layer was separated, dried (Na$_2$SO$_4$), and concentrated. The crude mixture was purified by column chromatography (EtOAc) to give 5.1 g (71%) of 36a. $^1$H NMR (400 MHz, CDCl$_3$) 0.86-0.90 (t, 3H, J=8 Hz), 1.45 (s, 9H), 1.59-1.82 (m, 2H), 1.87-1.94 (m, 1H), 1.95-1.97 (m, 3H), 2.420 (bs, 2H), 2.50-2.63 (m, 2H), 2.76-2.82 (m, 1H), 2.96-3.20 (m, 3H), 3.88-3.47 (m, 4H), 3.81 (s, 3H), 6.60-6.61 (dd, 1H, J=1.6 Hz), 6.65-6.78 (m, 1H), 6.95-6.98 (d, 1H, J=8.8 Hz).

4-{[(5-Methoxy-1,2,3,4-tetrahydro-naphthalen-2-yl)-propyl-carbamoyl]-methyl}-piperazine-1-carboxylic acid tert-butyl ester (36b)

This compound was prepared from 33b (5.8 g, 19.6 mmol), 35 (5.9 g, 23.6 mmol), and K$_2$OC$_3$ (5.4 g, 41.2 mmol) according to Procedure C for to give 36b (6.6 g, 74%). $^1$H NMR (400 MHz, CDCl$_3$) 0.87-0.91 (t, 3H, J=8 Hz), 1.44 (s, 9H), 1.58-1.81 (m, 2H), 1.88-1.95 (m, 1H), 1.96-1.98 (m, 3H), 2.40 (bs, 2H), 2.51-2.63 (m, 2H), 2.78-2.83 (m, 1H), 2.95-3.29 (m, 3H), 3.88-3.47 (m, 4H), 3.81 (s, 3H), 6.63-6.70 (m, 2H), 7.10-7.14 (t, 1H, J=7.2 Hz).

(+)-4-{[(5-Methoxy-1,2,3,4-tetrahydro-naphthalen-2-yl)-propyl-carbamoyl]-methyl}-piperazine-1-carboxylic acid tert-butyl ester ((+)-36b)

This compound was prepared from (+)-33b (5.22 g, 17.64 mmol), 35 (5.31 g, 21.24 mmol), and K$_2$OC$_3$ (4.86 g, 37.08 mmol) according to the Procedure C for to give (+)-36b (5.52 g, 69%). $^1$H NMR (400 MHz, CDCl$_3$) 0.87-0.91 (t, 3H, J=8 Hz), 1.45 (s, 9H), 1.60-1.81 (m, 2H), 1.88-1.94 (m, 1H), 1.96-2.00 (m, 3H), 2.40 (bs, 2H), 2.51-2.65 (m, 2H), 2.78-2.82 (m, 1H), 2.99-3.28 (m, 3H), 3.39-3.47 (m, 4H), 3.81 (s, 3H), 6.63-6.70 (m, 2H), 7.10-7.13 (t, 1H, J=7.2 Hz).

(−)-4-{[(5-Methoxy-1,2,3,4-tetrahydro-naphthalen-2-yl)-propyl-carbamoyl]-methyl}-piperazine-1-carboxylic acid tert-butyl ester ((−)-36b)

This compound was prepared from 33b (2.23 g, 7.54 mmol), 35 (2.26 g, 9.08 mmol), and K$_2$OC$_3$ (2.08 g, 15.85 mmol) according to the Procedure C for to give 36b (2.62 g, 76%). $^1$H NMR (400 MHz, CDCl$_3$) 0.87-0.92 (t, 3H, J=8 Hz), 1.44 (s, 9H), 1.58-1.82 (m, 2H), 1.88-1.97 (m, 1H), 1.96-2.00 (m, 3H), 2.41 (bs, 2H), 2.51-2.60 (m, 2H), 2.78-2.85 (m, 1H), 2.95-3.31 (m, 3H), 3.88-3.46 (m, 4H), 3.81 (s, 3H), 6.63-6.70 (m, 2H), 7.10-7.13 (t, 1H, J=7.2 Hz).

Procedure D: N-(7-Methoxy-1,2,3,4-tetrahydro-naphthalen-2-yl)-2-piperazin-1-yl-N-propyl-acetamide (37a)

Compound 36a (5.1 g, 11.5 mmol) was dissolved in 40 ml of dichloromethane and 40 ml of trifluoroacetic acid was added. The mixture was stirred for 3 hr, at which time the solution was concentrated to dryness, dissolved in sat. NaHCO$_3$, and extracted with EtOAc. The organic layer was dried (Na$_2$SO$_4$), filtered, and concentrated to yield 3.8 g (96%) of 37a, which was used as is in the next reaction. $^1$H NMR (400 MHz, CDCl$_3$) 0.93-0.96 (t, 3H, J=7.6 Hz), 1.62 (m, 3H), 1.85-1.97 (m, 3H), 2.56 (m, 1H), 2.81-2.88 (m, 5H), 2.98-3.34 (m, 9H), 3.81 (s, 3H), 6.60-6.61 (dd, 1H, J=1.6 Hz), 6.65-6.78 (m, 1H), 6.95-6.98 (d, 1H, J=8.8 Hz).

N-(5-Methoxy-1,2,3,4-tetrahydro-naphthalen-2-yl)-2-piperazin-1-yl-N-propyl-acetamide (37b)

This compound was prepared from 36b (6.6 g, 14.8 mmol), and TFA (40 ml) by following Procedure D to give 37b (4.8 g, 92%). $^1$H NMR (400 MHz, CDCl$_3$) 0.92-0.964 (t, 3H, J=7.6 Hz), 1.63 (m, 3H), 1.84-1.97 (m, 3H), 2.55 (m, 1H), 2.80-2.87 (m, 5H), 2.97-3.34 (m, 9H), 3.82 (s, 3H), 6.64-6.71 (m, 2H), 7.06-7.15 (m, 1H).

(+)-N-(5-Methoxy-1,2,3,4-tetrahydro-naphthalen-2-yl)-2-piperazin-1-yl-N-propyl-acetamide ((+)-37b)

This compound was prepared from (+)-36b (1.65 g, 3.70 mmol), and TFA (10 ml) by following the Procedure D to give (+)-37b (1.22 g, 94%). $^1$H NMR (400 MHz, CDCl$_3$) 0.92-0.97 (t, 3H, J=7.6 Hz), 1.62-1.64 (m, 3H), 1.84-1.98 (m, 3H), 2.52-2.55 (m, 1H), 2.80-2.89 (m, 5H), 2.97-3.35 (m, 9H), 3.82 (s, 3H), 6.64-6.70 (m, 2H), 7.06-7.14 (m, 1H).

(−)-N-(5-Methoxy-1,2,3,4-tetrahydro-naphthalen-2-yl)-2-piperazin-1-yl-N-propyl-acetamide ((−)-37b)

This compound was prepared from (−)-36b (1.38 g, 3.08 mmol), and TFA (10 ml) by following the Procedure D to give (−)-37b (1.02 g, 94%). $^1$H NMR (400 MHz, CDCl$_3$) 0.91-0.97 (t, 3H, J=7.6 Hz), 1.62-1.65 (m, 3H), 1.84-1.95 (m, 3H), 2.56 (m, 1H), 2.80-2.88 (m, 5H), 2.97-3.35 (m, 9H), 3.80 (s, 3H), 6.64-6.70 (m, 2H), 7.06-7.16 (m, 1H).

Procedure E: (7-Methoxy-1,2,3,4-tetrahydro-naphthalen-2-yl)-(2-piperazin-1-yl-ethyl)-propyl-amine (38a)

To a suspension of LiAlH$_4$ (1.6 g, 40.5 mmol) in THF (100 ml) in an ice bath was added 37a (3.8 g, 11.0 mmol) dissolved in a solution of THF (25 ml). After addition, the mixture was refluxed for 3 hrs and cooled to 0° C. 10% NaOH was added dropwise, and the mixture stirred for 20 min, and filtered. The solution was dried (Na$_2$SO$_4$), filtered, and concentrated to give 38a (3.21 g, 97%), which was used without further purification. $^1$H NMR (400 MHz, CDCl$_3$) 0.91-0.96 (t, 3H, J=7.6 Hz), 1.40-1.59 (m, 3H), 1.97-2.22 (m, 1H), 2.41-3.11 (m, 19H), 3.82 (s, 3H), 5.2 (bs, 1H), 6.61-6.62 (dd, 1H, J=1.6 Hz), 6.66-6.79 (m, 1H), 6.96-6.99 (d, 1H, J=8.8 Hz).

(5-Methoxy-1,2,3,4-tetrahydro-naphthalen-2-yl)-(2-piperazin-1-yl-ethyl)-propyl-amine (38b)

This compound was prepared from 37b (4.8 g, 13.8 mmol) and LiAlH$_4$ (2.0 g, 55.2 mmol) by following Procedure E to give 38b (4.2 g, 91%). $^1$H NMR (400 MHz, CDCl$_3$) 0.92-0.96 (t, 3H, J=7.6 Hz), 1.41-1.59 (m, 3H), 1.98-2.22 (m, 1H), 2.41-3.1 (m, 19H), 3.81 (s, 3H), 5.2 (bs, 1H), 6.58-6.60 (d, 1H, J=8 Hz), 6.70-6.72 (d, 1H, J=8 Hz), 7.04-7.1 (t, 1H, J=8 Hz).

(+)-5-Methoxy-1,2,3,4-tetrahydro-naphthalen-2-yl)-(2-piperazin-1-yl-ethyl)-propyl-amine ((+)-38b)

This compound was prepared from (+)-37b (1.22 g, 3.51 mmol) and LiAlH$_4$ (0.510 g, 14.05 mmol) by following the Procedure E to give (+)-38b (1.00 g, 85%). $^1$H NMR (400 MHz, CDCl$_3$) 0.92-0.97 (t, 3H, J=7.6 Hz), 1.41-1.60 (m, 3H), 1.98-2.24 (m, 1H), 2.41-3.12 (m, 19H), 3.80 (s, 3H), 5.22 (bs, 1H), 6.58-6.61 (d, 1H, J=8 Hz), 6.70-6.73 (d, 1H, J=8 Hz), 7.04-7.11 (t, 1H, J=8 Hz).

(−)-5-Methoxy-1,2,3,4-tetrahydro-naphthalen-2-yl)-(2-piperazin-1-yl-ethyl)-propyl-amine ((−)-38b)

This compound was prepared from (−)-37b (1.02 g, 2.93 mmol) and LiAlH$_4$ (0.42 g, 11.72 mmol) by following the Procedure E to give (−)-38b (0.90 g, 92%). $^1$H NMR (400 MHz, CDCl$_3$) 0.92-0.98 (t, 3H, J=7.6 Hz), 1.41-1.61 (m, 3H), 1.98-2.20 (m, 1H), 2.40-3.20 (m, 19H), 3.83 (s, 3H), 5.19 (bs, 1H), 6.58-6.60 (d, 1H, J=8 Hz), 6.70-6.72 (d, 1H, J=8 Hz), 7.04-7.12 (t, 1H, J=8 Hz).

Procedure F: 7-[(2-Piperazin-1-yl-ethyl)-propyl-amino]-5,6,7,8-tetrahydro-naphthalen-2-ol (39a)

Compound 38a (3.21 g, 9.70 mmol) was dissolved in 120 ml of CH$_2$Cl$_2$ and cooled to −78° C. 1M boron tribromide (30 ml) was added dropwise and the mixture was allowed to warm to ambient temperature and was stirred overnight. Sat. NaHCO$_3$ was added and the product extracted with dichloromethane, dried (Na$_2$SO$_4$), filtered, and concentrated to yield the crude product. Column chromatography (7:3:1 CH$_2$Cl$_2$:MeOH:Et$_3$N) afforded 2.41 g (84%) of 39a. $^1$H NMR (400 MHz, CDCl$_3$) 0.98-1.02 (t, 3H, 7.6 Hz), 1.27-1.31 (m, 2H), 1.70-1.82 (m, 3H), 2.25-2.28 (m, 1H), 2.58-2.06 (m, 1H), 2.73-2.78 (m, 4H), 2.97-3.09 (m, 5H), 3.16-3.20 (m, 9H), 6.45 (s, 1H), 6.53-6.55 (d, 1H, J=9.2 Hz), 6.84-6.85 (d, 1H, J=8.4 Hz).

6-[(2-Piperazin-1-yl-ethyl)-propyl-amino]-5,6,7,8-tetrahydro-naphthalen-1-ol (39b)

This compound was prepared from 38b (4.2 g, 12.6 mmol), and boron tribromide (39 ml) following Procedure F to give 39b (3.1 g, 78%). $^1$H NMR (400 MHz, CDCl$_3$) 0.99-1.02 (t, 3H, 7.6 Hz), 1.28-1.30 (m, 2H), 1.71-1.83 (m, 3H), 2.26-2.29 (m, 1H), 2.57-2.06 (m, 1H), 2.72-2.77 (m, 4H), 2.97-3.07 (m, 5H), 3.16-3.21 (m, 9H), 6.58-6.59 (d, 1H, J=8 Hz), 6.61-6.28 (m, 1H, J=8 Hz), 6.92-6.95 (t, 1H, J=Hz).

(+)-6-[(2-Piperazin-1-yl-ethyl)-propyl-amino]-5,6,7,8-tetrahydro-naphthalen-1-ol ((+)-39b)

This compound was prepared from (+)-38b (1.00 g, 3.00 mmol), and boron tribromide (10 ml) by following the Procedure F to give (+)-39b (0.78 g, 82%). $^1$H NMR (400 MHz, CDCl$_3$) 0.99-1.02 (t, 3H, 7.6 Hz), 1.28-1.32 (m, 2H), 1.73-1.83 (m, 3H), 2.24-2.29 (m, 1H), 2.57-2.07 (m, 1H), 2.73-2.77 (m, 4H), 2.97-3.06 (m, 5H), 3.16-3.20 (m, 9H), 6.58-6.60 (d, 1H, J=8 Hz), 6.59-6.28 (m, 1H, J=8 Hz), 6.92-6.97 (t, 1H, J=Hz).

(−)-6-[(2-Piperazin-1-yl-ethyl)-propyl-amino]-5,6,7,8-tetrahydro-naphthalen-1-ol ((−)-39b)

This compound was prepared from (−)-38b (0.90 g, 2.70 mmol), and boron tribromide (9 ml) by following the Procedure F to give (−)-39b (0.62 g, 73.3%). $^1$H NMR (400 MHz, CDCl$_3$) 0.99-1.02 (t, 3H, 7.6 Hz), 1.28-1.30 (m, 2H), 1.71-1.82 (m, 3H), 2.24-2.29 (m, 1H), 2.57-2.08 (m, 1H), 2.72-

2.77 (m, 4H), 2.97-3.09 (m, 5H), 3.16-3.23 (m, 9H), 6.58-6.59 (d, 1H, J=8 Hz), 6.61-6.27 (m, 1H, J=8 Hz), 6.92-6.96 (t, 1H, J=Hz).

Procedure G. (4-{2-[(7-Hydroxy-1,2,3,4-tetrahydro-naphthalen-2-yl)-propyl-amino]-ethyl}-piperazin-1-yl)-(1H-indol-5-yl)-methanone (40a)

Indole-5-carboxylic acid (30 mg, 0.19 mmol), EDCI (45 mg, 0.24 mmol), HOBT (31 mg, 0.24 mmol), triethylamine (31 mg, 0.32 mmol), and compound 39a (50 mg, 0.16 mmol) were dissolved in dry $CH_2Cl_2$ (10 ml) and stirred at ambient temperature overnight. The mixture was poured into sat. NaHCO3 and extracted with dichloromethane. The organic extract was dried ($Na_2SO_4$), filtered and concentrated to yield the crude product. Column chromatography afforded 40a (26 mg, 37%). $^1$H NMR (400 MHz, $CDCl_3$) δ 0.87 (t, 3H, J=7.2 Hz), 1.40-1.54 (m, 3H), 1.93 (d, 1H, J=10.0 Hz), 2.45-2.78 (m, 14H), 2.86-2.91 (m, 1H), 3.70 (m, 4H), 6.45 (d, 1H, J=2.0 Hz), 6.55-6.58 (m, 2H), 6.87 (d, 1H, J=8.0 Hz), 7.21-7.24 (m, 2H), 7.33 (d, 1H, J=8.4 Hz), 7.71 (s, 1H), 8.79 (1H, bs). The free base of 40a was converted into oxalate salt. m.p. 194-199° C. Anal. [$C_{28}H_{38}N_4O.2.0(COOH)_2$] C, H, N.

7-({2-[4-(1H-Indol-5-ylmethyl)-piperazin-1-yl]-ethyl}-propyl-amino)-5,6,7,8-tetrahydro-naphthalen-2-ol (40b)

Compound 40b was prepared according to Procedure A using 39a (65 mg, 0.20 mmol) and indole-5-carboxaldehyde (35 mg, 0.24 mmol) to give 40b (29 mg, 32%) after column chromatography. $^1$H NMR (400 MHz, $CDCl_3$) δ 0.84 (t, 3H, J=7.2 Hz), 1.33-1.44 (m, 3H), 1.85 (d, 1H, J=10.0 Hz), 2.41-2.82 (m, 19H), 3.60 (s, 2H), 6.35 (d, 1H, J=2.0 Hz), 6.49-6.58 (m, 2H), 6.85 (d, 1H, J=8.4 Hz), 7.14-7.20 (m, 2H), 7.31 (d, 1H, J=8.4 Hz), 7.54 (s, 1H), 8.38 (bs, 1H). The free base of 40b was converted into oxalate salt. m.p. 198-203° C. Anal. [$C_{28}H_{38}N_4O.2.5(COOH)_2.3H_2O$] C, H, N.

(4-{2-[(7-Hydroxy-1,2,3,4-tetrahydro-naphthalen-2-yl)-propyl-amino]-ethyl}-piperazin-1-yl)-(1H-indol-2-yl)-methanone (40c)

Compound 40c was prepared following Procedure G using 39a (100 mg, 0.32 mmol) and indole-2-carboxylic acid (61 mg, 0.38 mmol) to give 40c (125 mg, 86%) after column chromatography. $^1$H NMR (400 MHz, $CDCl_3$) δ 0.88 (t, 3H, J=7.2 Hz), 1.42-1.64 (m, 3H), 1.94 (brs, 1H), 2.51-2.75 (m, 14H), 2.88-2.96 (m, 1H), 3.95 (brs, 4H), 6.53 (brs, 1H), 6.59-6.61 (m, 1H), 6.75 (s, 1H), 6.90 (d, 1H, J=12.0 Hz), 7.11-7.18 (m, 1H), 7.22-7.26 (m, 1H), 7.40 (d, 1H, J=8.4 Hz), 7.62 (d, 1H, J=8.0 Hz), 9.72 (s, 1H). The free base of 40c was converted into HCl salt. m.p. 203-205° C. Anal. [$C_{28}H_{36}N_4O_2.2HCl.1.2H_2O$] C, H, N.

7-({2-[4-(1H-Indol-2-ylmethyl)-piperazin-1-yl]-ethyl}-propyl-amino)-5,6,7,8-tetrahydro-naphthalen-2-ol (40d)

Compound 40d was prepared according to Procedure A using 39a (100 mg, 0.32 mmol) and 1H-Indole-2-carbaldehyde (100 mg, 0.69 mmol) to give 40d (125 mg, 85%) after column chromatography. $^1$H NMR (400 MHz, $CDCl_3$) δ 0.86 (t, 3H, J=7.2 Hz), 1.39-1.50 (m, 3H), 1.89 (brs, 1H), 2.41-2.73 (m, 18H), 2.82-2.88 (m, 1H), 3.65 (s, 2H), 6.35 (s, 1H), 6.44 (brs, 1H), 6.54-6.57 (m, 1H), 6.87 (d, 1H, J=8.8 Hz), 7.04-7.08 (m, 1H), 7.10-7.16 (m, 1H), 7.30 (d, 1H, J=7.6 Hz), 7.54 (d, 1H, J=8.0 Hz), 8.63 (s, 1H). The free base of 40d was converted into oxalate salt. m.p. 135-137° C. Anal. [$C_{28}H_{38}N_4O.3.0(COOH)_2.0.3H_2O$] C, H, N.

(4-{2-[(5-Hydroxy-1,2,3,4-tetrahydro-naphthalen-2-yl)-propyl-amino]-ethyl}-piperazin-1-yl)-(1H-indol-2-yl)-methanone (40e)

Compound 40e was prepared following Procedure G using 39b (43 mg, 0.14 mmol) and indole-2-carboxylic acid (30 mg, 0.19 mmol) to give 40e (32 mg, 62%) after column chromatography. $^1$H NMR (400 MHz, $CD_3OD$) δ 1.02-1.06 (t, 3H, J=7.2 Hz), 1.77-1.79 (m, 3H), 2.27 (m, 1H), 2.63-2.66 (bs, 4H), 3.03-3.16 (m, 5H), 3.30-3.41 (m, 3H), 3.89 (bs, 4H), 6.59-6.61 (d, 1H, J=7.6 Hz), 6.63-6.65 (d, 1H, J=8 Hz), 6.84 (s, 1H), 6.94-6.98 (t, 1H, J=7.2 Hz), 7.04-7.08 (t, 1H, J=7.2 Hz), 7.19-7.23 (t, 1H, J=7.2 Hz), 7.41-7.61 (d, 1H, J=8 Hz), 7.59-7.61 (d, 1H, J=8 Hz). The free base of 40e was then converted into its HCl salt. m.p. 166-165° C. Anal. [$C_{28}H_{36}N_4O_2.3HCl$] C, H, N.

(+)-(4-{2-[(5-Hydroxy-1,2,3,4-tetrahydro-naphthalen-2-yl)-propyl-amino]-ethyl}-piperazin-1-yl)-(1H-indol-2-yl)-methanone ((+)-40e)

Compound (+)-40e was prepared following the Procedure G using (+)-39b (30 mg, 0.094 mmol) and indole-2-carboxylic acid (23 mg, 0.14 mmol) to give 40e (18.5 mg, 51.4%) after column chromatography, $[α]_D$+22 (c=1, $CH_2Cl_2$). $^1$H NMR (400 MHz, $CDCl_3$) δ 0.88-0.92 (t, 3H, J=7.6 Hz), 1.48-1.63 (m, 3H), 1.98-2.10 (m, 1H), 2.53-2.99 (m, 15H), 3.96 (bs, 4H), 6.57-6.59 (d, 1H, J=7.6 Hz), 6.63-6.66 (d, 1H, J=7.6 Hz), 6.78 (s, 1H), 6.96-7.03 (t, 1H, J=7.6 Hz), 7.12-7.16 (t, 1H, J=7.6 Hz), 7.26-7.30 (m, 1H), 7.41-7.43 (d, 1H, J=8.4 Hz), 7.64-7.66 (d, 1H, J=8.0 Hz). The free base of (+)-40e was then converted into its HCl salt. m.p. 169-170° C. Anal. [$C_{28}H_{36}N_4O_2.2HCl$] C, H, N.

(−)-(4-{2-[(5-Hydroxy-1,2,3,4-tetrahydro-naphthalen-2-yl)-propyl-amino]-ethyl}-piperazin-1-yl)-(1H-indol-2-yl)-methanone ((−)-40e)

Compound (−)-40e was prepared following the Procedure G using (−)-39b (50 mg, 0.16 mmol) and indole-2-carboxylic acid (51 mg, 0.31 mmol) to give (−)-40e (33 mg, 55%) after column chromatography, $[α]_D$−21.6 (c=1, $CH_2Cl_2$). $^1$H NMR (400 MHz, $CDCl_3$) δ 0.885-0.92 (t, 3H, J=7.2 Hz), 1.51-1.61 (m, 3H), 2.10 (m, 1H), 2.50-2.99 (m, 15H), 3.96 (bs, 4H), 6.58-6.65 (dd, 2H, J=18.6, 6.84), 6.78 (5, 1H), 6.96-7.00 (t, 1H, J=8.0 Hz), 7.12-7.16 (t, 1H, J=7.2 Hz), 7.26-7.30 (t, 1H, J=7.6 Hz), 7.41-7.43 (d, 1H, J=8.4 Hz), 7.64-7.66 (d, 1H, J=7.6 Hz). The free base of (−)-40e was then converted into its HCl salt. m.p. 168-169° C. Anal. [$C_{28}H_{36}N_4O_2.2HCl$] C, H, N.

(4-{2-[(5-Hydroxy-1,2,3,4-tetrahydro-naphthalen-2-yl)-propyl-amino]-ethyl}-piperazin-1-yl)-(1H-indol-3-yl)-methanone (40f)

Compound 10f was prepared following Procedure G using 39b (50 mg, 0.16 mmol) and indole-3-carboxylic acid (35 mg, 0.21 mmol) to give 40f (38 mg, 53%) after column chromatography. $^1$H NMR (400 MHz, $CD_3OD$) δ 1.03-1.07 (t, 3H, J=7.2 Hz), 1.83-1.96 (m, 3H), 2.32 (s, 1H), 2.53-2.67 (m, 5H), 2.81-2.83 (m, 2H), 3.09-3.18 (m, 4H), 3.41-3.47 (m, 2H), 3.56-3.59 (m, 1H), 3.79 (bs, 4H), 6.61-6.63 (d, 1H, J=8.4 Hz), 6.64-6.66 (d, 1H, J=8.4 Hz), 6.96-6.99 (t, 1H, J=7.2 Hz), 7.13-7.21 (m, 1H), 7.41-7.51 (m, 1H), 7.62-7.64 (m, 1H), 7.71-7.73 (d, 1H, J=7.2 Hz), 7.83-7.84 (1H, J=7.2 Hz). The free base of 40f was converted into its HCl salt. m.p. 147-151° C. Anal. [$C_{28}H_{36}N_4O_2$.3HCl] C, H, N.

(4-{2-[(5-Hydroxy-1,2,3,4-tetrahydro-naphthalen-2-yl)-propyl-amino]-ethyl}-piperazin-1-yl)-(1H-indazol-3-yl)-methanone (40g)

Compound 10g was prepared by following Procedure G, using 39b (50 mg, 0.158 mmol) and indazole 3-carboxylic acid (45 mg, 0.277 mmol) to give 40 g (34 mg, 47%) after column chromatography. $^1$H NMR (400 MHz, CD$_3$OD) δ 1.04-1.07 (t, 3H, J=6.8 Hz), 1.83-1.93 (m, 3H), 2.31 (m, 1H), 2.62-2.70 (m, 5H), 2.81 (bs, 2H), 3.08-3.47 (m, 8H), 3.89 (bs, 2H), 4.08 (bs, 2H), 6.61-6.62 (m, 2H), 6.95-6.99 (t, 1H, J=7.2 Hz), 7.22-7.26 (t, 1H, J=8 Hz), 7.41-7.45 (t, 1H, J=6.4 Hz), 7.57-7.59 (d, 1H, J=8.8 Hz), 7.94-7.96 (d, J=8 Hz). The free base of 40 g was converted in to its HCl salt. m.p. 167-170° C. Anal. [$C_{27}H_{35}N_5O_2$.3HCl.2.5H$_2$O] C, H, N

Benzofuran-2-yl-(4-{2-[(5-hydroxy-1,2,3,4-tetrahydro-naphthalen-2-yl)-propyl-amino]-ethyl}-piperazin-1-yl)-methanone (40h)

Compound 40h was prepared following Procedure G using 39b (214 mg, 0.674 mmol) and benzofuran-2-carboxylic acid (131 mg, 0.809 mmol) to give 40h (108 mg, 35%) after column chromatography. $^1$H NMR (400 MHz, CD$_3$OD) δ 0.94-0.98 (t, 3H, J=7.2 Hz), 1.60-1.68 (m, 3H), 2.14-2.65 (m, 8H), 2.77-3.03 (m, 8H), 3.87 (bs, 4H), 6.55-6.60 (m 2H), 6.89-6.93 (t, 1H, J=7.2 Hz), 7.29-7.33 (t, 1H, J=6.4 Hz), 7.36 (s, 1H), 7.42-7.45 (t, 1H, J=7.2 Hz), 7.56-7.58 (d, 1H, J=8.8 Hz), 7.70-7.72 (d, 1H, J=7.2 Hz). The free base of 40h was converted in to its HCl salt. m.p. decomp at 140° C. Anal. [$C_{28}H_{35}N_3O$.2HCl.1.5H$_2$O] C, H, N.

Benzo[b]thiophen-2-yl-(4-{2-[(5-hydroxy-1,2,3,4-tetrahydro-naphthalen-2-yl)-propyl-amino]-ethyl}-piperazin-1-yl)-methanone (40i)

Compound 40i was prepared following Procedure G using 39b (175 mg, 0.551 mmol) and benzo[b]thiophene-2-carboxylic acid (118 mg, 0.661 mmol) to give 40i (263 mg, 64%) after column chromatography. $^1$H NMR (400 MHz, CD$_3$OD) 0.91-0.97 (t, 3H, J=7.2 Hz), 1.53-1.68 (m, 3H), 2.50-2.63 (m, 7H), 2.78-3.02 (m, 7H), 3.77-3.79 (bs, 4H), 6.55-6.59 (t, 2H, J=8 Hz), 6.89-6.93 (t, 1H, J=8.4 Hz), 7.40-7.46 (m, 2H), 7.61 (s, 1H), 7.85-7.91 (m, 2H). The free base of 40i was converted into its HCl salt. m.p. 131-134° C. Anal. [$C_{28}H_{35}N_3O_2S$.2HCl.1.5H$_2$O] C, H, N.

(4-{2-[(5-Hydroxy-1,2,3,4-tetrahydro-naphthalen-2-yl)-propyl-amino]-ethyl}-piperazin-1-yl)-quinolin-3-yl-methanone (40j)

Compound 40j was prepared following Procedure G using 39b (172 mg, 0.542 mmol) and quinoline-3-carboxylic acid (112 mg, 0.650 mmol) to give 40j (256 mg, 85%) after column chromatography. $^1$H NMR (400 MHz, CD$_3$OD) 0.93-0.96 (t, 3H, J=7.2 Hz), 1.57-1.59 (m, 3H), 2.18 (m, 2H), 2.55-3.00 (m, 14H), 3.55 (bs, 2H), 3.85 (bs, 2H), 6.53-6.58 (t, 2H, J=8 Hz), 6.88-6.91 (t, 1H, J=11.2 Hz), 7.81-7.72 (t, 1H, J=7.6 Hz), 7.85-7.88 (t, 1H, J=7.6 Hz), 8.03-8.1 (m, 2H), 8.45 (bs, 1H), 8.89 (bs, 1H). The free base of 40j was converted into its HCl salt. m.p. 142-146° C. Anal. [$C_{29}H_{36}N_4O_2$.3HCl.2H$_2$O] C, H, N.

4-(2-Hydroxy-ethyl)-piperazine-1-carboxylic acid tert-butyl ester (11)

To a mixture of compound 35 (3.00 g, 16.11 mmol), potassium carbonate (2.33 g, 48.32 mmol) in acetonitrile (50 ml) was added 2-bromoethanol (3.00 g, 24.17 mmol) under nitrogen atmosphere. The mixture was refluxed for 4 hrs, cooled, filtered, and concentrated. The crude mixture was purified by column chromatography (EtOAc:MeOH, 9:1) to give 41 (2.76 g, 75%). $^1$H NMR (400 MHz, CDCl$_3$) δ 1.46 (s, 9H), 2.45 (t, 4H, J=5.2 Hz), 2.55 (t, 2H, J=5.2 Hz), 3.44 (t, 4H, J=5.2 Hz), 3.62 (t, 2H, J=5.2 Hz).

(S)-tert-butyl-4-(2-((5-methoxy-1,2,3,4-tetrahydronaphthalen-2-yl)(propyl)amino)ethyl)piperazine-1-carboxylate (44)

To a solution of oxalyl chloride (0.76 ml, 8.76 mmol) in CH$_2$Cl$_2$ (20 ml) was added DMSO (1.10 ml, 17.52 mmol) at −78° C. and stirred for 5 min. Compound 41 (1.0 g, 4.38 mmol) was added to the mixture and was kept stirring for 30 min. The reaction temperature was raised to room temperature after addition of triethylamine (3.64 ml, 26.3 mmol). The solution was quenched with water and extracted with dicholomethame. The organic layer was dried over sodium sulfate and evaporated to afford crude 42 (0.99 g) in quantitative yield and was used in the next reaction without any further purification. Compound 42 (0.99 g, 4.34 mmol) was then reacted with 43 (0.87 g, 3.9 mmol) following Procedure A to provide 44 (1.1 g, 67%) %). [α]$_D^{20}$−32.43 (c 1.03 in CHCl$_3$). $^1$H NMR (400 MHz, CDCl$_3$) δ 0.88 (t, 3H, J=7.2 Hz), 1.46-1.61 (m, 12H), 2.04 (brs, 1H), 2.34-2.55 (m, 8H), 2.67-3.01 (m, 7H), 3.41-3.43 (m, 4H), 3.80 (s, 3H), 6.40 (d, 1H, J=8.0 Hz), 6.70 (d, 1H, J=7.6 Hz), 7.08 (m, 1H).

(S)-(4-{2-[(5-Hydroxy-1,2,3,4-tetrahydro-naphthalen-2-yl)-propyl-amino]-ethyl}-piperazin-1-yl)-(1H-indol-5-yl)-methanone (-45)

Compound 44 (1.1 g, 3.9 mmol) was refluxed in 48% HBr (30 ml) for 2 h, at which time the solution was cooled and concentrated to dryness. The crude hydrobromic salt was basified by the addition of sat. NaHCO$_3$ and the free base extracted with ethyl acetate. The organic layer was dried (Na$_2$SO$_4$), filtered, and concentrated to give the crude phenol, which was used as is in the next reaction. The synthesis of 45 was completed by reacting this material 290 mg, 0.67 mmol) with indole-5-carboxylic acid (130 mg, 0.81 mmol) following Procedure G to give 230 mg (74%) after column chromatography. [α]$_D^{20}$-21.0 (c=1, CHCl$_3$). $^1$H NMR (400 MHz, CDCl$_3$) δ 0.88 (t, 3H, J=7.2 Hz), 1.41-1.571 (m, 3H), 2.02 (brs, 1H), 2.48-2.80 (m, 13H), 2.87-2.95 (m, 2H), 3.63 (brs, 4H), 6.54-6.67 (m, 2H), 6.94-6.98 (m, 1H), 7.24-7.26 (m, 2H) 7.36-7.38 (m, 1H), 7.71 (s, 1H), 8.48 (s, 1H). The free base of was converted into its oxalate salt. m.p. 94-96° C. Anal. [$C_{28}H_{36}N_4O_2$.2.5(COOH)$_2$] C, H, N.

5-bromo-1-triisopropylsilyl-1H-indole (47)

5-Bromoindole (1.4 gm, 7.14 mmol) was dissolved in dry THF (50 ml) and cooled to 0° C., which was followed by the addition of NaH (0.34 g, 14.28 mmol) portion wise. The reaction mixture was allowed to stir at room temperature for 1 h. The reaction mixture was again cooled to 0° C. and triisopropylsilyl chloride (1.78 g, 9.28 mmol) was added drop wise. The mixture was allowed to warm to room temperature and was stirred overnight. The solvent was evaporated under reduced pressure and triturated with ethyl acetate (100 ml). The organic layer was washed with brine (50 ml) and dried over $Na_2SO_4$ and evaporated. The compound was purified by flash column chromatography using pure hexanes to afford colorless oily product 47 (1.90 g, 76%). $^1$H NMR (400 MHz, $CDCl_3$) δ 1.13 (d, 18H, J=8.0 Hz), 1.63-1.71 (m, 3H), 6.56 (d, 1H, J=3.2 Hz), 7.20-7.25 (m, 2H), 7.37 (d, 1H, J=8.8 Hz), 7.74 (d, 1H, J=2.0 Hz).

4-(1-triisopropylsilyl-1H-indole-5-yl)-piperazine-1-carboxylate (18)

A mixture of compound 47 (1.8 gm, 5.10 mmol), 35 (0.86 gm, 4.59 mmol), sodium tert-butoxide (0.638 gm, 6.64 mmol) and $PdCl_2[P(o-tol)_3]_2$ (0.20 gm, 0.23 mmol, 5% Wt) in 100 ml of xylenes was heated at 110° C. overnight. The reaction mixture was diluted with diethyl ether/hexanes (50:50) and filtered through a silica plug and eluted with 10% ethyl acetate in hexanes. All organic fractions were collected and evaporated in vacuo and the crude product was purified by flash column chromatography using diethyl ether/hexanes (20:80) to afford 48 (1.10 g, 52%). $^1$H NMR (400 MHz, $CDCl_3$) δ 1.13 (d, 18H, J=6.4 Hz), 1.48 (d, 9H), 1.63-1.70 (m, 3H), 3.08 (t, 4H, J=4.4 Hz), 3.60 (t, 4H, J=5.2 Hz), 6.53 (d, 1H, J=2.4 Hz), 6.86-6.89 (dd, 1H, J=2.4 Hz, J=9.2 Hz), 7.13 (d, 1H, J=2.0 Hz), 7.20 (d, 1H, J=3.2 Hz), 7.40 (d, 1H, J=9.2 Hz).

tert-butyl 4-(1H-indole-5-yl)-piperazine-1-carboxylate (49)

To a stirring solution of compound 48 (1.10 gm, 2.40 mmol) in THF (20 ml) was added tetrabutylammonium fluoride (1M in THF, 15 ml). The reaction mixture was stirred for 3 h to complete the reaction. The solvent was evaporated in vacuo and triturated with diethyl ether (100 ml). The ether layer was washed with saturated $NaHCO_3$ (20 ml) and brine (20 ml), dried over $MgSO_4$ and evaporated in vacuo. The crude product was purified by flash column chromatography over silica gel using ethyl acetate/hexanes (30:70) to afford 49 (0.71 g, 95%). $^1$H NMR (400 MHz, $CDCl_3$) δ 1.49 (s, 9H), 3.07 (t, 4H, J=4.8 Hz), 3.61 (t, 4H, J=5.2 Hz), 6.46-6.47 (m, 1H), 6.94-6.97 (dd, 1H, J=2.0 Hz, J=8.8 Hz), 7.16 (m, 2H), 7.30 (d, 1H, J=8.8 Hz), 8.15 (bs, 1H).

2-[4-(1H-Indol-5-yl)-piperazin-1-yl]-N-(7-methoxy-1,2,3,4-tetrahydro-naphthalen-2-yl)-N-propyl-acetamide (51)

To a stirring solution of compound 49 (800 mg, 2.65 mmol) in dry $CH_2Cl_2$ (20 ml) was added trifluoroacetic acid (20 ml). After stirring for 2 h at room temperature the solvent was removed in vacuo and the crude semi solid residue collected was triturated with ethyl acetate and filtered to get 50 (780 mg, 94%). Compound 50 (780 mg, 3.87 mmol), 33a (1.15 g, 3.87 mmol), $K_2OC_3$ (474 mg, 3.44 mmol), and acetonitrile (75 ml) were refluxed for 3 hrs. The reaction mixture was cooled, filtered, and concentrated. The crude material was purified by column chromatography (EtOAc:MeOH, 95:5) to yield 51 (220 mg, 22%). $^1$H NMR (400 MHz, $CDCl_3$) δ 0.81 (t, 3H, J=7.2 Hz), 1.38-1.46 (m, 2H), 1.51-1.61 (m, 1H), 1.94 (d, 1H, J=12.0 Hz), 2.46 (t, 2H, J=7.2 Hz), 2.61-2.75 (m, 4H), 2.96-3.08 (m, 5H), 3.40 (s, 2H), 3.56-3.85 (m, 4H), 6.40 (bs, 1H), 6.47 (d, 1H, J=2.0 Hz), 6.51-6.54 (dd, 1H, J=2.4 Hz and 8.0 Hz), 6.82 (d, 1H, J=8.0 Hz), 6.88-6.90 (dd, 1H, J=2.0 Hz and 8.8 Hz), 7.09-7.11 (m, 2H), 7.25 (d, 1H, J=8.8 Hz), 8.12 (bs, 1H).

7-((2-(4-(1H-indol-5-yl)piperazin-1-yl)ethyl)(propyl) amino)-5,6,7,8-tetrahydro-naphthalen-2-ol (52)

To a stirring cold solution of compound 51 (220 mg, 0.492 mmol) in dry THF was added $BH_3$.THF (211 mg, 2.46 mmol) and the reaction mixture was refluxed overnight. After cooling the reaction mixture to room temperature, 1 ml of methanol was added and the solvent was evaporated. The residue was dissolved in 15 ml of conc. HBr and refluxed for 1 h. The solvent was evaporated and the crude product was dissolved in dichloromethane (50 ml). The organic layer was washed with saturated $NaHCO_3$ (30 ml) and dried over $Na_2SO_4$. The solvent was evaporated and the crude product was purified by flash column chromatography over silica gel using ethyl acetate/MeOH/$Et_3$N (95:5:0.2) to afford 52 (20 mg). $^1$H NMR (400 MHz, $CD_3OD$) δ 0.95 (t, 3H, J=7.6 Hz), 1.53-1.67 (m, 3H), 2.08 (d, 1H, J=9.6 Hz), 2.60-2.88 (m, 14H), 3.10-3.13 (m, 5H), 6.35 (d, 1H, J=2.8 Hz), 6.52-6.55 (m, 2H), 6.87 (d, 1H, J=8.8 Hz), 6.91-6.94 (dd, 1H, J=8.8 Hz and 2.4 Hz), 7.16-7.17 (m, 2H), 7.29 (d, 1H, J=8.8 Hz). Free base converted into oxalate salt, m.p. 179-183° C.

Biological Experiments: Potencies at DA D2 and D3 Receptors.

Compounds were tested for inhibition of radioligand binding to DA receptors as described in our previous study. Briefly, membranes from human embryonic kidney (HEK) 293 cells expressing rat D2L and D3 receptors were incubated with each test compound and [$^3$H]spiperone (0.6 nM, 15 Ci/mmole, Perkin Elmer) for 1 h at 30° C. in 50 mM Tris-HCl (pH 7.4), 0.9% NaCl, and 0.025% ascorbic acid. (+)-Butaclamol (2 μM) was used to define nonspecific binding. Assays were terminated by filtration in the MACH 3-96 Tomtec harvester (Wallac, Gaithersburg, Md.). $IC_{50}$ values were estimated by nonlinear regression analysis with the logistic model in the least squares fitting program ORIGIN, and converted to inhibition constants ($K_i$) by the Cheng-Prusoff equation. In this conversion, the $K_d$ values for [$^3$H] spiperone binding were 0.057 nM for D2 receptors and 0.125 nM for D3 receptors.

Measurement of Stimulation of Dopamine D2 and D3 Receptors—[$^{35}$S]GTPγS Binding:

All procedures were as described in our recent work. Briefly, Chinese hamster ovary (CHO) cells expressing human D2L receptors and ATt-20 cells expressing human D3 receptors served as the source for membrane fractions. GTPγS binding assays contained test drug, DA (1 mM for D2 cells, and 100 μM for D3 cells) as indicator of binding plateau, [$^{35}$S]GTPγS (0.17 nM, 1,250 Ci/mmole, Perkin Elmer), and cell suspension (with GDP for final concentration in assay of 3 μM for D2 or 6 μM for D3). After incubation at room temperature in a shaking water bath for 60 minutes, cells were harvested by filtration and assayed for $^{35}$S radioactivity. Nonspecific binding of [$^{35}$S]GTPγS was measured with 10 μM GTPγS and the EC50 (concentration producing half-maximal stimulation) of the test drug was estimated by nonlinear logarithmic fitting (logistics model) with OriginPro 7.0. The plateau binding (maximal binding stimulation) with test drug was expressed as percent of maximal binding observed with the full agonist DA (% Emax).

4. Compounds Having Formula VII

Figure 23:
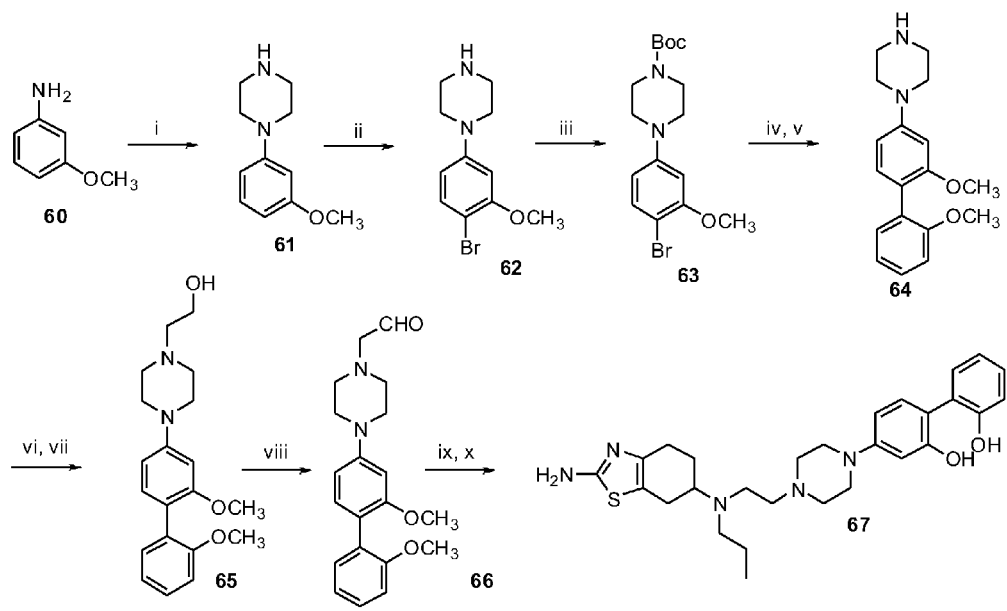
FIG. 23 provides part of a synthetic scheme for preparing compounds of an embodiment of the present invention.

Compounds having formula VII are prepared via scheme 10 set forth in FIG. 23. In step (i), compound 60 is converted to compound 61 with bis-(2-Chloro-ethyl)-amine. In step (ii), compound 61 is converted to compound 62 with CH₃COOH, Br₂. Compound 62 is converted to compound 63 with (Boc)₂O and Et3N in step (iii). Compound 63 is converted to compound 64 in step (iv) with 2-Methoxy boronic acid, Pd[P(Ph)3] followed by combining with TFA in step (v). Compound 64 is converted to compound 65 in step (vi) by reaction with (2-Bromo ethoxy)-tert-butyl-dimethyl-silane and K₂CO₃ followed by reaction with Bu₄NF in step (v). Next, compound 65 is converted to compound 66 in step (viii) by reaction with (COCl)₂, DMSO, and Et₃N. Finally, compound 66 is treated with Pramipexole, NaBH(OAc)₃ in sep (ix) and then BBr3 in step (x) to form compound 67.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A compound having formula I for treating a neurodegenerative disease:

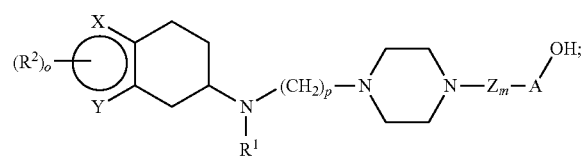

or a pharmaceutically acceptable salt thereof;
wherein:
$R^1$ is $C_{1-8}$ alkyl, $C_{2-8}$ alkenyl, $C_{2-8}$ alkynyl, $C_{4-8}$ cycloalkyl, $C_{4-8}$ cycloalkenyl, or $C_{6-10}$ aryl;

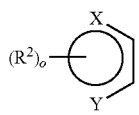

is

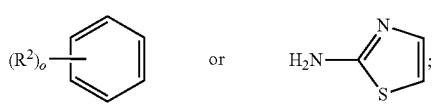

$R^2$ groups are $C_{1-8}$ alkyl, $C_{2-8}$ alkenyl, $C_{2-8}$ alkynyl, $C_{4-8}$ cycloalkyl, $C_{4-8}$ cycloalkenyl; $C_{6-10}$ aryl, —$NR^3_q$ where $R^3$ individually are H, $C_{1-8}$ alkyl, $C_{2-8}$ alkenyl, $C_{4-8}$ cycloalkyl, $C_{4-8}$ cycloalkenyl, $C_{6-10}$ aryl and q is 2;
o is 0, 1, 2, 3, or 4;
A is quinolinyl or an optionally substituted quinolinyl, the optionally substituted quinolinyl being substituted by a component selected from the group consisting of —OH, $C_{1-4}$ alkyl, $C_{2-4}$ alkenyl, $C_{5-7}$ cycloalkyl, $C_{5-7}$ cycloalkenyl, halo, $C_{1-4}$ aldehyde, and —$NR^4_q$ where $R^4$ is H, $C_{1-8}$ alkyl, $C_{2-8}$ alkenyl, $C_{4-8}$ cycloalkyl, $C_{4-8}$ cycloalkenyl, or $C_{6-10}$ aryl; and q is 2;
p is an integer from 1 to 6; and
$Z_m$ is absent, —$CH_2$— or —CO—.

2. The compound of claim 1 having formula IIa or IIb:

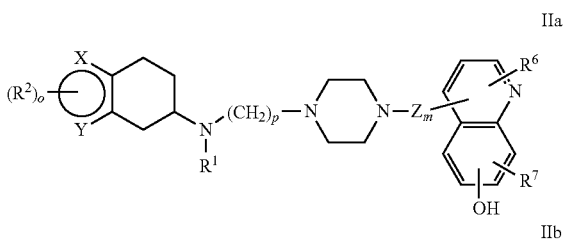

wherein $R^6$ and $R^7$ are Cl, F, OH, H, $C_{1-8}$ alkyl, $C_{2-8}$ alkenyl, $C_{4-8}$ cycloalkyl, $C_{4-8}$ cycloalkenyl, or $C_{6-10}$ aryl.

3. The compound of claim 1 having formula IIIa or formula IIIb:

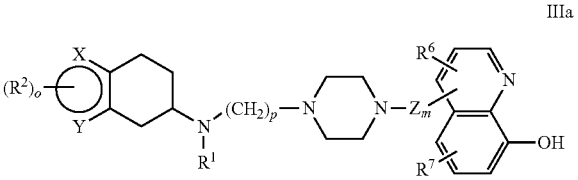

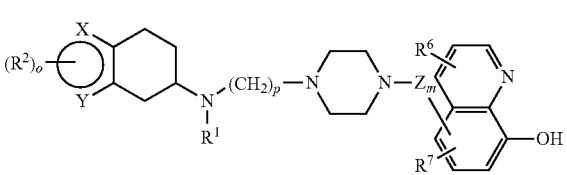

wherein $R^6$ and $R^7$ are Cl, F, OH, H, $C_{1-8}$ alkyl, $C_{2-8}$ alkenyl, $C_{4-8}$ cycloalkyl, $C_{4-8}$ cycloalkenyl, or $C_{6-10}$ aryl.

4. A compound selected from the group consisting of:

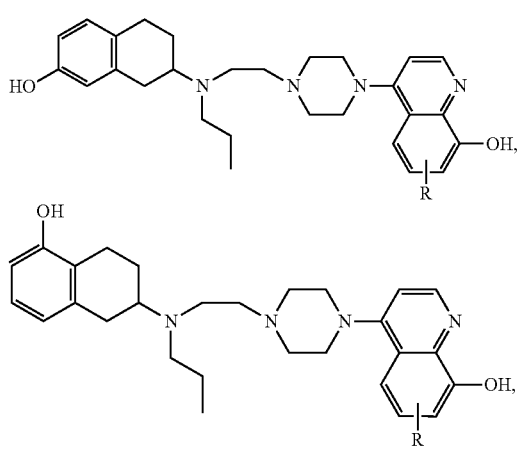

-continued

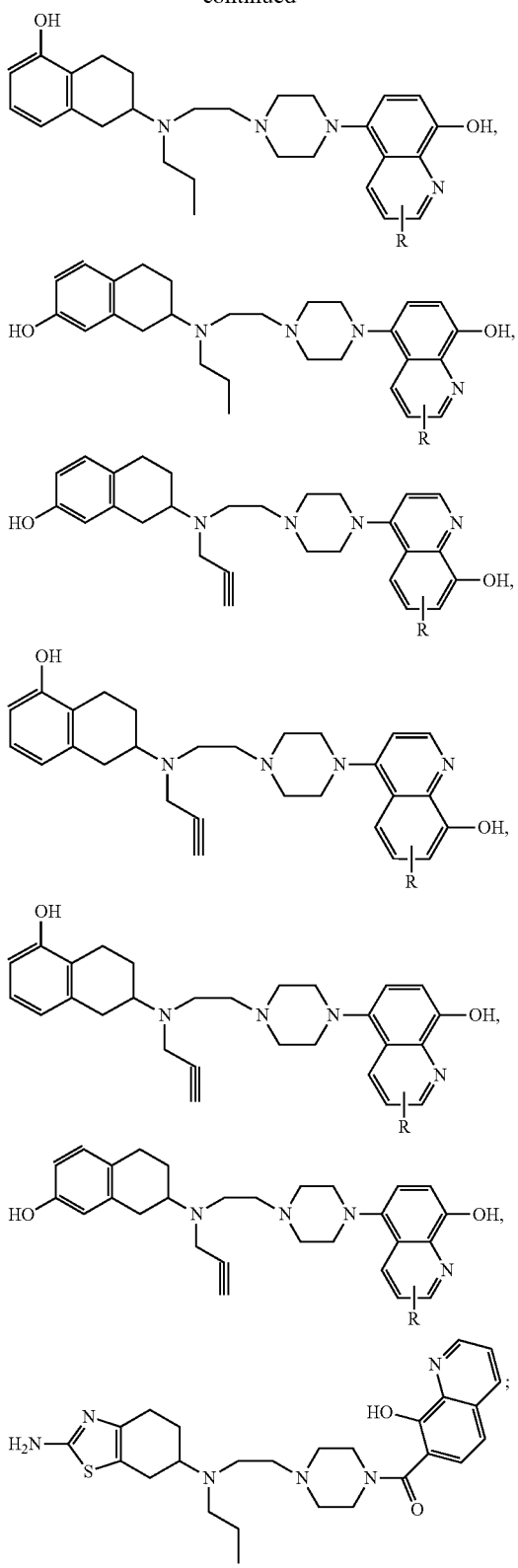

and pharmaceutically acceptable salt thereof, wherein R is hydrogen or $C_{1-4}$ alkyl.

5. The compound of claim 4 wherein R is hydrogen.

6. A compound selected from the group consisting:

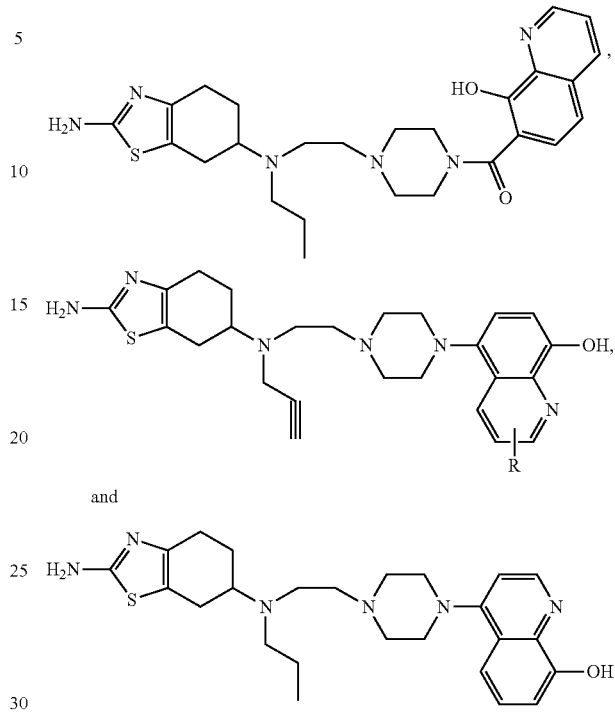

and pharmaceutically acceptable salts thereof, wherein R is hydrogen or $C_{1-4}$ alkyl, and n is 0, 1, 2 or 3.

7. The compound of claim 6 wherein R is hydrogen.

8. The compound of claim 1 wherein A is substituted by a component selected from the group consisting of $C_{1-4}$ alkyl, $C_{2-4}$ alkenyl, $C_{5-7}$ cycloalkyl, $C_{5-7}$ cycloalkenyl, halo, $C_{1-4}$ aldehyde, and $-NR^4_q$ where $R^4$ is H, $C_{1-8}$ alkyl, $C_{2-8}$ alkenyl, $C_{4-8}$ cycloalkyl, $C_{4-8}$ cycloalkenyl, or $C_{6-10}$ aryl; and q is 2.

9. The compound of claim 1 wherein A is substituted by a component selected from the group consisting of $C_{1-4}$ alkyl, $C_{2-4}$ alkenyl, $C_{5-7}$ cycloalkyl, $C_{5-7}$ cycloalkenyl, and halo.

10. The compound of claim 1 wherein:

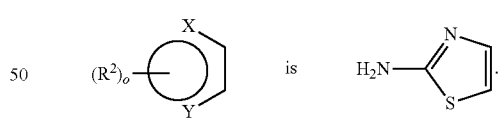

11. The compound of claim 1 having a formula selected from the group consisting of:

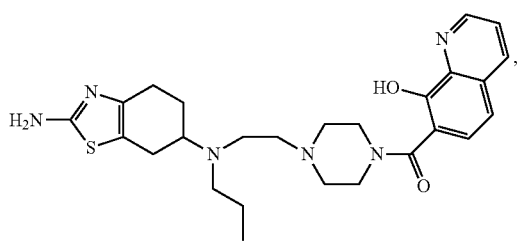

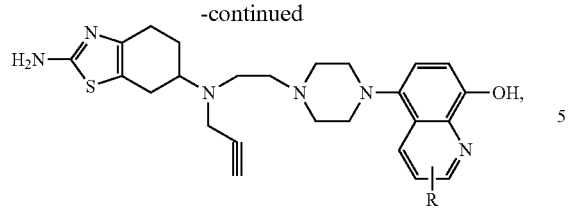
and
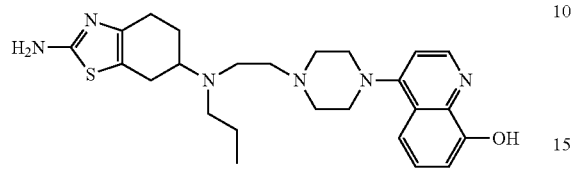
wherein R is hydrogen or $C_{1-4}$ alkyl.
* * * * *